US010858382B2

(12) United States Patent
Colacot et al.

(10) Patent No.: US 10,858,382 B2
(45) Date of Patent: Dec. 8, 2020

(54) ALLYL PHOSPHINE COMPLEXES OF PALLADIUM AND THEIR USE IN CATALYSIS

(71) Applicant: JOHNSON MATTHEY PUBLIC LIMITED COMPANY, London (GB)

(72) Inventors: Thomas Colacot, West Deptford, NJ (US); Ruishan Chow, West Chester, PA (US); Andrew Jon DeAngelis, West Deptford, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/284,841

(22) Filed: Feb. 25, 2019

(65) Prior Publication Data
US 2019/0241589 A1 Aug. 8, 2019

Related U.S. Application Data

(62) Division of application No. 15/318,106, filed as application No. PCT/GB2015/050835 on Mar. 20, 2015, now Pat. No. 10,253,056.
(Continued)

(51) Int. Cl.
| | |
|---|---|
| *C07F 15/00* | (2006.01) |
| *C07D 215/38* | (2006.01) |
| *C07B 37/04* | (2006.01) |
| *C07B 43/04* | (2006.01) |
| *C07D 401/06* | (2006.01) |
| *C07D 403/04* | (2006.01) |
| *C07D 405/04* | (2006.01) |
| *C07D 409/04* | (2006.01) |
| *C07D 471/04* | (2006.01) |

(Continued)

(52) U.S. Cl.
CPC ........... *C07F 15/006* (2013.01); *C07B 37/04* (2013.01); *C07B 43/04* (2013.01); *C07C 17/32* (2013.01); *C07C 45/68* (2013.01); *C07D 213/127* (2013.01); *C07D 213/24* (2013.01); *C07D 213/50* (2013.01); *C07D 213/56* (2013.01); *C07D 215/38* (2013.01); *C07D 295/096* (2013.01); *C07D 307/46* (2013.01); *C07D 401/06* (2013.01); *C07D 403/04* (2013.01); *C07D 405/04* (2013.01); *C07D 409/04* (2013.01); *C07D 471/04* (2013.01)

(58) Field of Classification Search
CPC ............. C07F 15/006; C07D 213/127; C07D 213/24; C07D 213/50
See application file for complete search history.

(56) References Cited

U.S. PATENT DOCUMENTS

| | | | | |
|---|---|---|---|---|
| 9,777,030 B2* | 10/2017 | Colacot | ............... | B01J 31/2291 |
| 2013/0165660 A1* | 6/2013 | Colacot | ............... | B01J 31/2404 |
| | | | | 546/346 |
| 2017/0120231 A1 | 5/2017 | Colacot et al. | | |

FOREIGN PATENT DOCUMENTS

| | | |
|---|---|---|
| RU | 2239639 C1 | 11/2004 |
| WO | 2011/161451 A1 | 12/2011 |

OTHER PUBLICATIONS

Kisanga et al., "Development, Synthetic Scope, and Mechanistic Studies of the Palladium-Catalyzed Cycloisomerization of Functionalized 1,6-Dienes in the Presence of Silane," J.Am.Chem.Soc., 2000, 122, pp. 10017-10026.
(Continued)

*Primary Examiner* — Pancham Bakshi
(74) *Attorney, Agent, or Firm* — BakerHostetler

(57) ABSTRACT

The present invention provides a palladium(II) complex of formula (1) or a palladium(II) complex of formula (2).

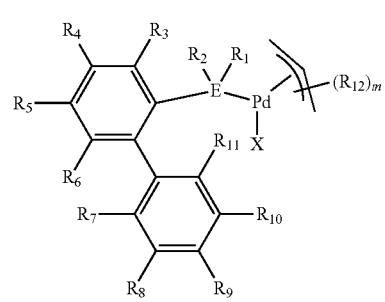

(1)

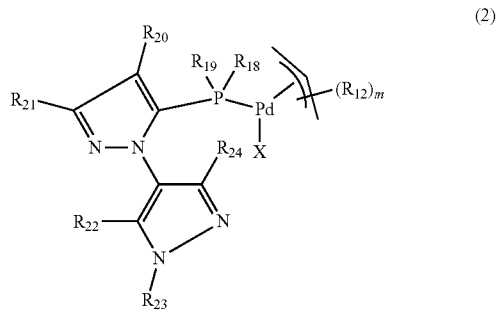

(2)

$R_1$, $R_2$, $R_3$, $R_4$, $R_5$, $R_6$, $R_7$, $R_8$, $R_9$, $R_{10}$, $R_{11}$, $R_{12}$, $R_{18}$, $R_{19}$, $R_{20}$, $R_{21}$, $R_{22}$, $R_{23}$ and $R_{24}$, m, E and X are described in the specification.
The invention also provides a process for the preparation of the complexes, and their use in carbon-carbon and carbon-heteroatom coupling reactions.

12 Claims, 7 Drawing Sheets

Related U.S. Application Data

(60) Provisional application No. 62/011,168, filed on Jun. 12, 2014.

(51) Int. Cl.
| | |
|---|---|
| *C07D 295/096* | (2006.01) |
| *C07D 213/127* | (2006.01) |
| *C07D 213/24* | (2006.01) |
| *C07D 213/50* | (2006.01) |
| *C07D 213/56* | (2006.01) |
| *C07D 307/46* | (2006.01) |
| *C07C 45/68* | (2006.01) |
| *C07C 17/32* | (2006.01) |

(56) References Cited

OTHER PUBLICATIONS

Faller, et al., "Retention of Configuration and Regiochemistry in Allylic Alkulations via the Memory Effect", Organometallics, vol. 23(9), 2004, pp. 2179-2185.
Gladiali, et al., "Asymmetric Allylic Alkylation Catalyzed by Pd(II)-Complexes with (S)- BINPO, a Hemilabile Axially Chiral, P,O-Heterodonor Inducer", Tetrahedron: Asymmetry, vol. 15(9), 2004, pp. 1477-1485.
Grabulosa, et al: "Better Performance of Monodentate P-Stereogenic Phosphanes Compared to Bidentate Analogues in Pd-Catalyzed Asymmetric Allylic Alkylations", European Journal of Inorganic Chemistry, vol. 2010. No. 21. Jun. 2, 2010, pp. 3372-3383.
Grabulosa, et al: "P-Stereogenic monophosphines in Pd-catalysed enantioselective hydrovinylation of styrene", Journal of Organometallic Chemistry vol. 696, No. 11, Feb. 11, 2011, pp. 2338-2345.
Great Britain Search Report dated Dec. 14, 2015, in corresponding GB priority application.
Ficks, et al, "MOP-Phosphonites: A Novel Ligand Class for Asymmetric Catalysis", Dalton Transactions, vol. 41(12), 2012, pp. 3515-3522.
PCT/GB2015/050835, International Search Report dated Aug. 21, 2015.
Kawatsura, et al, "Palladium-Catalyzed Asymmetric Reduction of Racemic Allylic Esters with Formic Acid: Effects of Phosphine Ligands on Isomerization of (pie)-Allyl Palladium Intermediates and Enantioselectivity", Tetrahedron, vol. 56(15),2000, pp. 2247-2257.
Noel-Duchesneau, et al, "Tailoring Buchwald-Type Phosphines with Pyrimidinium Betaines as Versatile Aryl Group Surrogates", Organometallics, vol. 33, Sep. 3, 2014, pp. 5085-5088.
Ohmura, et al: "Switch of Regioselectivity in Palladium-Catalyzed Silaboration of Terminal Alkynes by Ligand-Dependent Control of Reductive Elimination", Journal of the American Chemical Society, vol. 132, No. 35, Sep. 8, 2010, pp. 12194-12196.
Kocovsky, et al, "Palladium(II) Complexes of 2-Dimethylamino-2'-diphenylphosphino-1,1'-binaphthyl (MAP) with Unique P, Co-Coordination and Their Catalytic Activity in Allylic Substitution, Hartwig-Buchwald Amination, and Suzuki Coupling", Journal of American Chemical Society, Aug. 6, 1999, vol. 121, pp. 7714-7715.
Rodriguez, et al: "Palladocarbosilane dendrimers as catalysts for the asymmetric hydrovinylation of styrene in supercritical carbon dioxide", Journal of Organometallic Chemistry, vol. 693, No. 10, May 1, 2008 pp. 1857-1860.
Borjian, et al: "NMR Studies of the Species Present in Cross-Coupling Catalysis Systems Involving Pd(η3-1-Ph-C3H4)(η5-C5H5) and [Pd(η3-1-Ph-C3H4)Cl]2 Activated by PBut3, XPhos, and Mor-Dalphos: Nonexistence of Pd(XPhos)n and Pd(Mor-Dalphos)n (n=1, 2) at Moderate Temperatures", Organometallics, vol. 33, Jul. 31, 2014, pp. 3936-3940.
Thoumazet, et al: "Testing Phosphanes in the Palladium-Catalysed Allylation of Secondary and Primary Amines", European Journal of Inorganic Chemistry, vol. 2006. No. 19. Oct. 1, 2006, pp. 3911-3922.
Auburn, et al: "Asymmetric Synthesis, Asymmetric Catalytic Allylation Using Palladium Chiral Phosphine Complexes," Journal of the American Chemical Society, 1985, 107, pp. 2033-2046.
Dent, "Some Observations on the Preparation of π-Allylic Palladium Chloride Complexes," Journal of the Chemical Society, 1964, p. 1585.
Ficks, "MOP-phosphonites: A Novel Ligand Class for Asymmetric Catalysis," Dalton Transactions, 2012, 41, pp. 3515-3522.
Marion, et al, "Modified (NHC)Pd(allyl)Cl (NHC=N-Heterocyclic Carbene) Complexes for Room-Temperature Suzuki-Miyaura and Buchwald-Hartwig Reactions," Journal of the American Chemical Society, 2006, 128, pp. 4101-4111.
Miura et al, "Synthesis of 6-Substituted 3-(Alkoxycarbonyl)-5-aryl-α-Pyrones," Synthesis, 2014, 46, p. 496.
Nicholson, et al., "The Mechanism of Formation of π-Allylic Palladium(II) Chlorides from Sodium Chloropalladite, Allylic Chlorides, and Carbon Monoxide Reacting in Aqueous Methanol," Journal of the Chemical Society, Chemical Communications., Issue 6, 1966, p. 174.
Tang et al., "A General and Special Catalyst For Suzuki-Miyaura Coupling Processes," Angew. Chem. Int. Ed. 2010, 49, pp. 5879-5883.
Xu et al, "Efficient Syntheses of Korupensamines A, B and Michellamine B by Asymmetric Suzuki-Miyaura Coupling Reactions," Journal of the American Chemical Society, 2014 136(2), pp. 570-573.
Zhao et al., "An Efficient Method for Sterically Demanding Suzuki-Miyaura Coupling Reactions," Chemistry: A European Journal, 2013 19(7), pp. 2261-2265.

\* cited by examiner

ALLYL PHOSPHINE COMPLEXES OF PALLADIUM AND THEIR USE IN CATALYSIS

CROSS REFERENCE TO RELATED APPLICATIONS

This is a divisional of U.S. patent application Ser. No. 15/318,106, filed Dec. 12, 2016, which is a national stage of International Patent Application No. PCT/GB2015/050835, filed Mar. 20, 2015, which claims the benefit of U.S. Provisional Patent Application No. 62/011,168, filed Jun. 12, 2014, all of which are incorporated by reference herein.

TECHNICAL FIELD

The present invention relates to optionally substituted π-allyl palladium complexes and their use thereof in coupling reactions.

BACKGROUND

WO2011/161451 (to Johnson Matthey PLC) describes π-allyl complexes, such as π-allyl palladium complexes and π-allyl nickel complexes.

Faller et al (Organometallics, 2004, 23, 2179-2185) describes the preparation of the complex (crotyl)Pd(Cy$_2$P-biphenyl)Cl in mechanistic investigations. Faller et al neither disclose nor suggest that the complex may be used a precatalyst for coupling reactions.

The use of [(allyl)PdCl]$_2$ or [(cinnamyl)PdCl]$_2$ in combination with biaryl/heteroaryl phosphine ligands, such as Buchwald ligands in coupling reactions has proven to be of limited and unpredictable success. In an attempt to overcome the limitations of catalyst generation from palladium sources such as [(allyl)PdCl]$_2$, Pd(dba)$_x$ (x=1, 1.5 or 2), or Pd(OAc)$_2$ with Buchwald ligand combinations, the Buchwald group at MIT has introduced a library of three generations of palladacycle precatalysts utilizing bulky biarylphosphines as shown below.

Palladacycle Precatalysts

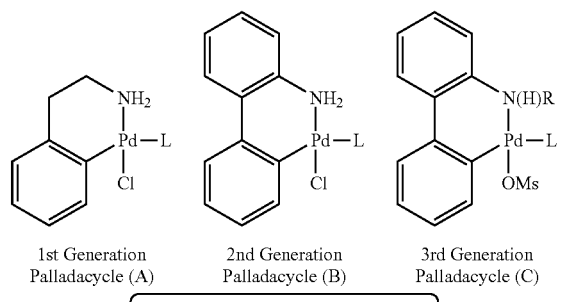

1st Generation Palladacycle (A)   2nd Generation Palladacycle (B)   3rd Generation Palladacycle (C)

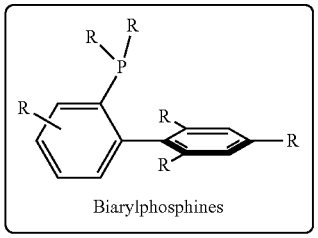

R = H, Me, Ph

The palladacycles, however, demonstrate a number of limitations. Firstly, the synthesis of the 1$^{st}$ generation palladacycles requires several steps including the generation of an unstable intermediate [(TMEDA)PdMe$_2$]. The syntheses of the 2$^{nd}$ and 3$^{rd}$ generation palladacycles require the use of potentially toxic 2-aminobiphenyl, which can be contaminated with the highly toxic 4-isomer, requiring the need for high purity raw material. Furthermore, the activation of the 2nd and 3d generation palladacycles generates an equivalent of genotoxic carbazole. The starting material aminobiphenyl and the by-product carbazole can contaminate reaction mixtures. Hence, purification can be complicated, in addition to the consideration of health and safety concerns involved in handling these materials. Moreover, the reductively eliminated carbazole (as illustrated in the following scheme) can consume aryl-electrophile starting material and also significantly retard the rate of some cross-coupling reactions.

Activation of a Palladacycle

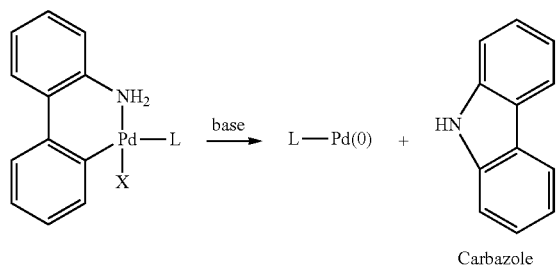

Carbazole

The activation of the very recent N-substituted 3$^{rd}$ generation palladacycles generates an equivalent of either N-methylcarbazole or N-phenylcarbazole and little is known about their toxicity. The N-substituted version of the 3$^{rd}$ generation palladacycles also require an additional synthetic step to prepare relative to the unsubstituted analogues.

There remains a need to provide palladium precatalysts with well-defined ligand/palladium ratios that overcome the limitations in the prior art.

SUMMARY

In many cases, allyl dimers such as [(allyl)PdCl]$_2$ do not function well as palladium sources with biarylphosphines and there are difficulties in forming active catalysts with the allyl dimer/Buchwald ligand combination. The present inventors, however, have discovered a class of optionally substituted π-allylpalladium complexes, which may be employed to effect a variety of coupling reactions, such as C—N and C—C bond formation reactions. In certain embodiments, the π-allyl complexes are highly active catalysts. In certain embodiments, the π-allyl complexes are stable to air and moisture at ambient temperatures.

In one aspect, the invention provides a palladium(II) complex of formula (1):

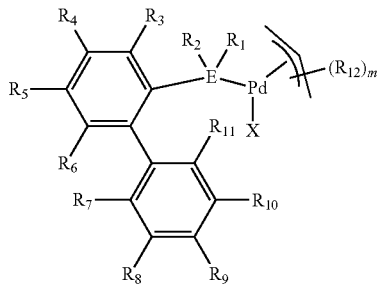
(1)

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or
$R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above; $R_{12}$ is an organic group having 1-20 carbon atoms;
m is 0, 1, 2, 3, 4 or 5;
E is P or As; and
X is a coordinating anionic ligand;
provided that the palladium complex of formula (1) is not (π-crotyl)PdCl(dicyclohexylphosphino-2-biphenyl).

In another aspect, the invention provides a palladium complex of formula (2):

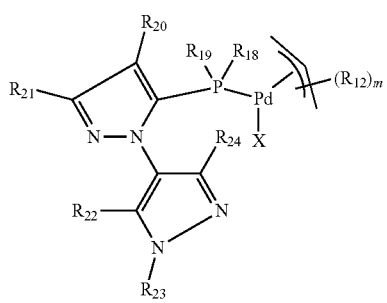
(2)

wherein:
$R_{18}$ and $R_{19}$ are independently selected from the group consisting of -Me, -Et, -$^n$Pr, -$^i$Pr, -$^n$Bu, -$^i$Bu, cyclohexyl and cycloheptyl;
$R_{12}$ is an organic group having 1-20 carbon atoms;
$R_{20}$, $R_{21}$, $R_{22}$, $R_{23}$ and $R_{24}$ are independently —H or organic groups having 1-20 carbon atoms; or one or both pairs selected from $R_{20}/R_{21}$ or $R_{22}/R_{23}$ may independently form a ring structure with the atoms to which they are attached;
m is 0, 1, 2, 3, 4 or 5; and
X is a coordinating anionic ligand.

In another aspect, the invention provides a process for the preparation of a complex of formula (1) or a complex of formula (2) comprising the step of reacting a complex of formula (3) with a monodentate biaryl ligand of formula (4) or a monodentate bi-heteroaryl tertiary phosphine ligand of formula (5) to form the complex of formula (1) or the complex of formula (2),

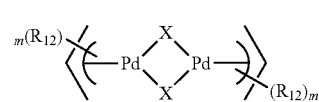
(3)

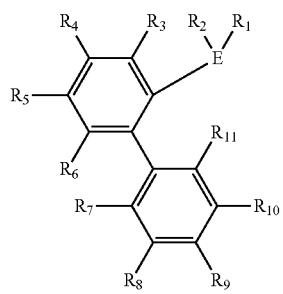
(4)

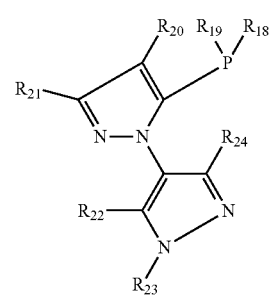
(5)

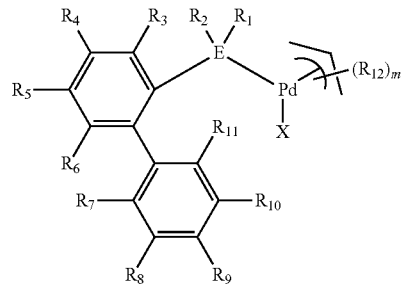
(1)

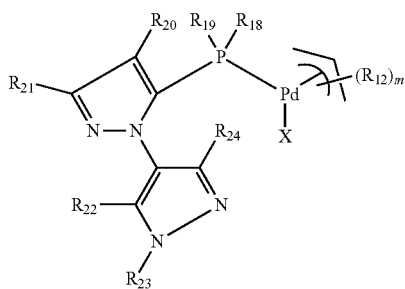
(2)

wherein,
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or one or more pairs selected from $R_1/R_3$, $R_2/R_3$, $R_3/R_4$, $R_4/R_5$, $R_5/R_6$, $R_7/R_8$, $R_8/R_9$, $R_9/R_{10}$ or $R_{10}/R_{11}$ independently may form a ring structure with the carbon atoms to which they are attached;

$R_{12}$ is an organic group having 1-20 carbon atoms;

$R_{18}$ and $R_{19}$ are independently selected from the group consisting of -Me, -Et, -$^n$Pr, -$^i$Pr, -$^n$Bu, -$^i$Bu, cyclohexyl and cycloheptyl;

$R_{20}$, $R_{21}$, $R_{22}$, $R_{23}$ and $R_{24}$ are independently —H organic groups having 1-20 carbon atoms; or one or both pairs selected from $R_{20}/R_{21}$ or $R_{22}/R_{23}$ independently may form a ring structure with the atoms to which they are attached;

m is 0, 1, 2, 3, 4 or 5;

E is P or As; and

X is a coordinating anionic ligand;

provided that the palladium complex of formula (1) is not (n-crotyl)PdCl(dicyclohexylphosphino-2-biphenyl).

In another aspect, the present invention provides a process for carrying out a carbon-carbon coupling reaction in the presence of a catalyst, the process comprising:

(a) the use of a complex of formula (1):

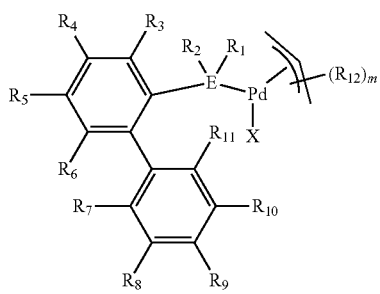

wherein:

$R_1$ and $R_2$ are independently organic groups having 1-20 carbon atoms, or $R_1$ and $R_2$ are linked to form a ring structure with E;

$R_3$, $R_4$, $R_5$, $R_6$, $R_7$, $R_8$, $R_9$, $R_{10}$ and $R_{11}$ are independently —H or organic groups having 1-20 carbon atoms; or $R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above; $R_{12}$ is an organic group having 1-20 carbon atoms;

m is 0, 1, 2, 3, 4 or 5;

E is P or As; and

X is a coordinating anionic ligand;

or:

(b) a complex of formula (2) as defined herein.

In another aspect, the invention provides a process for carrying out a carbon-heteroatom coupling reaction in the presence of a catalyst, the process comprising:

(a) the use of a complex of formula (1):

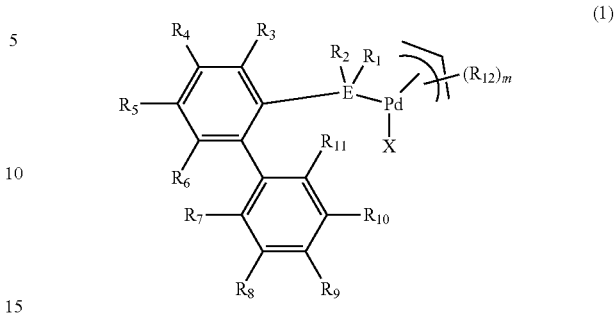

wherein:

$R_1$ and $R_2$ are independently organic groups having 1-20 carbon atoms, or $R_1$ and $R_2$ are linked to form a ring structure with E;

$R_3$, $R_4$, $R_5$, $R_6$, $R_7$, $R_8$, $R_9$, $R_{10}$ and $R_{11}$ are independently —H or organic groups having 1-20 carbon atoms; or $R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above;

$R_{12}$ is an organic group having 1-20 carbon atoms;

m is 0, 1, 2, 3, 4 or 5;

E is P or As; and

X is a coordinating anionic ligand;

or:

(b) a complex of formula (2) as defined herein.

In another aspect, the invention provides the use of a complex of formula (1) or a complex of formula (2) as a catalyst is carbon-carbon coupling reactions, wherein:

(a) the complex of formula (1) is:

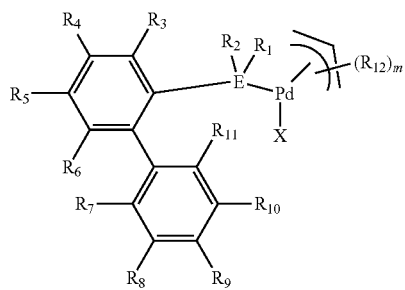

wherein:

$R_1$ and $R_2$ are independently organic groups having 1-20 carbon atoms, or $R_1$ and $R_2$ are linked to form a ring structure with E;

$R_3$, $R_4$, $R_5$, $R_6$, $R_7$, $R_8$, $R_9$, $R_{10}$ and $R_{11}$ are independently —H or organic groups having 1-20 carbon atoms; or $R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above;

$R_{12}$ is an organic group having 1-20 carbon atoms;

m is 0, 1, 2, 3, 4 or 5;

E is P or As; and
X is a coordinating anionic ligand;
and:
(b) the complex of formula (2) as defined herein.

In another aspect, the invention provides the use of a complex of formula (1) or a complex of formula (2) as a catalyst in carbon-heteroatom coupling reactions, wherein:
(a) the complex of formula (1) is:

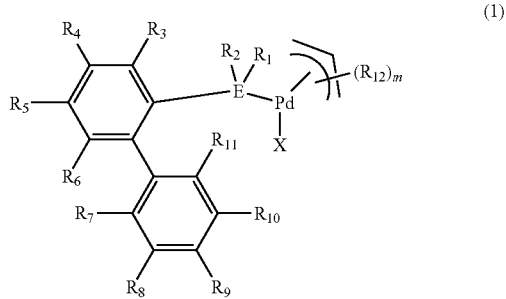

(1)

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or
$R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above;
$R_{12}$ is an organic group having 1-20 carbon atoms;
m is 0, 1, 2, 3, 4 or 5;
E is P or As; and
X is a coordinating anionic ligand;
and:
(b) the complex of formula (2) is as defined herein.

BRIEF DESCRIPTION OF THE DRAWINGS

The invention will now be described by way of the following non-limiting examples and with reference to the following figures in which.

DETAILED DESCRIPTION OF ILLUSTRATIVE EMBODIMENTS

Definitions

Figure 1:
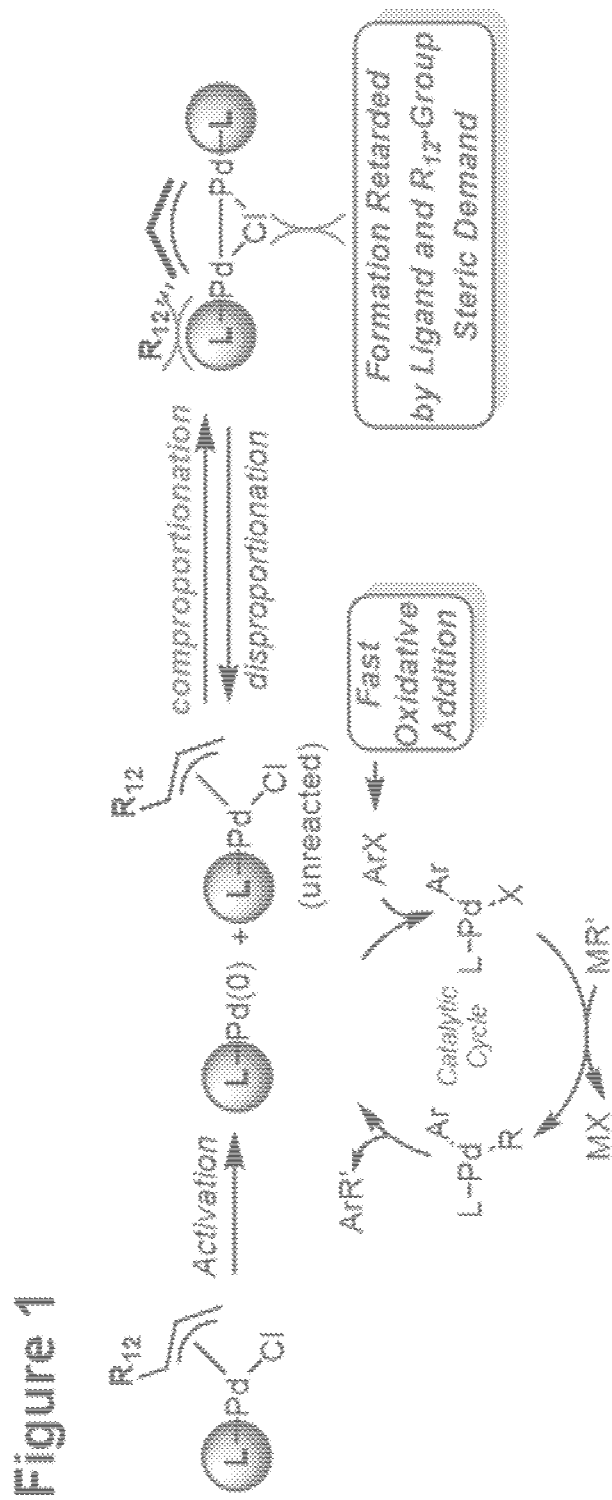
FIG. 1 illustrates some of the mechanisms set forth herein for a particular 7-allyl complex where L is a ligand of formula (4) or (5), X is chloro and m is 1.

The point of attachment of a moiety or substituent is represented by "-". For example, —OH is attached through the oxygen atom.

"Alkyl" refers to a straight-chain or branched saturated hydrocarbon group. In certain embodiments, the alkyl group may have from 1-20 carbon atoms, in certain embodiments from 1-15 carbon atoms, in certain embodiments, 1-8 carbon atoms. The alkyl group may be unsubstituted. Alternatively, the alkyl group may be substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, n-butyl, iso-butyl, sec-butyl, tert-butyl, n-pentyl, n-hexyl and the like.

The term "cycloalkyl" is used to denote a saturated carbocyclic hydrocarbon radical. The cycloalkyl group may have a single ring or multiple condensed rings. In certain embodiments, the cycloalkyl group may have from 3-15 carbon atoms, in certain embodiments, from 3-10 carbon atoms, in certain embodiments, from 3-8 carbon atoms. The cycloalkyl group may be unsubstituted. Alternatively, the cycloalkyl group may be substituted. Unless other specified, the cycloalkyl group may be attached at any suitable carbon atom and, if substituted, may be substituted at any suitable atom. Typical cycloalkyl groups include but are not limited to cyclopropyl, cyclobutyl, cyclopentyl, cyclohexyl and the like.

"Alkoxy" refers to an optionally substituted group of the formula alkyl-O— or cycloalkyl-O—, wherein alkyl and cycloalkyl are as defined above.

"Alkoxyalkyl" refers to an optionally substituted group of the formula alkoxy-alkyl-, wherein alkoxy and alkyl are as defined above.

"Aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-12 carbon atoms. The aryl group may be unsubstituted. Alternatively, the aryl group may be substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Arylalkyl" refers to an optionally substituted group of the formula aryl-alkyl-, where aryl and alkyl are as defined above.

"Coupling" refers to a chemical reaction in which two molecules or parts of a molecule join together (Oxford Dictionary of Chemistry, Sixth Edition, 2008).

"Halo" or "hal" refers to —F, —Cl, —Br and —I.

"Heteroalkyl" refers to a straight-chain or branched saturated hydrocarbon group wherein one or more carbon atoms are independently replaced with one or more heteroatoms (e.g. nitrogen, oxygen, phosphorus and/or sulfur atoms). The heteroalkyl group may be unsubstituted. Alternatively, the heteroalkyl group may be substituted. Unless otherwise specified, the heteroalkyl group may be attached at any suitable atom and, if substituted, may be substituted at any suitable atom. Examples of heteralkyl groups include but are not limited to ethers, thioethers, primary amines, secondary amines, tertiary amines and the like.

"Heterocycloalkyl" refers to a saturated cyclic hydrocarbon group wherein one or more carbon atoms are independently replaced with one or more heteroatoms (e.g. nitrogen, oxygen, phosphorus and/or sulfur atoms). The heterocycloalkyl group may be unsubstituted. Alternatively, the heterocycloalkyl group may be substituted. Unless otherwise specified, the heterocycloalkyl group may be attached at any suitable atom and, if substituted, may be substituted at any suitable atom. Examples of heterocycloalkyl groups include but are not limited to epoxide, morpholinyl, piperadinyl, piperazinyl, thirranyl, pyrrolidinyl, pyrazolidinyl, imidazolidinyl, thiazolidinyl, thiomorpholinyl and the like.

"Heteroaryl" refers to an aromatic carbocyclic group wherein one or more carbon atoms are independently replaced with one or more heteroatoms (e.g. nitrogen, oxygen, phosphorus and/or sulfur atoms). The heteroaryl group may be unsubstituted. Alternatively, the heteroaryl group may be substituted. Unless otherwise specified, the heteroaryl group may be attached at any suitable atom and, if substituted, may be substituted at any suitable atom. Examples of heteroaryl groups include but are not limited to thienyl, furanyl, pyrrolyl, imidazolyl, pyrazolyl, thiazolyl, isothiazolyl, oxazolyl, isoxazolyl, triazolyl, thiadiazolyl, thiophenyl, oxadiazolyl, pyridinyl, pyrimidyl, benzoxazolyl, benzthiazolyl, benzimidazolyl, indolyl, quinolinyl and the like.

"Substituted" refers to a group in which one or more hydrogen atoms are each independently replaced with substituents (e.g. 1, 2, 3, 4, 5 or more) which may be the same or different. Examples of substituents include but are not limited to -halo, —C(halo)$^a$, —R$^a$, =O, =S, —O—R$^a$, —S—R$^a$, —NR$^a$R$^b$, —CN, —NO$_2$, —C(O)—R$^a$, —COOR$^a$, —C(S)—R$^a$, —C(S)OR$^a$, —S(O)$_2$OH, —S(O)$_2$—R$^a$, —S(O)$_2$NR$^a$R$^b$, —O—S(O)—R$^a$ and —CONR$^a$R$^b$, such as -halo, —C(halo)$_3$ (e.g. —CF$_3$), —R$^a$, —O—R$^a$, —NR$^a$R$^b$, —CN, or —NO$_2$. R$^a$ and R$^b$ are independently selected from the groups consisting of H, alkyl, aryl, arylalkyl, heteroalkyl, heteroaryl, or R$^a$ and R$^b$ together with the atom to which they are attached form a heterocycloalkyl group. R$^a$ and R$^b$ may be unsubstituted or further substituted as defined herein.

"Thioalkyl" refers to an optionally substituted group of the formula alkyl-S— or cycloalkyl-S—, wherein alkyl and cycloalkyl are as defined above.

DETAILED DESCRIPTION

In one aspect, the present invention provides a palladium (II) complex of formula (1):

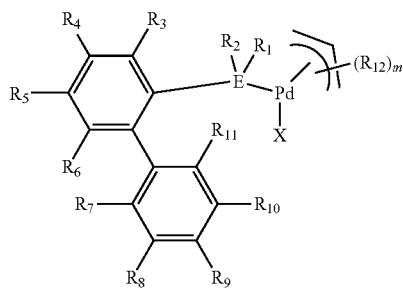

(1)

wherein:
R$_1$ and R$_2$ are independently organic groups having 1-20 carbon atoms, or R$_1$ and R$_2$ are linked to form a ring structure with E;
R$_3$, R$_4$, R$_5$, R$_6$, R$_7$, R$_8$, R$_9$, R$_{10}$ and R$_{11}$ are independently —H or organic groups having 1-20 carbon atoms; or
R$_1$/R$_3$ or R$_2$/R$_3$ forms a ring structure with the atoms to which they are attached and in this instance R$_4$/R$_5$, R$_5$/R$_6$, R$_7$/R$_8$, R$_8$/R$_9$, R$_9$/R$_{10}$ or R$_{10}$/R$_{11}$ may independently form a ring structure with the carbon atoms to which they are attached or R$_1$, R$_2$, R$_4$, R$_5$, R$_6$, R$_7$, R$_8$, R$_9$, R$_{10}$ and R$_{11}$ are as defined above;
R$_{12}$ is an organic group having 1-20 carbon atoms;
m is 0, 1, 2, 3, 4 or 5;
E is P or As; and
X is a coordinating anionic ligand;
provided that the palladium complex of formula (1) is not (π-crotyl)PdCl(dicyclohexylphosphino-2-biphenyl).

When E is a phosphorus atom (i.e. P), the complex of formula (1) is a palladium(II) complex comprising a monodentate biaryl tertiary phosphine ligand, a coordinating anionic ligand and an optionally substituted π-allyl group.

When E is an arsenic atom (i.e. As), the complex of formula (1) is a palladium(II) complex comprising a monodentate biaryl tertiary arsine ligand, a coordinating anionic ligand and an optionally substituted π-allyl group.

R$_1$ and R$_2$ may be the same or different. In one embodiment, R$_1$ and R$_2$ are the same. In another embodiment, R$_1$ and R$_2$ are different. R$_1$ and R$_2$ are selected up to the limitations imposed by stability and the rules of valence. R$_1$ and R$_2$ may be independently selected from the group consisting of substituted and unsubstituted straight-chain alkyl, substituted and unsubstituted branched-chain alkyl, substituted and unsubstituted cycloalkyl, substituted and unsubstituted aryl, and substituted and unsubstituted heteroaryl wherein the heteroatoms are independently selected from sulfur, nitrogen and oxygen. R$_1$ and R$_2$ may independently be substituted or unsubstituted branched- or straight-chain alkyl groups such as methyl, ethyl, n-propyl, iso-propyl, n-butyl, iso-butyl, sec-butyl, tert-butyl, pentyl (e.g. n-pentyl or neopentyl), hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more (e.g. 1, 2, 3, 4, or 5) substituents each of which may be the same or different such as halide (F, Cl, Br or I) or alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. C$_1$-C$_{10}$), alkoxy (e.g. C$_1$-C$_{10}$ alkoxy), straight- or branched-chain (dialkyl)amino (e.g. C$_1$-C$_{10}$ dialkyl)amino), heterocycloalkyl (e.g. C$_{3-10}$ heterocycloalkyl groups, such as morpholinyl and piperadinyl) or tri(halo)methyl (e.g. F$_3$C—). Suitable substituted aryl groups include but are not limited to 4-dimethylaminophenyl, 4-methylphenyl, 3,5-dimethylphenyl, 4-methoxyphenyl, 4-methoxy-3,5-dimethylphenyl and 3,5-di(trifluoromethyl)phenyl. Substituted or unsubstituted heteroaryl groups such as pyridyl may also be used. In an alternative embodiment, R$_1$ and R$_2$ are linked to form a ring structure with E, preferably 4- to 7-membered rings. Preferably, R$_1$ and R$_2$ are the same and are tert-butyl, cyclohexyl, phenyl or substituted phenyl groups, such as 3,5-di(trifluoromethyl)phenyl.

$R_1$ and $R_2$ may be independently selected from the group consisting of -Me, -Et, -$^n$Pr, -$^i$Pr, -$^n$Bu, -$^i$Bu, cyclohexyl and cycloheptyl.

$R_3$, $R_4$, $R_5$, $R_6$, $R_7$, $R_8$, $R_9$, $R_{10}$ and $R_{11}$ are independently —H or organic groups having 1-20 carbon atoms. $R_3$, $R_4$, $R_5$, $R_6$, $R_7$, $R_8$, $R_9$, $R_{10}$ and $R_{11}$ are selected up to the limitations imposed by stability and the rules of valence. $R_3$, $R_4$, $R_5$ and $R_6$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different) and substituted and unsubstituted heterocycloalkyl groups. The heteroatoms in the heteryl or heterocycloalkyl groups may be independently selected from sulfur, nitrogen and/or oxygen. In one embodiment, the alkyl groups may be optionally substituted with one or more (e.g. 1, 2, 3, 4, or 5) substituents each of which may be the same or different such as halide (F, Cl, Br or I), alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. ($C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. Suitable unsubstituted —N(alkyl)$_2$ groups include but are not limited to —NMe$_2$, -NEt$_2$ and —NPr$_2$ (n- or i-). A suitable unsubstituted —N(cycloalkyl)$_2$ group includes but is not limited to —N(Cy)$_2$. Suitable substituted —N(alkyl)$_2$ groups include but are not limited to —N(CH$_2$CH$_2$Me)$_2$ and —N(CF$_3$)$_2$. Suitable unsubstituted —N(aryl)$_2$ groups include but are not limited to —NPh$_2$. Suitable substituted —N(aryl)$_2$ groups include but are not limited to —N(2-, 3- or 4-dimethylaminophenyl)$_2$, —N(2-, 3- or 4-methylphenyl)$_2$, —N(2,3- or 3,5-dimethylphenyl)$_2$, —N(2-, 3- or 4-methoxypheny)$_2$ and —N(4-methoxy-3,5-dimethylphenyl)$_2$. Suitable unsubstituted —N(heteroaryl)$_2$ groups include but are not limited to —N(furyl)$_2$ and —N(pyridyl)$_2$. Substituted and unsubstituted heterocycloalkyl groups include but are not limited to $C_{4-8}$-heterocycloalkyl groups, such as piperidinyl and morpholinyl.

$R_3$, $R_4$, $R_5$ and $R_6$ may be independently selected from the group consisting of —H, unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(ary)$_2$ (wherein the aryl groups may be the same or different). Branched- or straight-chain alkyl groups may include groups such as methyl, ethyl, n-propyl, iso-propyl, n-butyl, iso-butyl, sec-butyl, tert-butyl, pentyl (e.g. n-pentyl or neopentyl), hexyl, heptyl, octyl, nonyl, decyl, dodecyl or stearyl. Cycloalkyl groups may include groups such as cyclopropyl, cyclobutyl, cyclopentyl, cyclohexyl or adamantyl. Alkoxy groups may include groups such as methoxy (—OMe), ethoxy (—OEt), n-propoxy (—O-n-Pr), iso-propoxy (—O-i-Pr), n-butoxy (—O-n-Bu), iso-butoxy (—O-i-Bu), sec-butoxy (—O-s-Bu), tert-butoxy (—O-t-Bu), —O-pentyl, —O-hexyl, —O-heptyl, —O-octyl, —O-nonyl, —O-decyl, —O-dodecyl. —N(alkyl)$_2$ groups may include groups such as —NMe$_2$, -NEt$_2$, —N(n-Pr)$_2$ or —N(i-Pr)$_2$.

$R_3$, $R_4$, $R_5$ and $R_6$ may be independently selected from the group consisting of —H, unsubstituted —N(alkyl)$_2$ (wherein the alkyl groups may be the same or different and may be independently selected from straight-chain or branched-chain, groups) and unsubstituted —N(aryl)$_2$ (wherein the aryl groups may be the same or different).

$R_3$, $R_4$, $R_5$ and $R_6$ may be independently selected from the group consisting of —H, unsubstituted straight-chain alkyl, unsubstituted branched-chain alkyl, unsubstituted cycloalkyl and unsubstituted alkoxy.

In one embodiment, each of $R_3$, $R_4$, $R_5$ and $R_6$ are —H.

In another embodiment, at least one of $R_3$, $R_4$, $R_5$ and $R_6$ is selected from a group which is not —H. For example, one of $R_3$, $R_4$, $R_5$ and $R_6$ may be selected from a group which is not —H, such as two of $R_3$, $R_4$, $R_5$ and $R_6$, three of $R_3$, $R_4$, $R_5$ and $R_6$ or all of $R_3$, $R_4$, $R_5$ and $R_6$.

In another embodiment, two of $R_3$, $R_4$, $R_5$ and $R_5$ are —H, and the other two of $R_3$, $R_4$, $R_5$ and $R_6$ are independently selected from the group consisting of unsubstituted straight-chain alkyl, unsubstituted branched-chain alkyl, unsubstituted cycloalkyl and unsubstituted alkoxy. In another embodiment, two of $R_3$, $R_4$, $R_5$ and $R_6$ are —H (e.g. $R_4$ and $R_5$), and the other two of $R_3$, $R_4$, $R_5$ and $R_6$ (e.g. $R_3$ and $R_6$) are independently selected from the group consisting of $C_{1-5}$-alkyl and —O—$C_{1-5}$-alkyl, such as -Me, -Et, —Pr (n- or i-), -Bu (n-, i- or t-), —OMe, -OEt, —OPr (n- or i-) and —OBu (n-, i- or t-), for example, -Me, -Et, —OMe and —OEt.

In another embodiment, two of $R_3$, $R_4$, $R_5$ and $R_6$ are —H (e.g. $R_4$ and $R_5$), and the other two of $R_3$, $R_4$, $R_5$ and $R_6$ (e.g. $R_3$ and $R_6$) are selected from the group consisting of unsubstituted straight-chain alkyl, unsubstituted branched-chain alkyl, unsubstituted cycloalkyl and unsubstituted alkoxy. In a preferred embodiment, two of $R_3$, $R_4$, $R_5$ and $R_6$ are —H, and the other two of $R_3$, $R_4$, $R_5$ and $R_6$ are selected from the group consisting of $C_{1-5}$-alkyl and —O—$C_{1-5}$-alkyl, such as -Me, -Et, —Pr (n- or i-), -Bu (n-, i- or t-), —OMe, —OEt, —OPr (n- or i-) and —OBu (n-, i- or t-), for example, -Me, -Et, —OMe and —OEt. In one particularly preferred embodiment, $R_4$ and $R_5$ are —H, and $R_3$ and Re are —OMe.

$R_7$, $R_8$, $R_9$, $R_{10}$ and $R_{11}$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different) and substituted and unsubstituted heterocycloalkyl groups. The heteroatoms in the heteroaryl or heterocycloalkyl groups may be independently selected from sulfur, nitrogen or/and oxygen. In one embodiment, the alkyl groups may be optionally substituted with one or more (e.g. 1, 2, 3, 4, or 5) substituents each of which may be the same or different such as halide (F, Cl, Br or I), alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. Suitable unsubstituted —N(alkyl)$_2$ groups include but are not limited to —NMe$_2$, -NEt$_2$ and —NPr$_2$ (n- or i-). A suitable unsubstituted —N(cycloalkyl)$_2$ group includes but is not limited to —N(Cy)$_2$. Suitable substituted —N(alkyl)$_2$ groups include but are not limited to —N(CH$_2$CH$_2$OMe)$_2$ and —N(CF$_3$)$_2$. Suitable unsubstituted —N(aryl)$_2$ groups include but are not limited to —NPh$_2$. Suitable substituted —N(aryl)$_2$ groups include but are not limited to —N(2-, 3- or 4-dimethylaminophenyl)$_2$, —N(2-, 3- or 4-methylphenyl)$_2$, —N(2,3- or 3,5-dimethylphenyl)$_2$, —N(2-, 3- or 4-methoxyphenyl)$_2$ and —N(4-methoxy-3,5-dimethylphenyl)$_2$. Suitable unsubstituted —N(heteroaryl)$_2$ groups include but are not limited to —N(furyl)$_2$ and —N(pyridyl)$_2$. Substituted and unsubstituted heterocycloalkyl groups include $C_{4-8}$-heterocycloalkyl groups, such as piperidinyl and morpholinyl.

$R_7$, $R_8$, $R_9$, $R_{10}$ and $R_{11}$ may be independently selected from the group consisting of —H, unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different). Branched- or straight-chain alkyl groups may include groups such as methyl, ethyl, n-propyl, iso-propyl, n-butyl, iso-butyl, sec-butyl, tert-butyl, pentyl (e.g. n-pentyl or neopentyl), hexyl, heptyl, octyl, nonyl, decyl, dodecyl or stearyl. Cycloalkyl groups may include groups such as cyclopropyl, cyclobutyl, cyclopentyl, cyclohexyl or adamantyl. Alkoxy groups may include groups such as methoxy (—OMe), ethoxy (—OEt), n-propoxy (—O-n-Pr), iso-propoxy (—O-i-Pr), n-butoxy (—O-n-Bu), iso-butoxy (—O-i-Bu), sec-butoxy (—O-s-Bu), tert-butoxy (—O-t-Bu), —O-pentyl, —O-hexyl, —O-heptyl, —O-octyl, —O-nonyl, —O-decyl, —O-dodecyl. —N(alkyl)$_2$ groups may include groups such as —NMe$_2$, -NEt$_2$, —N(n-Pr)$_2$ or —N(i-Pr)$_2$.

$R_7$, $R_8$, $R_9$, $R_{10}$ and $R_{11}$ may be independently selected from the group consisting of —H, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

$R_7$, $R_8$, $R_9$, $R_{10}$ and $R_{11}$ may be independently selected from the group consisting of —H, unsubstituted straight-chain alkyl, unsubstituted branched-chain alkyl, unsubstituted cycloalkyl and unsubstituted alkoxy.

In another embodiment, at least one of $R_7$, $R_8$, $R_9$, $R_{10}$ and $R_{11}$ is selected from a group which is not —H. For example, one of $R_7$, $R_8$, $R_9$, $R_{10}$ and $R_{11}$ may be selected from a group a group which is not —H, such as two of $R_7$, $R_8$, $R_9$, $R_{10}$ and $R_{11}$ (e.g. $R_7$ and $R_{11}$), three of $R_7$, $R_8$, $R_9$, $R_{10}$ and $R_{11}$ (e.g. $R_7$, $R_9$ and $R_{11}$), four of $R_7$, $R_8$, $R_9$, $R_{10}$ and $R_{11}$ or all of $R_7$, $R_8$, $R_9$, $R_{10}$ and $R_{11}$.

In one embodiment, each of $R_7$, $R_8$, $R_9$, $R_{10}$ and $R_{11}$ are —H.

In another embodiment, four of $R_7$, $R_8$, $R_9$, $R_{10}$ and $R_{11}$ are —H (e.g. $R_8$, $R_9$, $R_{10}$ and $R_{11}$), and the other one of $R_7$, $R_8$, $R_9$, $R_{10}$ and $R_{11}$ (e.g. $R_7$) is selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In another embodiment, four of $R_7$, $R_8$, $R_9$, $R_{10}$ and $R_{11}$ are —H (e.g. $R_8$, $R_9$, $R_{10}$ and $R_{11}$), and the other one of $R_7$, $R_8$, $R_9$, $R_{10}$ and $R_{11}$ (e.g. $R_7$) is selected from the group consisting of $C_{1-5}$-alkyl, —O—$C_{1-5}$-alkyl and —N($C_{1-5}$-alkyl)$_2$ such as -Me, -Et, —Pr (n- or i-), -Bu (n-, i- or t-), —OMe, —OEt, —OPr (n- or i-), —OBu (n-, i- or t-), —NMe$_2$, -NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, -NEt$_2$. For example, $R_8$, $R_9$, $R_{10}$ and $R_{11}$ are —H, and $R_7$ is selected from $C_{1-5}$-alkyl, —O—$C_{1-5}$-alkyl and —N($C_{1-5}$-alkyl)$_2$ groups, such as those described above. In another embodiment, $R_8$, $R_9$, $R_{10}$ and $R_{11}$ are —H, and $R_7$ is selected from the group consisting of —OMe, —O-i-Pr, —NMe$_2$, -NEt$_2$, —N(n-Pr)$_2$ and —N(i-Pr)$_2$, such as —OMe and —NMe$_2$.

In another embodiment, three of $R_7$, $R_8$, $R_9$, $R_{10}$ and $R_{11}$ are —H (e.g. $R_8$, $R_9$ and $R_{10}$), and the other two of $R_7$, $R_8$, $R_9$, $R_{10}$ and $R_{11}$ (e.g. $R_7$ and $R_{11}$) are independently selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In one embodiment, three of $R_7$, $R_8$, $R_9$, $R_{10}$ and $R_{11}$ are —H (e.g. $R_8$, $R_9$ and $R_{10}$), and the other two of $R_7$, $R_8$, $R_9$, $R_{10}$ and $R_{11}$ (e.g. $R_7$ and $R_{11}$) are selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In another embodiment, three of $R_7$, $R_8$, $R_9$, $R_{10}$ and $R_{11}$ are —H (e.g. $R_8$, $R_9$ and $R_{10}$), and the other two of $R_7$, $R_8$, $R_9$, $R_{10}$ and $R_{11}$ (e.g. $R_7$ and $R_{11}$) are independently selected from the group consisting of $C_{1-5}$-alkyl, —O—$C_{1-5}$-alkyl and —N($C_{1-5}$-alkyl)$_2$ such as -Me, -Et, —Pr (n- or i-), -Bu (n-, i- or t-), —OMe, —OEt, —OPr (n- or i-), —OBu (n-, i- or t-), —NMe$_2$, -NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, -NEt$_2$. For example, $R_8$, $R_9$ and $R_{10}$ are —H, and $R_7$ and $R_{11}$ are independently selected from $C_{1-5}$-alkyl, —O—$C_{1-5}$-alkyl and —N($C_{1-5}$-alkyl)$_2$ groups, such as those described above. In another embodiment, $R_8$, $R_9$ and $R_{10}$ are —H, and $R_7$ and $R_{11}$ are independently selected from the group consisting of —OMe, —O-i-Pr, —NMe$_2$, -NEt$_2$, —N(n-Pr)$_2$ and —N(i-Pr)$_2$, such as —OMe and —O-i-Pr.

In a preferred embodiment, three of R$_7$, R$_8$, R$_9$, R$_{10}$ and R$_{11}$ are —H (e.g. R$_8$, R$_9$ and R$_{10}$), and the other two of R$_7$, R$_8$, R$_9$, R$_{10}$ and R$_{11}$ (e.g. R$_7$ and R$_{11}$) are selected from the group consisting of C$_{1-5}$-alkyl, —O—C$_{1-5}$-alkyl and —N(C$_{1-5}$-alkyl)$_2$ such as -Me, -Et, —Pr (n- or i-), -Bu (n-, i- or t-), —OMe, —OEt, —OPr (n- or i-), —OBu (n-, i- or t-), —NMe$_2$, -NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, -NEt$_2$. In a particularly preferred embodiment, R$_8$, R$_9$ and R$_{10}$ are —H, and R$_7$ and R$_{11}$ are independently selected from C$_{1-5}$-alkyl, —O—C$_{1-5}$-alkyl and —N(C$_{1-5}$-alkyl)$_2$ groups, such as those described above. In an especially preferred embodiment, R$_8$, R$_9$ and R$_{10}$ are —H, and R$_7$ and R$_{11}$ are selected from the group consisting of —OMe, —O-i-Pr, —NMe$_2$, -NEt$_2$, —N(n-Pr)$_2$ and —N(i-Pr)$_2$, such as —OMe and —O-i-Pr.

In another embodiment, two of R$_7$, R$_8$, R$_9$, R$_{10}$ and R$_{11}$ are —H (e.g. R$_8$ and R$_{10}$), and the other three of R$_7$, R$_8$, R$_9$, R$_{10}$ and R$_{11}$ (e.g. R$_7$, R$_9$ and R$_{11}$) are independently selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In another embodiment, two of R$_7$, R$_8$, R$_9$, R$_{10}$ and R$_{11}$ are —H (e.g. R$_8$ and R$_{10}$), and the other three of R$_7$, R$_8$, R$_9$, R$_{10}$ and R$_{11}$ (e.g. R$_7$, R$_9$ and R$_{11}$) are selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and may be independently selected from straight-chain or branched-chain groups) and unsubstituted —N(aryl)$_2$ (wherein the aryl groups may be the same or different).

In one preferred embodiment, two of R$_7$, R$_8$, R$_9$, R$_{10}$ and R$_{11}$ are —H (e.g. R$_8$ and R$_{10}$), and the other three of R$_7$, R$_8$, R$_9$, R$_{10}$ and R$_{11}$ (e.g. R$_7$, R$_9$ and R$_{11}$) are independently selected from the group consisting of C$_{1-5}$-alkyl, —O—C$_{1-5}$-alkyl and —N(C$_{1-5}$-alkyl)$_2$, such as -Me, -Et, —Pr (n- or i-), -Bu (n-, i- or t-), —OMe, —OEt, —OPr (n- or i-), —OBu (n-, i- or t-), —NMe$_2$, -NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, -NEt$_2$. In a particularly preferred embodiment, R$_8$ and R$_{10}$ are —H, and R$_7$, R$_9$ and R$_{11}$ are independently selected from —C$_{1-5}$-alkyl groups, such as those described above.

In another preferred embodiment, two of R$_7$, R$_8$, R$_9$, R$_{10}$ and R$_{11}$ are —H (e.g. R$_8$ and R$_{10}$), and the other three of R$_7$, R$_8$, R$_9$, R$_{10}$ and R$_{11}$ (e.g. R$_7$, R$_9$ and R$_{11}$) are selected from the group consisting of C$_{1-5}$-alkyl, —O—C$_{1-5}$-alkyl and —N(C$_{1-5}$-alkyl)$_2$, such as -Me, -Et, —Pr (n- or i-), -Bu (n-, i- or t-), —OMe, —OEt, —OPr (n- or i-), —OBu (n-, i- or t-), —NMe$_2$, -NEt$_2$, —N(n-Pr)$_2$ or —N(i-Pr)$_2$, for example, -Me, -Et, -n-Pr, -i-Pr, —OMe, —OEt, —O-n-Pr, —O-i-Pr, —NMe$_2$, -NEt$_2$. In a particularly preferred embodiment, R$_8$ and R$_{10}$ are —H, and R$_7$, R$_9$ and R$_{11}$ are independently selected from —C$_{1-5}$-alkyl groups, such as those described above. In an especially preferred embodiment, R$_8$ and R$_{10}$ are —H, and R$_7$, R$_8$ and R$_{11}$ are -i-Pr.

In one embodiment, the monodentate tertiary phosphine ligand is selected from the group consisting of:

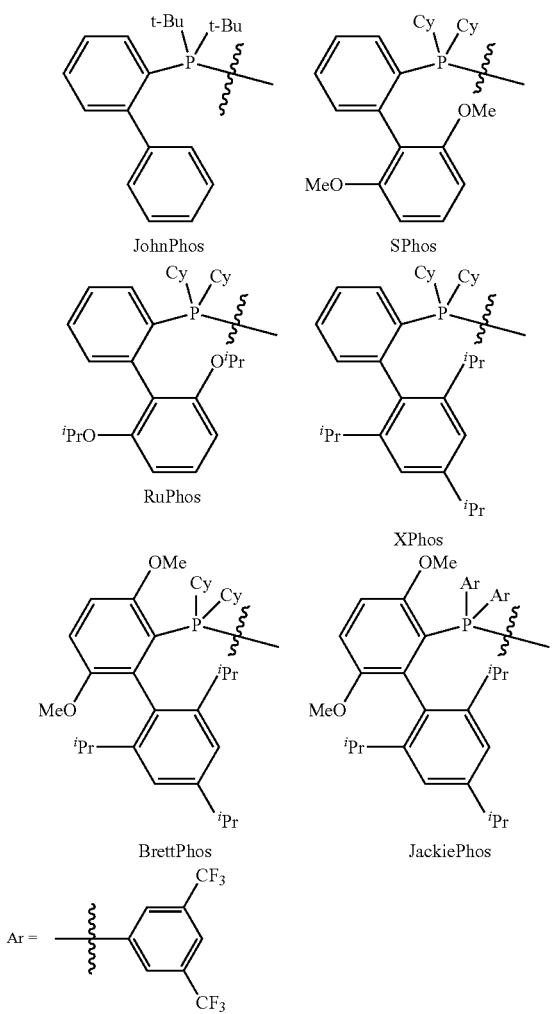

R$_1$/R$_3$ or R$_2$/R$_3$ may form a ring structure with the atoms to which they are attached and in this instance R$_4$/R$_5$, R$_5$/R$_6$, R$_7$/R$_8$, R$_8$/R$_9$, R$_9$/R$_{10}$ or R$_{10}$/R$_{11}$ independently form a ring structure with the carbon atoms to which they are attached or R$_1$, R$_2$, R$_4$, R$_5$, R$_6$, R$_7$, R$_8$, R$_9$, R$_{10}$ and R$_{11}$ are as defined above. The pair or pairs are selected up to the limitations imposed by stability and the rules of valence.

The linking group for R$_1$/R$_3$ or R$_2$/R$_3$ may be a substituted or unsubstituted alkyl, substituted or unsubstituted alkoxy, or substituted or unsubstituted heteroalkyl. The ring structure formed from the pair or pairs selected from the group consisting of R$_4$/R$_5$, R$_5$/R$_6$, R$_7$/R$_8$, R$_8$/R$_9$, R$_9$/R$_{10}$ and R$_{10}$/R$_{11}$ may be a substituted or unsubstituted cycloalkyl, substituted or unsubstituted heterocycloalkyl, substituted or unsubstituted aryl or substituted or unsubstituted heteroaryl group. R$_1$ and R$_2$ may be independently selected from the groups defined above when they do not form a ring structure with R$_3$.

In one embodiment, R$_4$, R$_5$ and R$_6$ are —H and the pair R$_1$/R$_3$ or R$_2$/R$_3$ forms a ring structure with the atoms to which they are attached. In another embodiment, R$_4$, R$_5$ and R$_6$ are —H and the pair R$_1$/R$_3$ or R$_2$/R$_3$ forms a ring structure with the atoms to which they are attached. In either of these instances, $R_7/R_8$, $R_8/R_9$, $R_9/R_{10}$ or $R_{10}/R_{11}$ may independently form a ring structure with the carbon atoms to which they are attached or $R_7$, $R_8$, $R_9$, $R_{10}$ and $R_{11}$ are as defined above. $R_1/R_3$ or $R_2/R_3$ may form a ring structure selected from the group consisting of:

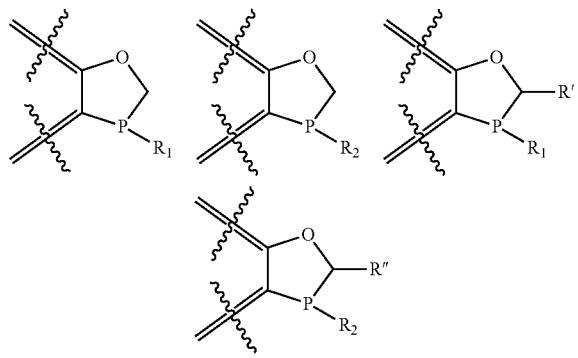

wherein:

$R_1$ and $R_2$ are as defined above: and

R' and R" are independently as defined above for $R_1$ and $R_2$.

In one embodiment, R' and R" are independently selected from the group consisting of methyl, propyl (n- or i-), butyl (n-, i- or t-), cyclohexyl or phenyl.

Examples of phosphorus ligands include those described by Tang et al, Angew. Chem. Int. Ed. 2010, 49, 5879-5883, Zhao et al, Chem. Eur. J, 2013, 19(7), 2261-2265 and Xu et al, Journal of the American Chemical Society, 2014, 136(2), 570-573 such as:

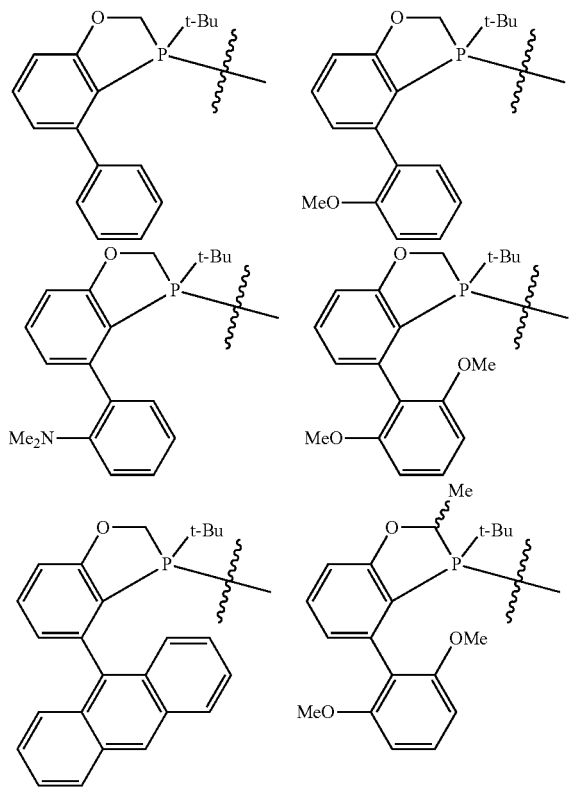

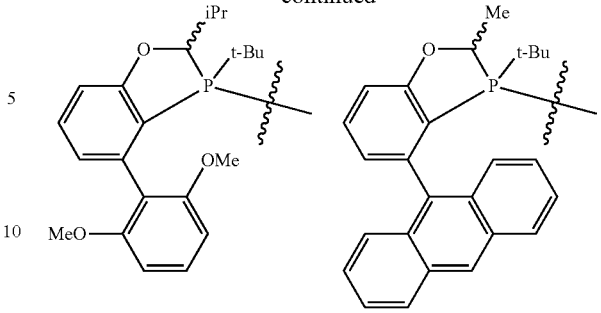

It will be understood that, in the depictions herein, where -Me or -$^i$Pr is connected by a wavy line (∿), either stereoisomer may be present.

The Pd atom in the complex of formula (1) is coordinated to an optionally substituted allyl group. $R_{12}$ is an organic group having 1-20 carbon atoms, preferably 1-10 carbon atoms and more preferably 1-8 carbon atoms. $R_{12}$ is selected up to the limitations imposed by stability and the rules of valence. The number of $R_{12}$ groups ranges from 0 to 5 i.e. m is 0, 1, 2, 3, 4 or 5. When m is 2, 3, 4 or 5, each of $R_{12}$ may be the same or different. In certain embodiments, when m is 2, 3, 4, or 5, each $R_{12}$ is the same. In certain embodiments, m is 0 i.e. the allyl group is unsubstituted. In certain embodiments, m is 1. In certain embodiments, m is 2, wherein each $R_{12}$ is the same or different.

$R_{12}$ may be selected from the group consisting of substituted and unsubstituted straight-chain alkyl, substituted and unsubstituted branched-chain alkyl, substituted and unsubstituted cycloalkyl, substituted and unsubstituted aryl, and substituted and unsubstituted heteroaryl wherein the heteroatoms are independently selected from sulfur, nitrogen and oxygen. In one embodiment, $R_{12}$ is selected from the group consisting of substituted and unsubstituted straight-chain alkyl, substituted and unsubstituted branched-chain alkyl, and substituted and unsubstituted cycloalkyl. In another embodiment, $R_{12}$ is selected from the group consisting of substituted and unsubstituted aryl, and substituted and unsubstituted heteroaryl wherein the heteroatoms are independently selected from sulfur, nitrogen and oxygen. $R_{12}$ may be substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantyl or aryl groups such as phenyl, naphthyl or anthracyl. In one embodiment, the alkyl groups may be optionally substituted with one or more (e.g. 1, 2, 3, 4, or 5) substituents each of which may be the same or different such as halide (F, Cl, Br or I), alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. In one embodiment, each $R_{12}$ is independently a methyl, phenyl or substituted phenyl group.

Suitable optionally substituted allyl groups as coordinated to the Pd atom are shown below:

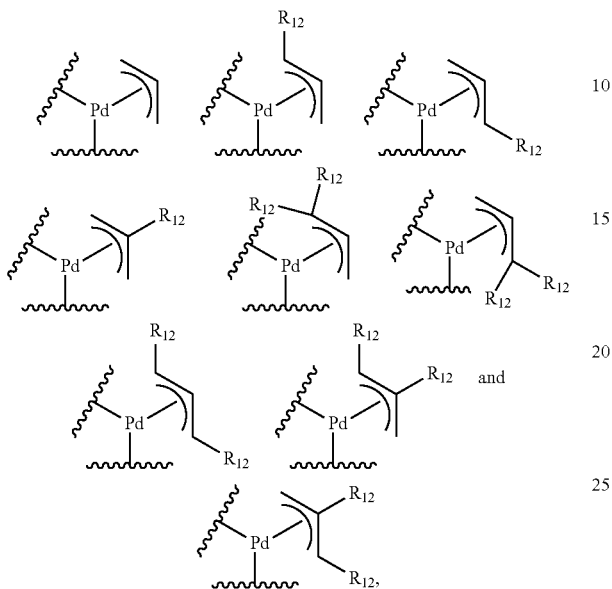

such as

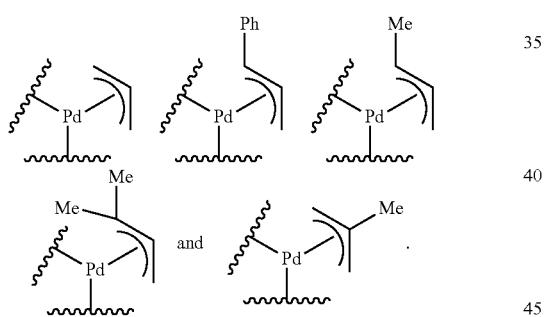

In the complex of formula (1), X is a coordinated anionic ligand i.e. the anionic ligand is bonded to the Pd atom within the coordination sphere. In one embodiment, X is a halo group, preferably, $C_1$, Br, I, and more preferably, $C_1$. In another embodiment, X is trifluoroacetate (i.e. $F_3CCO_2^-$).

The complex of formula (1) may be selected from the group consisting of:

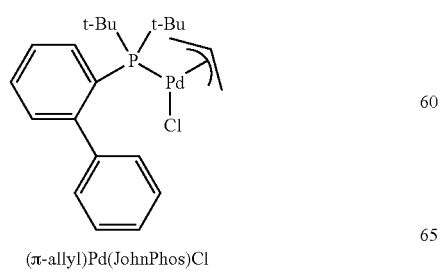

(π-allyl)Pd(JohnPhos)Cl

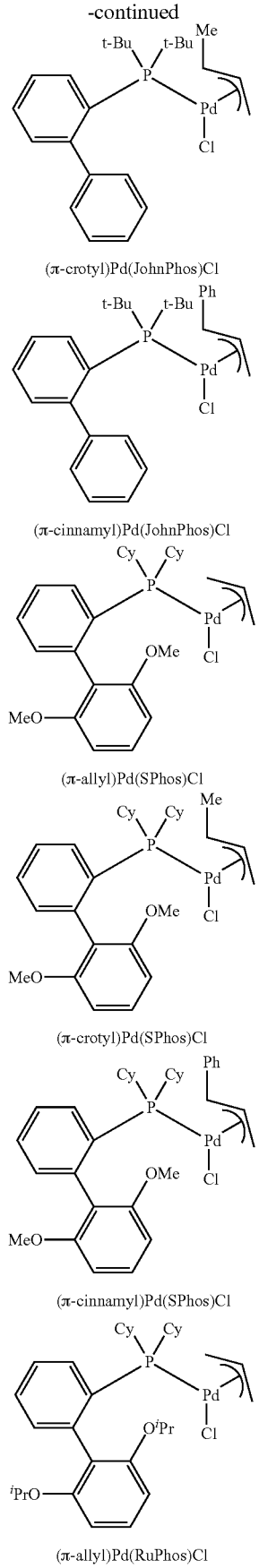

(π-crotyl)Pd(JohnPhos)Cl (π-cinnamyl)Pd(JohnPhos)Cl (π-allyl)Pd(SPhos)Cl (π-crotyl)Pd(SPhos)Cl (π-cinnamyl)Pd(SPhos)Cl (π-allyl)Pd(RuPhos)Cl -continued
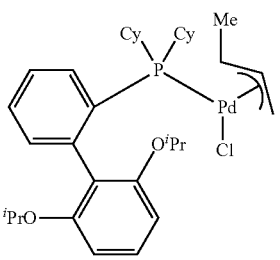
(π-crotyl)Pd(RuPhos)Cl
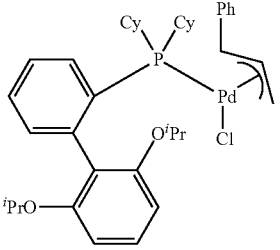
(π-cinnamyl)Pd(RuPhos)Cl
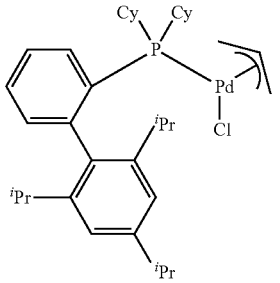
(π-allyl)Pd(XPhos)Cl
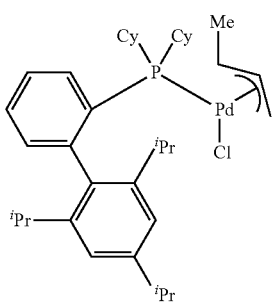
(π-crotyl)Pd(XPhos)Cl
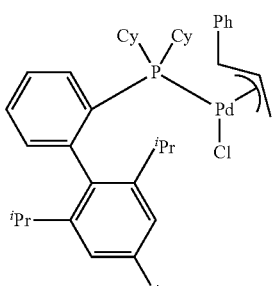
(π-cinnamyl)Pd(XPhos)Cl
-continued
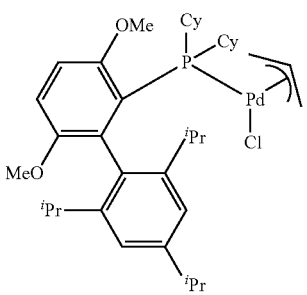
(π-allyl)Pd(BrettPhos)Cl
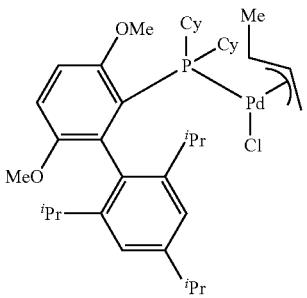
(π-crotyl)Pd(BrettPhos)Cl
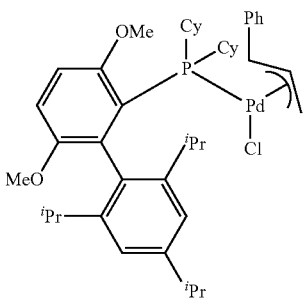
(π-cinnamyl)Pd(BrettPhos)Cl
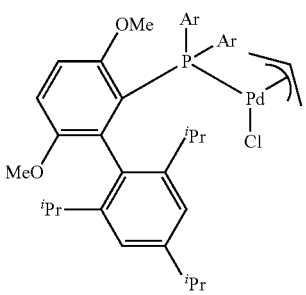
(π-allyl)Pd(JackiePhos)Cl
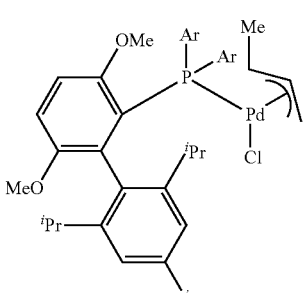
(π-crotyl)Pd(JackiePhos)Cl

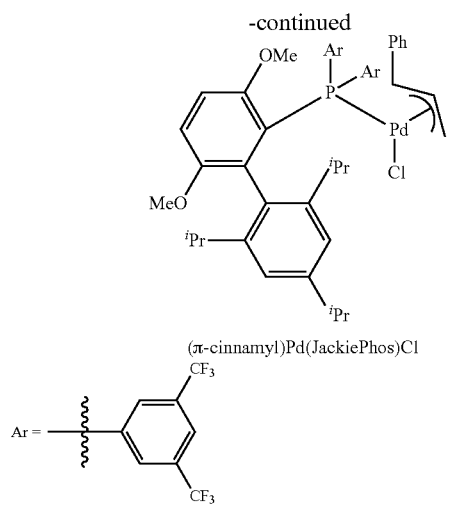

(π-cinnamyl)Pd(JackiePhos)Cl

In another aspect, the present invention provides a palladium complex of formula (2):

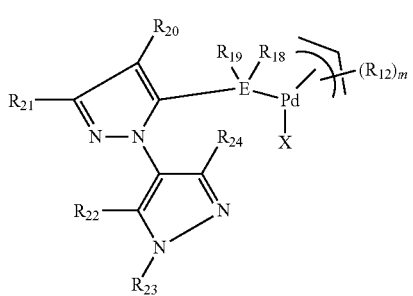

wherein:
$R_{18}$ and $R_{19}$ are independently selected from the group consisting of -Me, -Et, -$^n$Pr, -$^i$Pr, -$^n$Bu, -$^i$Bu, cyclohexyl and cycloheptyl;
$R_{12}$ is an organic group having 1-20 carbon atoms;
$R_{20}$, $R_{21}$, $R_{22}$, $R_{23}$ and $R_{24}$ are independently —H or organic groups having 1-20 carbon atoms; or one or both pairs selected from $R_{20}/R_{21}$ or $R_{22}/R_{23}$ may independently form a ring structure with the atoms to which they are attached;
m is 0, 1, 2, 3, 4 or 5; and
X is a coordinating anionic ligand.

The complex of formula (2) is a palladium(II) complex comprising a monodentate bi-heteroaryl tertiary phosphine ligand, a coordinating anionic ligand and an optionally substituted π-allyl group.

$R_{12}$, m and X are as described above.

$R_{18}$ and $R_{19}$ are independently selected from the group consisting of -Me, -Et, -$^n$Pr, -$^i$Pr, -$^n$Bu, -$^i$Bu and cyclohexyl. $R_{18}$ and $R_{19}$ are selected up to the limitations imposed by stability and the rules of valence. $R_{18}$ and $R_{19}$ may the same. Alternatively, $R_{18}$ and $R_{19}$ may different. In one preferred embodiment, $R_{18}$ and $R_{19}$ are the same and are cyclohexyl groups.

$R_{20}$, $R_{21}$, $R_{22}$, $R_{23}$ and $R_{24}$ are independently —H or organic groups having 1-20 carbon atoms. $R_{20}$, $R_{21}$, $R_{22}$, $R_{23}$ and $R_{24}$ are selected up to the limitations imposed by stability and the rules of valence. $R_{20}$ and $R_{21}$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different) and substituted and unsubstituted heterocycloalkyl groups. The heteroatoms in the heteroaryl or heterocycloalkyl groups may be independently selected from sulfur, nitrogen or/and oxygen. In one embodiment, the alkyl groups may be optionally substituted with one or more (e.g. 1, 2, 3, 4, or 5) substituents each of which may be the same or different such as halide (F, Cl, Br or I) e.g. —CF$_3$, alkoxy groups, e.g. methoxy, ethoxy or propoxy. The aryl group may be optionally substituted with one or more (e.g. 1, 2, 3, 4, or 5) substituents each of which may be the same or different such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. F$_3$C—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. Suitable unsubstituted —N(alkyl)$_2$ groups include but are not limited to —NMe$_2$, -NEt$_2$ and —NPr$_2$ (n- or i-). A suitable unsubstituted —N(cycloalkyl)$_2$ group includes but is not limited to —N(Cy)$_2$. Suitable substituted —N(alkyl)$_2$ groups include but are not limited to —N(CH$_2$CH$_2$OMe)$_2$ and —N(CF$_3$)$_2$. Suitable unsubstituted —N(aryl)$_2$ groups include but are not limited to —NPh$_2$. Suitable substituted —N(aryl)$_2$ groups include but are not limited to —N(2-, 3- or 4-dimethylaminophenyl)$_2$, —N(2-, 3- or 4-methylphenyl)$_2$, —N(2,3- or 3,5-dimethylphenyl)$_2$, —N(2-, 3- or 4-methoxyphenyl)$_2$ and —N(4-methoxy-3,5-dimethylphenyl)$_2$. Suitable unsubstituted —N(heteroaryl)$_2$ groups include but are not limited to —N(furyl)$_2$ and —N(pyridyl)$_2$. Substituted and unsubstituted heterocycloalkyl groups include $C_{4-8}$-heterocycloalkyl groups, such as piperidinyl and morpholinyl.

In one preferred embodiment, both of $R_{20}$ and $R_{21}$ are —H.

$R_{22}$ and $R_{24}$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted -thioalkyl, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different). The heteroatoms in the heteroaryl groups may be independently selected from sulfur, nitrogen or/and oxygen. In one embodiment, the alkyl groups may be optionally substituted with one or more (e.g. 1, 2, 3, 4, or 5) substituents such as halide (F, Cl, Br or I), alkoxy groups, e.g. methoxy, ethoxy or propoxy. The aryl group may be optionally substituted with one or more (e.g. 1, 2, 3, 4, or 5) substituents such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. Substituted or unsubstituted -thioalkyl groups include —$S(C_{1-5}$-alkyl), such as —SMe, -SEt, —SPr (n- or i-). In one embodiment, both of $R_{22}$ and $R_{24}$ are phenyl.

$R_{23}$ may be independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, and substituted and unsubstituted heteroaryl. The heteroatoms in the heteroaryl groups may be independently selected from sulfur, nitrogen or/and oxygen. In one embodiment, the alkyl groups may be optionally substituted with one or more (e.g. 1, 2, 3, 4, or 5) substituents such as halide (F, Cl, Br or I), alkoxy groups, e.g. methoxy, ethoxy or propoxy. The aryl group may be optionally substituted with one or more (e.g. 1, 2, 3, 4, or 5) substituents such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. ($C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. In one embodiment, $R_{23}$ is phenyl.

In one preferred embodiment, each of $R_{22}$, $R_{23}$ and $R_{24}$ are phenyl groups.

In one embodiment, the monodentate bi-heteroaryl tertiary phosphine ligand is selected from the group consisting of:

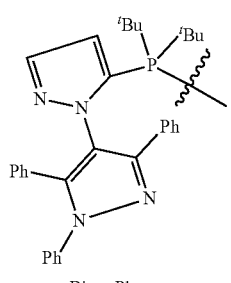
BippyPhos

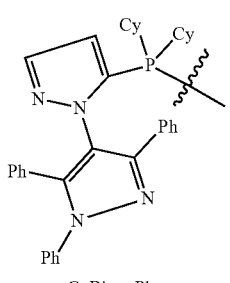
CyBippyPhos

The complex of formula (2) may be selected from the group consisting of:

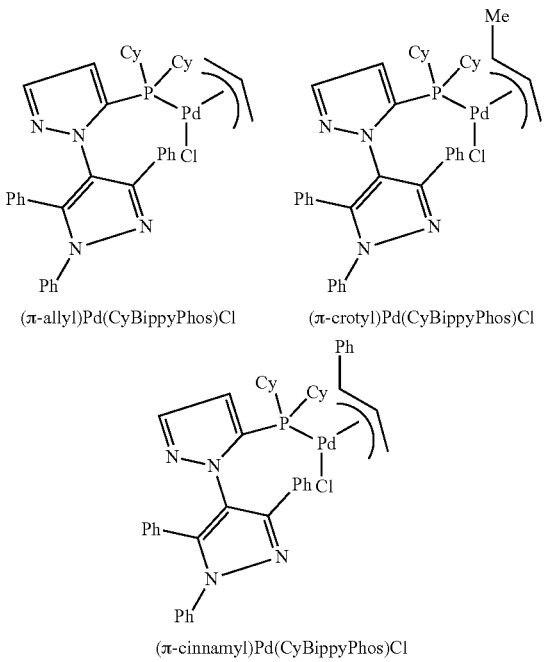

(π-allyl)Pd(CyBippyPhos)Cl (π-crotyl)Pd(CyBippyPhos)Cl (π-cinnamyl)Pd(CyBippyPhos)Cl The complex of formula (1) or the complex of formula (2) may be prepared in a process comprising the step of reacting a complex of formula (3) with a monodentate biaryl ligand of formula (4) or a monodentate bi-heteroaryl tertiary phosphine ligand of formula (5) to form the complex of formula (1) or the complex of formula (2),

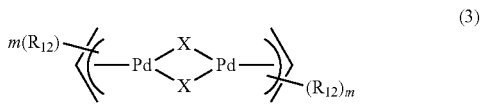 (3)

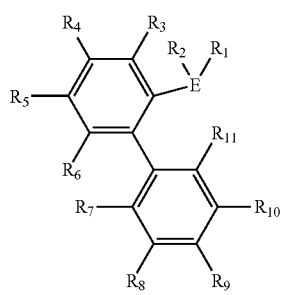 (4)

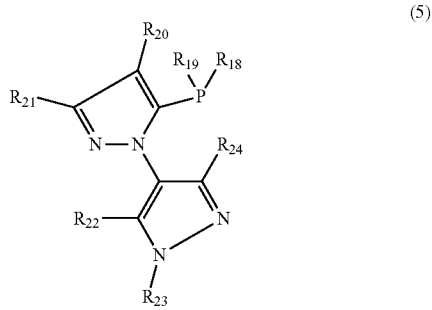 (5)

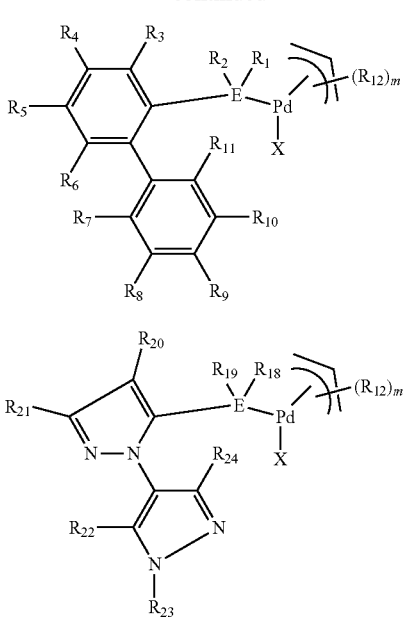

wherein, $R_1$ and $R_2$ are independently organic groups having 1-20 carbon atoms, or $R_1$ and $R_2$ are linked to form a ring structure with E;

$R_3$, $R_4$, $R_5$, $R_6$, $R_7$, $R_8$, $R_9$, $R_{10}$ and $R_{11}$ are independently —H or organic groups having 1-20 carbon atoms; or one or more pairs selected from $R_1/R_3$, $R_2/R_3$, $R_3/R_4$, $R_4/R_5$, $R_5/R_6$, $R_7/R_6$, $R_7/R_8$, $R_9/R_{10}$ or $R_{10}/R_{11}$ independently may form a ring structure with the atoms to which they are attached;

$R_{12}$ is an organic group having 1-20 carbon atoms;

$R_{18}$ and $R_{19}$ are independently selected from the group consisting of -Me, -Et, -$^n$Pr, -$^i$Pr, -$^n$Bu, -$^t$Bu, cyclohexyl and cycloheptyl;

$R_{20}$, $R_{21}$, $R_{22}$, $R_{23}$ and $R_{24}$ are independently —H or organic groups having 1-20 carbon atoms; or one or both pairs selected from $R_{20}/R_{21}$ or $R_{22}/R_{23}$ independently may form a ring structure with the atoms to which they are attached;

m is 0, 1, 2, 3, 4 or 5;

E is P or As; and

X is a coordinating anionic ligand;

provided that the palladium complex of formula (1) is not (π-crotyl)PdCl(dicyclohexylphosphino-2-biphenyl).

$R_1$, $R_2$, $R_3$, $R_4$, $R_5$, $R_6$, $R_7$, $R_8$, $R_9$, $R_{10}$, $R_{11}$, $R_{12}$, $R_{18}$, $R_{19}$, $R_{20}$, $R_{21}$, $R_{22}$, $R_{23}$ and $R_{24}$, m, E and X are as described above.

One or more pairs (e.g. 1, 2 or 3 pairs) selected from $R_1/R_3$, $R_2/R_3$, $R_3/R_4/R_5$, $R_9/R_6$, $R_7/R_8$, $R_8/R_9$, $R_9/R_{10}$ or $R_{10}/R_{11}$ may independently form a ring structure with the atoms to which they are attached. The pair or pairs are selected up to the limitations imposed by stability and the rules of valence. The ring structure may be a substituted or unsubstituted cycloalkyl, substituted or unsubstituted heterocycloalkyl, substituted or unsubstituted aryl or substituted or unsubstituted heteroaryl group.

If $R_1$, $R_2$, $R_3$, $R_4$, $R_5$, $R_6$, $R_7$, $R_8$, $R_9$, $R_{10}$ or $R_{11}$ does not form part of a pair, the groups are as described above.

$R_1/R_3$ or $R_2/R_3$ may form a ring structure with the atoms to which they are attached and in this instance $R_4/R_5$, $R_5/R_6$, $R_7/R_8$, $R_8/R_9$, $R_9/R_{10}$ or $R_{10}/R_{11}$ independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above. $R_1$ and $R_2$ may be independently selected from the groups defined above when they do not form a ring structure with $R_3$.

The linking group for $R_1/R_3$ or $R_2/R_3$ may be a substituted or unsubstituted alkyl, substituted or unsubstituted alkoxy, or substituted or unsubstituted heteroalkyl. The ring structure formed from the pair or pairs selected from the group consisting of $R_4/R_5$, $R_5/R_6$, $R_7/R_8$, $R_8/R_9$, $R_9/R_{10}$ and $R_{10}/R_{11}$ may be a substituted or unsubstituted cycloalkyl, substituted or unsubstituted heterocycloalkyl, substituted or unsubstituted aryl or substituted or unsubstituted heteroaryl group. $R_1$ and $R_2$ may be independently selected from the groups defined above when they do not form a ring structure with $R_3$.

In one embodiment, $R_4$, $R_5$ and $R_6$ are —H and the pair $R_1/R_3$ or $R_2/R_3$ forms a ring structure with the atoms to which they are attached. In another embodiment, $R_4$, $R_5$ and $R_6$ are —H and the pair $R_1/R_3$ or $R_2/R_3$ forms a ring structure with the atoms to which they are attached. In either of these instances, $R_7/R_8$, $R_8/R_9$, $R_9/R_{10}$ or $R_{10}/R_{11}$ may independently form a ring structure with the carbon atoms to which they are attached or $R_7$, $R_8$, $R_9$, $R_{10}$ and $R_{11}$ are as defined above. $R_1/R_3$ or $R_2/R_3$ may form a ring structure selected from the group consisting of:

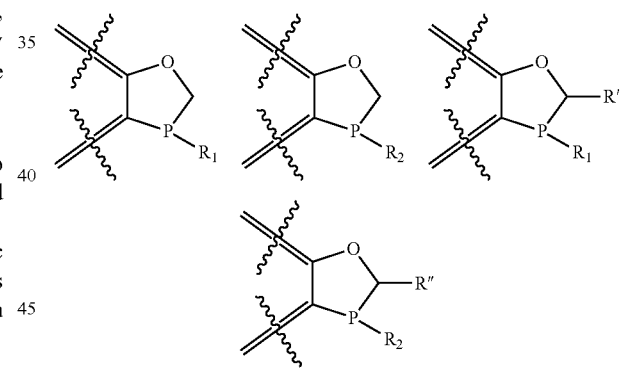

wherein:

$R_1$ and $R_2$ are as defined above: and

R' and R" are independently as defined above for $R_1$ and $R_2$.

In one embodiment, R' and R" are independently selected from the group consisting of methyl, propyl (n- or i-), butyl (n-, i- or t-), cyclohexyl or phenyl.

In another embodiment, $R_9$ is —H and the pairs $R_7/R_8$ and $R_{10}/R_{11}$ form a ring structure with the atoms to which they are attached. Each pair may form a substituted or unsubstituted aryl ring (for example, a phenyl ring) together with the carbon atoms to which they are attached.

Examples of phosphorus ligands include those described by Tang et al, Angew. Chem. Int. Ed. 2010, 49, 5879-5883, Zhao et al, Chem. Eur. J, 2013, 19(7), 2261-2265 and Xu et al, Journal of the American Chemical Society, 2014, 136(2), 570-573 such as:

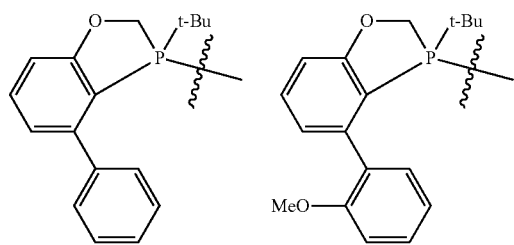

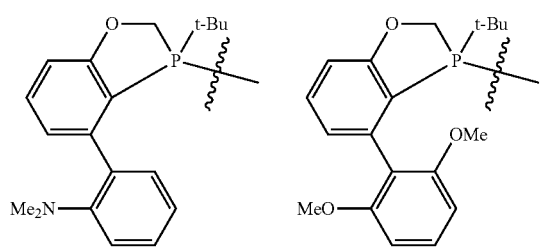

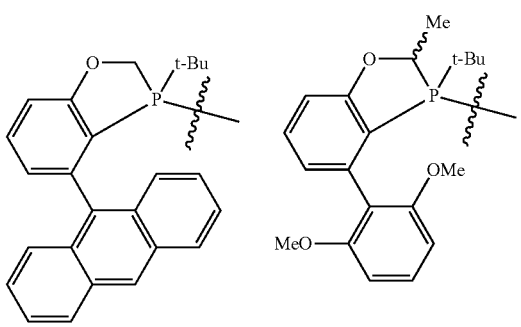

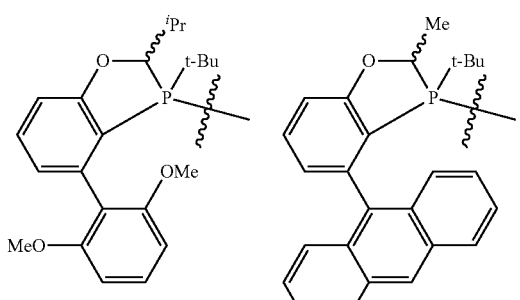

It will be understood that, in the depictions herein, where -Me or -$^i$Pr is connected by a wavy line ($\sim\!\!\sim$), either stereoisomer may be present.

In one embodiment, $R_5$ and $R_6$ form a substituted or unsubstituted aryl ring, preferably a phenyl ring, together with the carbon atoms to which they are attached. In another embodiment, $R_7$ and $R_8$ form a substituted or unsubstituted aryl ring, preferably a phenyl ring, together with the carbon atoms to which they are attached. An example is represented below:

Without wishing to be bound by theory, it is believed that the complexes of formula (1) can be prepared as a result of balancing the steric bulk of groups $R_1$ and $R_2$ with the steric bulk of groups $R_7$, $R_8$, $R_9$, $R_{10}$ and/or $R_{11}$. For example, in the complex of formula (1), when E is P, $R_1$ and $R_2$ may be selected to be more sterically bulky than a cyclohexyl group (for example a tert-butyl group) when the substituents $R_7$, $R_8$, $R_9$, $R_{10}$ and/or $R_1$ are selected to be less sterically bulky (for example H). Similarly, $R_1$ and $R_2$ are typically selected to be less sterically bulky (for example a cyclohexyl group or smaller) when the substituents $R_7$, $R_8$, $R_9$, $R_{10}$ and/or $R_{11}$ are selected to be more sterically bulky (for example methoxy, iso-propyl, dimethylamino).

The complex of formula (3) may be prepared according to known methods (see, for example, a) Marion, N.: Navarro, O.; Mei, J.; Stevens, E. D.; Scott, N. M.; Nolan, S. P. *J. Am. Chem. Soc.* 2006, 128, 4101. b) Auburn, P. R.; Mackenzie, P. B.; Bosnich, B. *J. Am. Chem. Soc.* 1985, 107, 2033. c) Dent, W. I.; Long, R.; Wilkinson, G. *J. Chem. Soc.* 1964, 1585. d) Nicholson, J. K.; Powell, J.; Shaw, B. L. *J. Chem. Soc.; Chem. Commun.* 1966, 174) each of which is incorporated herein by reference in its entirety for all purposes. Suitable complexes of formula (3) include:

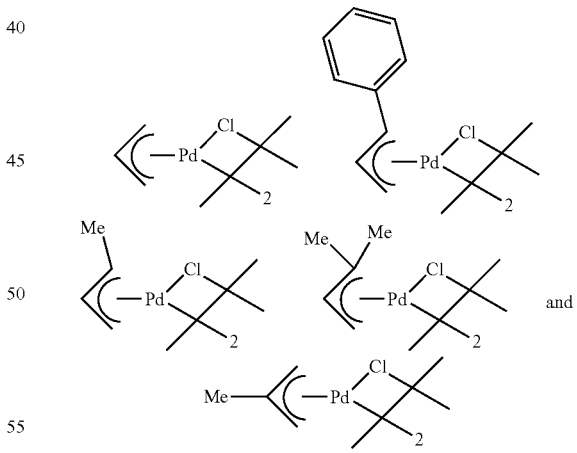

In one embodiment, the process comprises the step of reacting the complex of formula (3) with the monodentate ligand of formula (4) to form the complex of formula (1). In another embodiment, the process comprises the step of reacting the complex of formula (3) with the monodentate bi-heteroaryl phosphine ligand of formula (5) to form the complex of formula (2).

The complex of formula (3) and the ligand (4) or (5) may be combined in a solvent. In this case, the solvent is any suitable aprotic solvent or combination of aprotic solvents.

Examples of aprotic solvents are toluene, benzene, tetrahydrofuran (THF), 2-methyltetrahydrofuran, dichloromethane (DCM), dioxane, acetone, acetonitrile, dimethylformamide (DMF), N-methylpyrrolidine (NMP), dimethylacetamide (DMAc), methyltertbutylether (MTBE), diethylether, hexane, heptane, pentane or ethylacetate. Preferred solvents are THF, 2-methyltetrahydrofuran, toluene, DCM or a combination thereof. The solvent may be anhydrous. The concentration of the complex of formula (3) in the solvent is preferably about 0.001 mol/L to about 3.00 mol/L and more preferably, about 0.03 mol/L to about 2.50 mol/L.

Any suitable quantity of ligand may be used, although it is preferred that the molar ratio of the complex of formula (3):ligand is from about 1:1 to about 1:15, such as about 1:1 to about 1:11. In one embodiment, the molar ratio of complex of formula (3):ligand about 1:1.90 to about 1:2.30.

The reaction is preferably carried out under an inert atmosphere, such as nitrogen or argon.

The process of the invention may be carried out at a temperature in the range of about −10° C. to about 60° C., preferably about 0° C. to about 35° C. and more preferably at about room temperature (rt) (i.e. about 20° C. to about 30° C.). It is preferred that the temperature is maintained below the decomposition temperature and so when the complexes of formula (1), (2) or (3) are known to decompose within the temperature ranges given above, the temperature should be maintained below the decomposition temperature.

The reaction may be carried out for a period of from about several minutes to about 24 hours. Usually the reaction is complete within about 6 hours for a laboratory scale reaction. On completion, a proportion of the solvent may be evaporated if desired prior to recovery of the complex. Furthermore, if desired an anti-solvent (e.g. an alkane, such as pentane or hexane) may be used to precipitate the complex from the solvent. The complex product may be recovered directly by filtering, decanting or centrifuging.

Howsoever the complex is recovered, the separated complex may be washed and then dried. Drying may be performed using known methods, for example at temperatures in the range 10-60° C. and preferably 20-40° C. under 1-30 mbar vacuum for 1 hour to 5 days. If desired the complex may be recrystallised.

In certain embodiments, the complexes may be prepared in high yield. In certain embodiments, the complexes may be prepared having a high purity. In certain embodiments, the complexes are highly active catalysts. In certain embodiments, the complexes are stable to air and moisture at ambient temperatures. A number of complexes (for example, (π-allyl)Pd(CyBippyPhos)Cl, (π-allyl)Pd(SPhos)Cl, (π-allyl)Pd(XPhos)Cl, (π-allyl)Pd(RuPhos)Cl, (π-allyl)Pd(BrettPhos)Cl, (π-crotyl)Pd(XPhos)Cl, (π-crotyl)Pd(SPhos)Cl, (π-crotyl)Pd(RuPhos)Cl, (π-cinnamyl)Pd(SPhos)Cl and (π-cinnamyl)Pd(RuPhos)Cl) were tested for storage stability and showed substantially no decomposition as judged by $^{31}$P NMR under normal storage conditions for 1-2 years. Normal storage conditions refers to storage in air under normal moisture conditions (i.e. not in a glovebox or desiccator). Application studies of the complexes indicate that they may be easily activated under mild conditions. For example, allyl complexes may be typically activated at >60° C., and the crotyl and cinnamyl complexes may be activated readily at room temperature. If desired, however, the complexes of the present invention may be used in reactions at higher temperatures (for example, ≥ about 60° C. to about ≤ about 150° C.).

Without wishing to be bound by theory, it is believed that the complexes activate to form an LPd(0) species (L=phosphine ligand). Relatively benign substituted olefin by-products may also be produced on activation of the complexes. An example of an olefin by-product is shown below for a particular π-allyl complex where m is 1.

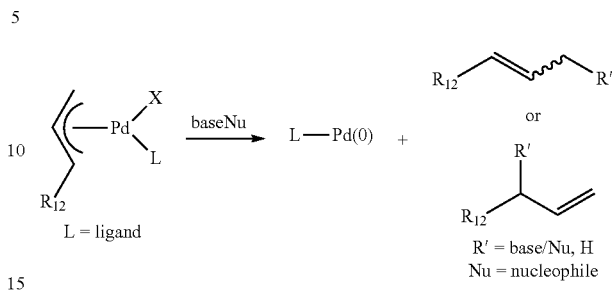

Without wishing to be bound by theory, it is also believed that the activity observed by the complexes of the present invention may be as a result of suppressing the formation of stable non-reactive (μ-$(R_{12})_m$-allyl)Pd$_2$(L)$_2$(μ-Cl) dimers. In this respect, the active "LPd(0)" species may be consumed by comproportionation with the yet unreacted complex of formula (1) or (2) to form the dimer complexes. The suppression of the comproportionation process may be caused by the dimer complexes becoming increasingly destabilized with increasing ligand size and/or substitution on the allyl group due to steric strain, thereby retarding their propensity to form. Additionally, the fast rate of oxidative addition that the complexes of the invention exhibit should rapidly draw the active L-Pd(0) into the catalytic cycle, thus, disfavouring the non-productive comproportionation process. These mechanisms are illustrated in FIG. 1 for a particular π-allyl complex where L is a ligand of formula (4) or (5), X is chloro and m is 1.

The catalysts of the present invention may be used for carbon-carbon coupling reactions. Examples of carbon-carbon coupling reactions include Heck, Suzuki, Sonogashira or Negishi reactions, ketone α-arylation reactions, aldehyde α-arylation reactions, allylic substitution reactions and trifluoromethation reactions. The catalysts of the present invention may also be used for carbon-heteroatom coupling reactions, such as carbon-nitrogen coupling reactions (i.e. Buchwald-Hartwig reaction), or carbon-oxygen or carbon-sulfur coupling reactions.

In another aspect, therefore, the present invention provides a process for carrying out a carbon-carbon coupling reaction in the presence of a catalyst, the process comprising:
(a) the use of a complex of formula (1):

(1)

wherein:
$R_1$ and $R_2$ are independently organic groups having 1-20 carbon atoms, or $R_1$ and $R_2$ are linked to form a ring structure with E;

$R_3$, $R_4$, $R_5$, $R_6$, $R_7$, $R_8$, $R_9$, $R_{10}$ and $R_{11}$ are independently —H or organic groups having 1-20 carbon atoms; or $R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above;

$R_{12}$ is an organic group having 1-20 carbon atoms;

m is 0, 1, 2, 3, 4 or 5;

E is P or As; and

X is a coordinating anionic ligand;

or:

(b) a complex of formula (2) as defined in any one of Aspects 17 to 24, wherein Aspects 17 to 24 are set forth as:

Aspect 17: A palladium complex of formula (2)

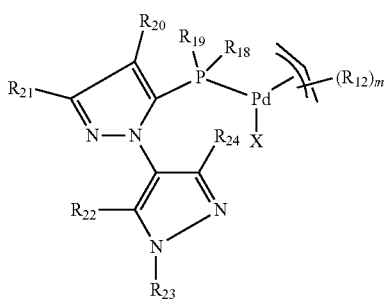

(2)

wherein:

$R_{18}$ and $R_{19}$ are independently selected from the group consisting of —Me, -Et, -nPr, -iPr, -nBu, iBu, cyclohexyl and cycloheptyl;

$R_{12}$ is an organic group having 1-20 carbon atoms;

$R_{20}$, $R_{21}$, $R_{22}$, $R_{23}$ and $R_{24}$ are independently —H or organic groups having 1-20 carbon atoms; or one or both pairs selected from $R_{20}/R_{21}$ or $R_{22}/R_{23}$ may independently form a ring structure with the atoms to which they are attached;

m is 0, 1, 2, 3, 4 or 5; and

X is a coordinating anionic ligand;

Aspect 18: The palladium (II) complex according to Aspect 17, wherein $R_{18}$ and $R_{19}$ are the same and are cyclohexyl groups.

Aspect 19: The palladium(ii) complex according to Aspect 17 or Aspect 18, wherein $R_{20}$ and $R_{21}$ are independently selected rom the group ocnsisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)2 (wherein the aryl groups may be the same or different), substituted and unsubstituted —N(heteroaryl)2 (wherein the heteroaryl groups may be the same or different) and substituted and unsubstituted heterocycloalkyl groups.

Aspect 20: The palladium(II) complex according to Aspect 19, wherein both $R_{20}$ and $R_{21}$ are —H.

Aspect 21: The palladium(II) complex according to any one of Aspects 17 to 20, wherein $R_{22}$ and $R_{24}$ are independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted —thioalkyl, substituted and unsubstituted aryl, substituted and unsubstituted heteraryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the clycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different).

Aspect 22: The palladium(II) complex according to any one of Aspects 17 to 21, wherein $R_{23}$ is selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, and substituted and unsubstituted heteroaryl.

Aspect 23: The palladium(II) complex according to any one of Aspects 17 to 22, wherein each of $R_{22}$, $R_{23}$ and $R_{24}$ are phenyl groups.

Aspect 24: The palladium(II) complex according to any one of Aspects 17 to 23, wherein the complex of formula (2) is selcted from the group consisting of:

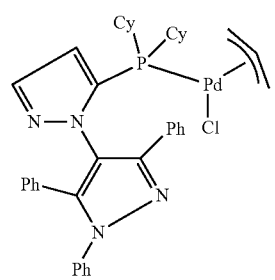

(π-allyl)Pd(CyBippyPhos)Cl

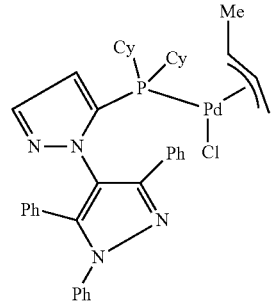

(π-crotyl)Pd(CyBippyPhos)Cl

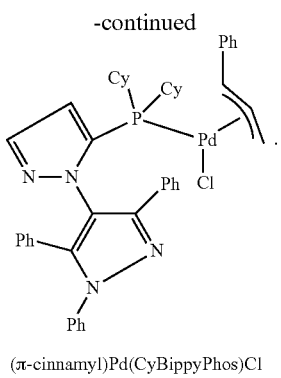

(π-cinnamyl)Pd(CyBippyPhos)Cl

The complex of formula (1), the complex of formula (2), $R_1$, $R_2$, $R_3$, $R_4$, $R_5$, $R_6$, $R_7$, $R_8$, $R_9$, $R_{10}$, $R_{11}$, $R_{12}$, $R_{18}$, $R_{19}$, $R_{20}$, $R_{21}$, $R_{22}$, $R_{23}$ and $R_{24}$, m, E and X are as described above.

In one embodiment, the process comprises the use of a complex of formula (1) as defined in any one of Aspects 1 to 16, where Aspects 1 to 16 are set forth as:

Aspect 1: A palladium(II) complex of formula(1)

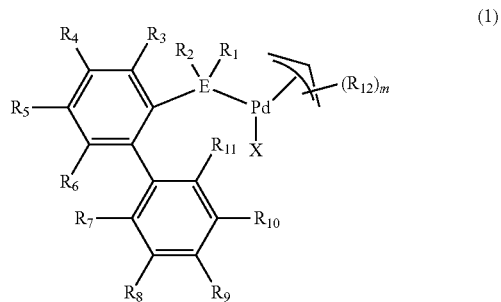

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$, and $R_{11}$ are independently —H or organic groups having 1-20 carbon atoms; or $R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$, or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$, and $R_{11}$ are as defined above;
$R_{12}$ is an organic group having 1-20 carbon atoms;
m is 0, 1, 2, 3, 4 or 5;
E is P or As; and
X is a coordinating anionic ligand;
provided that the palladium complex of formula(1) is not (π-crotyl)PdCl(dicyclohexylphosphino-2-biphenyl).

Aspect 2: The palladium(II) complex according to Aspect 1, wherein E is P.

Aspect 3: The palladium(II) complex according to Aspect 2, wherein $R_1$ and $R_2$ are more sterically bulky than a cyclohexyl group when $R_7$, $R_8$, $R_9$, $R_{10}$, and/or $R_{11}$ are less sterically bulky than a cyclohexyl group.

Aspect 4: The palladium(II) complex according to Aspect 2, wherein $R_1$ and $R_2$ are less sterically bulky than a cyclohexyl group when $R_7$, $R_8$, $R_9$, $R_{10}$, and/or $R_{11}$ are more sterically bulky than a cyclohexyl group.

Aspect 5: The palladium(II) complex according to any one of Aspects 1 to 4, wherein $R_1$ and $R_2$ are independently selected from the group consisting of substituted and unsubstituted straight-chain alkyl, substituted and unsubstituted aryl, and substituted and unsubstituted heteroaryl wherein the heteroatoms are independently selected from sulfur, nitrogen and oxygen.

Aspect 6: The palladium(II) complex according to any one or Aspects 1 to 5, wherein $R_3$, $R_4$, $R_5$, and $R_6$ are independently selected from the group consisting of —H, substituted and unsubstituted straight-chain alkyl, substituted and unsubstituted branched-chain alkyl, substituted and unsubstituted cycloalkyl, substituted and unsubstituted alkoxy, substituted and unsubstituted aryl, substituted and unsubstituted heteraryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl group may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different) and substituted and unsubstituted heterocycloalkyl groups.

Aspect 7: The palladium(II) complex according to Aspect 6, wherein $R_3$, $R_4$, $R_5$, and $R_6$ are —H.

Aspect 8: The palladium(II) complex according to Aspect 6, wherein two of $R_3$, $R_4$, $R_5$, and $R_6$ are —H and the other two of $R_3$, $R_4$, $R_5$, and $R_6$ are independently selected from the group consisting of unsubstituted straight-chain alkyl, unsubstituted branched-chain alkyl, unsubstituted cycloalkyl, unsubstituted alkoxy.

Aspect 9: The palladium(II) complex according to any one of Aspects 1 to 8, wherein $R_7$, $R_8$, $R_9$, $R_{10}$, and $R_{11}$ are independently selected from the group consisting of —H, substituted and unsubstituted straight-chain alkyl, substituted and unsubstituted branched-chain alkyl, substituted and unsubstituted clyoalkyl, substituted and unsubstituted alkoxy, substituted and unsubstituted aryl, substituted and unsubstituted heteroaryl, substituted and unsubstituted —N(alkyl)$_2$ (wherein the alkyl groups may be the same or different and are independently selected from straight-chain or branched-chain groups), substituted and unsubstituted —N(cycloalkyl)$_2$ (wherein the cycloalkyl groups may be the same or different), substituted and unsubstituted —N(aryl)$_2$ (wherein the aryl groups may be the same or different), substituted and unsubstituted —N(heteroaryl)$_2$ (wherein the heteroaryl groups may be the same or different) and substituted and unsubstituted heterocycloalkyl groups.

Aspect 10: The palladium(II) complex according to Aspect 9, wherein $R_7$, $R_8$, $R_9$, $R_{10}$, and $R_{11}$ are—H.

Aspect 11: The palladium(II) complex according to to Aspect 9, wherien three of $R_7$, $R_8$, $R_9$, $R_{10}$, and $R_{11}$ are —H and the other two of $R_7$, $R_8$, $R_9$, $R_{10}$, and $R_{11}$ are independently selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and are independently selected from straight-chain or branched-chain groups), and unsubstituted —N(aryl)$_2$ (wherein the aryl groups may be the same or different).

Aspect 12: The palladium(II) complex according to Aspect 9, wherein two of $R_7$, $R_8$, $R_9$, $R_{10}$, $R_{11}$ are —H and the other three of $R_7$, $R_8$, $R_9$, and $R_{11}$ are independently selected from the group consisting of unsubstituted straight-chain alkyl, unsubstituted branched-chain alkyl, unsubstituted cycloalkyl, unsubstituted alkoxy, unsubstituted —N(alkyl)$_2$ (wherein the alkyl groups may be the same or different and are independently selected from straight-chain or branched-chain groups), and unsubstituted —N(aryl)$_2$ (wherein the aryl groups may be the same or different).

Aspect 13: The palladium(II) complex according to any one of Aspects 1 to 12, wherein the monodentate tertiary phosphine ligand is selected from the group consisting of:

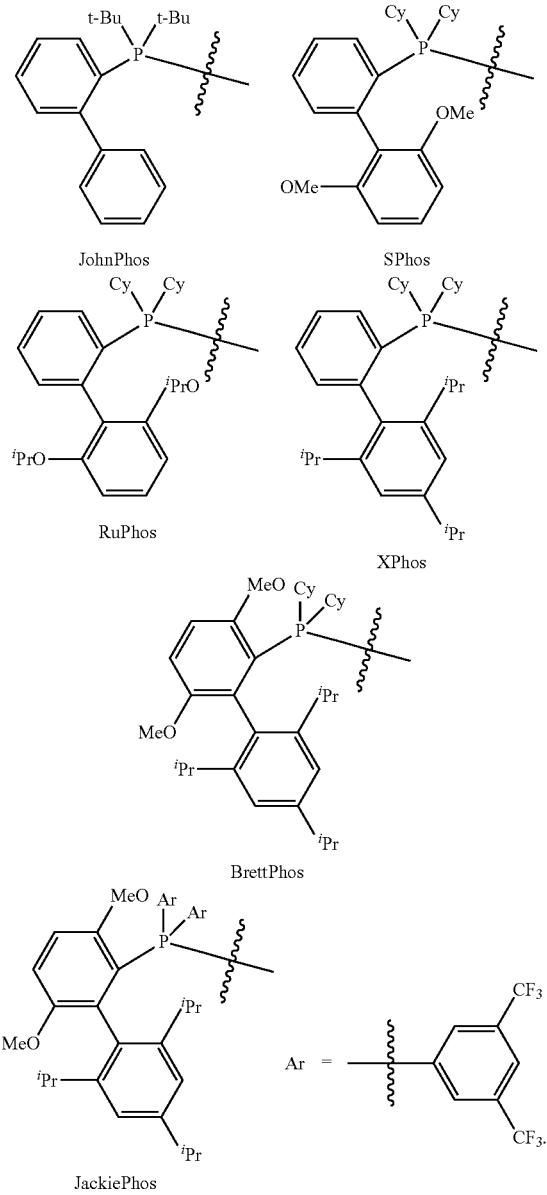

Aspect 14: The palladium(II) complex according to any one of Aspects 1 to 13, wherein $R_{12}$ is selected from the group consisting of substituted and unsubstituted straight-chain alkyl, substituted and unsubstituted branched-chain alkyl, substituted and unsubstituted cycloalkyl, substituted and unsubstituted aryl, substituted and unsubstituted heteroaryl, wherein the heteroatoms are independently selected from sulfur, nitrogen, and oxygen.

Aspect 15: The palladium(II) complex according to any one of Aspects 1 to 14, wherein X is a halo group or a trifluoroacetate group.

Aspect 16: The palladium(II) complex according to any one of Aspects 1 to 15, wherein the complex of formula (1) is selected from the group consisting of:

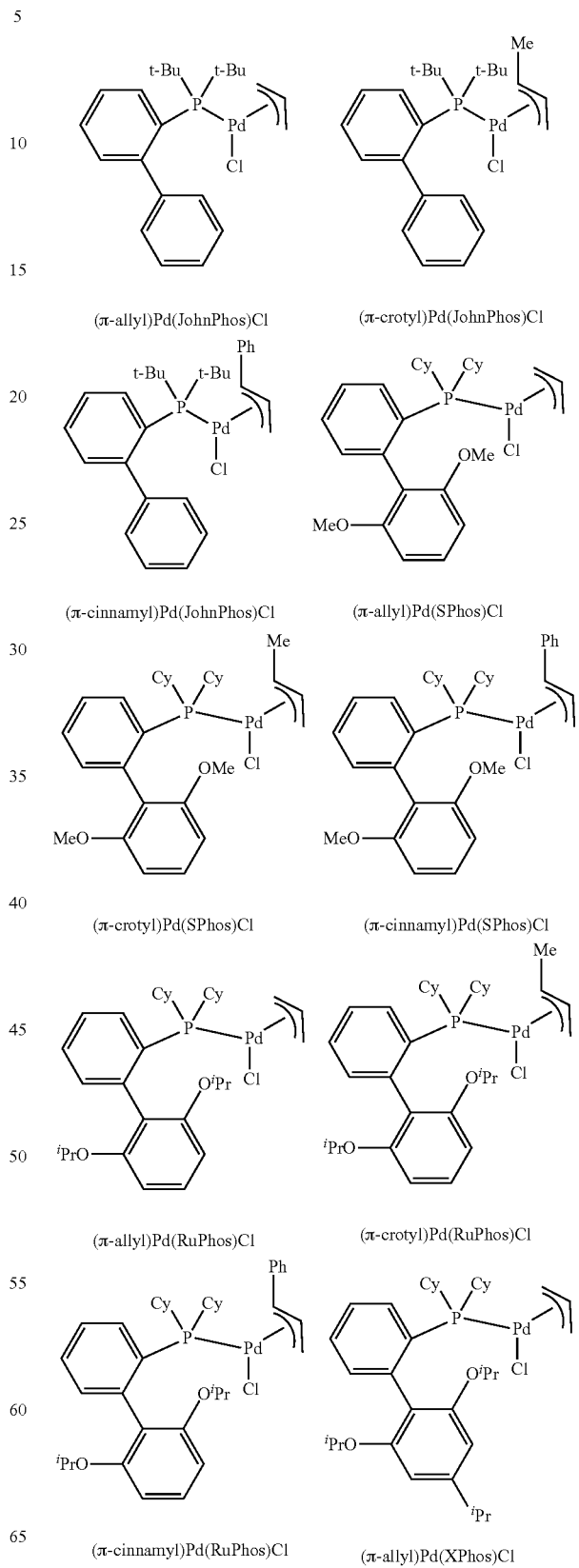

-continued
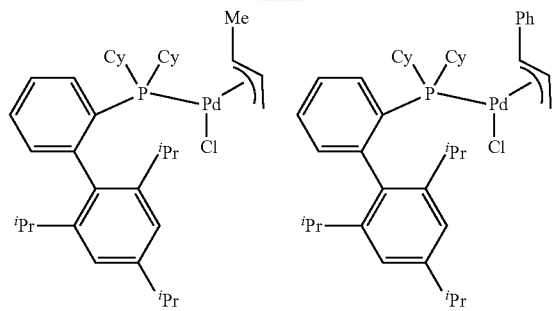
(π-crotyl)Pd(XPhos)Cl  (π-cinnamyl)Pd(XPhos)Cl
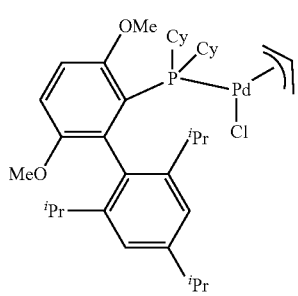
(π-allyl)Pd(BrettPhos)Cl
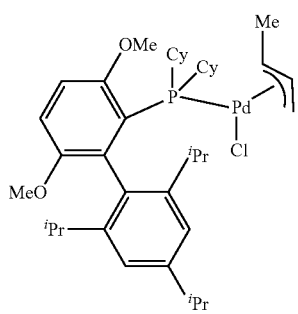
(π-crotyl)Pd(BrettPhos)Cl
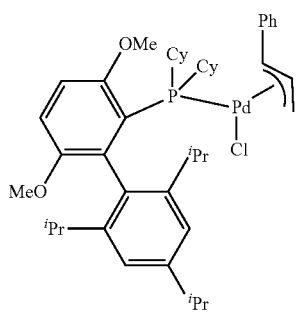
(π-cinnamyl)Pd(BrettPhos)Cl
-continued
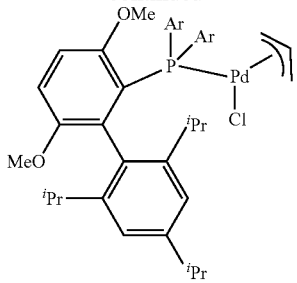
(π-allyl)Pd(JackiePhos)Cl
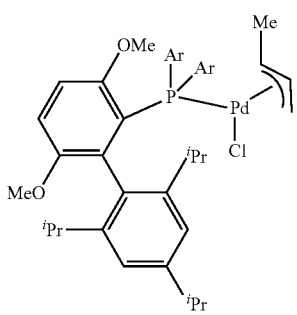
(π-crotyl)Pd(JackiePhos)Cl
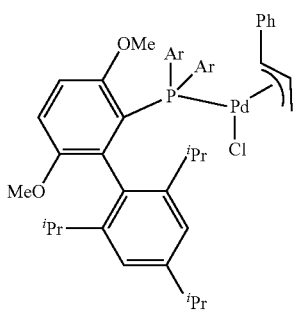
(π-cinnamyl)Pd(JackiePhos)Cl
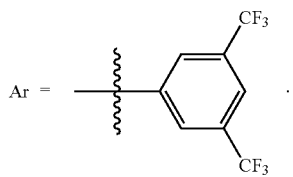
In another embodiment, the process comprises the use of the complex of formula (2) as defined in any one of Aspects 17 to 24 as set forth elsewhere herein.

In another aspect, the invention provides a process for carrying out a carbon-heteroatom coupling reaction in the presence of a catalyst, the process comprising:
(a) the use of a complex of formula (1):

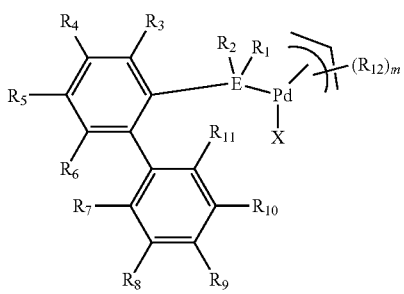

(1)

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or
$R_1/R_3$ or $R_2/R_3$ forms a ring structure with the atoms to which they are attached and in this instance $R_4/R_5$, $R_5/R_6$, $R_7/R_8$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above;
$R_{12}$ is an organic group having 1-20 carbon atoms;
m is 0, 1, 2, 3, 4 or 5;
E is P or As; and
X is a coordinating anionic ligand;
or:
(b) a complex of formula (2) as defined in any one of Aspects 17 to 24 as set forth elsewhere herein.

The complex of formula (1), the complex of formula (2), $R_1$, $R_2$, $R_3$, $R_4$, $R_5$, $R_6$, $R_7$, $R_8$, $R_9$, $R_{10}$, $R_{11}$, $R_{12}$, $R_{18}$, $R_{19}$, $R_{20}$, $R_{21}$, $R_{22}$, $R_{23}$, $R_{24}$, m, E and X are as described above.

In one embodiment, the process comprises the use of a complex of formula (1) as defined in any one of Aspects 1 to 16 as set forth elsewhere herein. In another embodiment, the process comprises the use of the complex of formula (2) as defined in any one of Aspects 17 to 24 as set forth elsewhere herein.

In another aspect, the invention provides the use of a complex of formula (1) or a complex of formula (2) as a catalyst is carbon-carbon coupling reactions, wherein:
(a) the complex of formula (1) is:

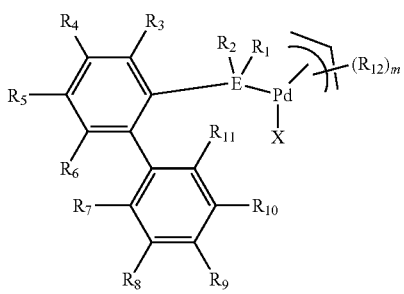

(1)

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or
$R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above;
$R_{12}$ is an organic group having 1-20 carbon atoms;
m is 0, 1, 2, 3, 4 or 5;
E is P or As; and
X is a coordinating anionic ligand;
and:
(b) a complex of formula (2) as defined in any one of Aspects 17 to 24 as set forth elsewhere herein.

The complex of formula (1), the complex of formula (2), $R_1$, $R_2$, $R_3$, $R_4$, $R_5$, $R_6$, $R_7$, $R_8$, $R_9$, $R_{10}$, $R_{11}$, $R_{12}$, $R_{18}$, $R_{19}$, $R_{20}$, $R_{21}$, $R_{22}$, $R_{23}$, $R_{24}$, m, E and X are as described above.

In one embodiment, the complex of formula (1) is as defined in any one of Aspects 1 to 14 as set forth elsewhere herein. In another embodiment, the complex of formula (2) is as defined in any one of Aspects 17 to 24 as set forth elsewhere herein.

In another aspect, the invention provides the use of a complex of formula (1) or a complex of formula (2) as a catalyst in carbon-heteroatom coupling reactions, wherein:
(a) the complex of formula (1) is:

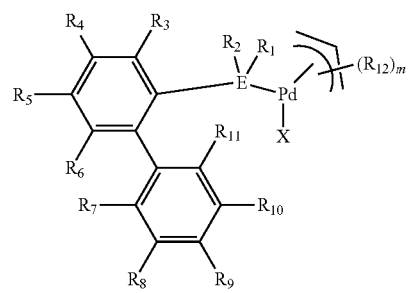

(1)

wherein:
$R_1$ and $R_2$ are independently organic groups having 1-20 carbon atoms, or $R_1$ and $R_2$ are linked to form a ring structure with E;
$R_3$, $R_4$, $R_5$, $R_6$, $R_7$, $R_8$, $R_9$, $R_{10}$ and $R_{11}$ are independently —H or organic groups having 1-20 carbon atoms; or
$R_1/R_3$ or $R_2/R_3$ forms a ring structure with the atoms to which they are attached and in this instance $R_4/R_5$, $R_5/R_6$, $R_7/R_8$, $R_8/R_9$, $R_9/R_{10}$ or $R_{10}/R_{11}$ may independently form a ring structure with the carbon atoms to which they are attached or $R_1$, $R_2$, $R_4$, $R_5$, $R_6$, $R_7$, $R_8$, $R_9$, $R_{10}$ and $R_{11}$ are as defined above;
$R_{12}$ is an organic group having 1-20 carbon atoms;
m is 0, 1, 2, 3, 4 or 5;
E is P or As; and
X is a coordinating anionic ligand;
and:
(b) the complex of formula (2) is as defined in any one of aspects 17 to 24 as set forth elsewhere herein.

The complex of formula (1), the complex of formula (2), $R_1$, $R_2$, $R_3$, $R_4$, $R_5$, $R_6$, $R_7$, $R_8$, $R_9$, $R_{10}$, $R_{11}$, $R_{12}$, $R_{18}$, $R_{19}$, $R_{20}$, $R_{21}$, $R_{22}$, $R_{23}$, $R_{24}$, m, E and X are as described above.

In one embodiment, the complex of formula (1) is as defined in any one of Aspects 1 to 16 as set forth elsewhere herein. In another embodiment, the complex of formula (2) is as defined in any one of Aspects 17 to 24 as set forth elsewhere herein.

Embodiments and/or optional features of the invention have been described above. Any aspect of the invention may be combined with any other aspect of the invention, unless the context demands otherwise. Any of the embodiments or optional features of any aspect may be combined, singly or in combination, with any aspect of the invention, unless the context demands otherwise.

EXAMPLES

All solvents and reagents were purchased from commercial sources and used as received. All catalysts, ligands or precious metal precursors were obtained from Johnson Matthey Catalysis or Alfa Aesar. Flash chromatography was performed either on a Teledyne Isco CombiFlashRf using 12 g RediSepRf silica gel cartridges. $^{31}P$, $^1H$ and $^{13}C$ NMR spectra were recorded on a 400 MHz spectrometer, with chemical shifts reported relative to residual solvent as internal references (CDCl$_3$: 7.26 ppm for $^1H$ NMR and 77.26 ppm for $^{13}C$ NMR, C$_6$D$_6$: 7.16 ppm for $^1H$ NMR and 128.06 ppm $^{13}C$ NMR, DMSO-d6: 2.50 ppm for $^1H$ NMR and 39.52 ppm for $^{13}C$ NMR, toluene-d8: 2.08 ppm for $^1H$ NMR and 20.43 ppm for $^{13}C$ NMR), unless otherwise stated, while $^{31}P\{^1H\}$ NMR spectra were externally referenced to 85% H$_3$PO$_4$. The following abbreviations were used to explain the multiplicities: s=singlet, d=doublet, t=triplet, q=quartet, quint=quintet, sept=septet, m=multiplet, b=broad, app t=apparent triplet, app d=apparent doublet, br=broad. Elemental analyses were sent to Robertson Microlit Laboratories, Inc. All reactions were carried out in individual Schlenk flasks under a nitrogen atmosphere. The purity of the isolated products was >95% as determined by $^1H$ NMR, GC/MS or elemental analysis unless noted otherwise.

Crystallographic data were obtained at 120K on a APEX Bruker-AXS CCD X-ray diffractometer equipped with a monocap collimator. Structures were solved with SHELXTL software. These data was obtained from University of Delaware X-ray Crystallography Laboratory of the Department of Chemistry and Biochemistry.

General Procedure for the Preparation of [Pd(Optionally Substituted (R$_{12}$)$_n$-Allyl)(X)]$_2$ Complexes Distilled H$_2$O in a three-necked roundbottom flask is purged with nitrogen for 30 minutes. PdCl$_2$ and KCl are subsequently added to the flask and the solution is stirred at room temperature for 1 h. Then, optionally substituted (R$_4$)$_n$-allyl chloride is added and the resulting reaction mixture is stirred at room temperature overnight (18-20 hrs). The reaction is extracted with chloroform, and the aqueous layer washed with chloroform three times. The organic layers are combined, dried over MgSO$_4$, filtered and concentrated in vacuo. The crude product is recrystallised from chloroform and methyl tert-butyl ether, and the resulting solid is isolated by filtration and dried in vacuo.

[Pd(π-Cinnamyl)Cl]$_2$

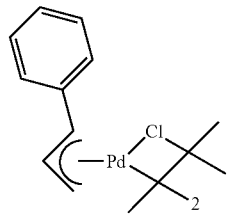

PdCl$_2$ (590 mg, 3.33 mmol); KCl (473 mg, 6.67 mmol); cinnamyl chloride (1.39 mL, 9.99 mmol); H$_2$O (83 mL). The dimer is obtained as a yellow solid.

[Pd(π-1-Crotyl)Cl]$_2$

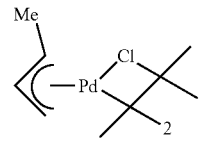

PdCl$_2$ (590 mg, 3.33 mmol); KCl (473 mg, 6.67 mmol); crotyl chloride (0.97 mL, 9.99 mmol); H$_2$O (83 mL). The dimer is obtained as a yellow solid.

[Pd(π-Prenyl)Cl]$_2$

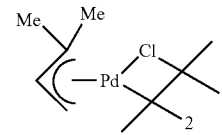

PdCl$_2$ (590 mg, 3.33 mmol); KCl (473 mg, 6.67 mmol); 1-chloride-3-methyl-2-butene (1.13 mL, 9.99 mmol); H$_2$O (83 mL). The dimer is obtained as a yellow solid.

[Pd(π-Methallyl)Cl]$_2$

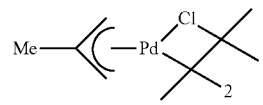

PdCl$_2$ (590 mg, 3.33 mmol); KCl (473 mg, 6.67 mmol); 3-chloride-2-methyl-1-propene (0.98 mL, 9.99 mmol); H$_2$O (83 mL). The dimer is obtained as a yellow solid (269 mg, 41%).

Example 1 (According to the Invention)

Representative Procedure for the Preparation of [Pd(Optionally Substituted (R$_{12}$)$_m$-Allyl)(Ligand)(X) Complexes:

A dry Schlenk tube is charged with the ligand (4.74 mmol) and [(optionally substituted (R$_{12}$)$_m$-allyl)PdCl]$_2$ (2.36 mmol). The tube is evacuated and backfilled with nitrogen a total of three times. 10 mL of anhydrous solvent (such as THF or toluene) is added and the mixture is stirred at room temperature for a period of time (e.g. 20 minutes). Pentane (5 mL) or hexanes is added to fully precipitate the product. The product is collected by vacuum filtration, washed (3×10 mL of pentane, or hexanes) and dried under vacuum.

Pd(π-Allyl)(JohnPhos)Cl

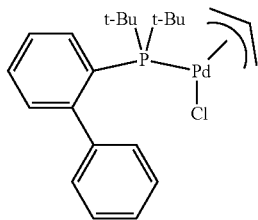

Following the representative procedure: [(allyl)PdCl]$_2$ (1.00 g, 2.75 mmol); JohnPhos (1.64 g, 5.50 mmol); toluene (13.2 mL); 1 h. Product obtained as a pale yellow solid (2.46 g, 93%); $^1$H NMR (400 MHz, CDCl$_3$, δ): 7.93-7.82 (m, 1H), 7.71-7.57 (m, 2H), 7.50-7.19 (m, 6H), 4.85-2.60 (m, 5H), 1.90-1.10 (m, 18H); $^{13}$C NMR (100 MHz, CDCl$_3$, δ): 149.0, 148.8, 142.2 (2 peaks), 134.8, 134.6, 133.6 (2 peaks), 130.4, 129.8, 129.7, 129.6, 128.1, 126.3, 125.4, 125.3, 113.3, 113.2, 81.7 (br), 57.6 (br), 37.2, 30.9 [Observed complexity due to C—P coupling]; $^{31}$P NMR (162 MHz, CDCl$_3$, δ): 57.3; Anal. calcd. for C$_{23}$H$_{32}$ClPPd: C, 57.39; H, 6.70. Found C, 57.35; H, 6.53.

(π-Crotyl)Pd(JohnPhos)Cl

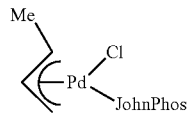

A dry Schlenk flask equipped with a Teflon-coated magnetic stir bar is charged with 1.00 g (2.54 mmol) of [(crotyl)PdCl]$_2$ (0.50 equiv) followed by 1.52 g (5.08 mmol) of JohnPhos. The flask is fitted with a rubber septum and it is evacuated and backfilled with nitrogen. This evacuation/nitrogen backfill cycle is repeated two additional times. Solvent (anhydrous toluene) is added via syringe and the reaction mixture is stirred at rt for 1.25 hours. Pentane (25 mL) is then added to fully precipitate the product. The solid materials are then collected by suction filtration, washed with additional pentane (or hexanes), and dried in vacuo to give 2.40 g (4.84 mmol, 95%) of the title compound as a yellow solid.

$^1$H NMR (400 MHz, CDCl$_3$, δ): 7.87 (s, 1H), 7.50-7.75 (m, 2H), 7.10-7.50 (m, 6H), 3.98-4.23 (m, 1H), 3.60-3.83 (m, 1H), 2.99-3.11 (m, 1H), 1.20-1.76 (m, 22H).

$^{13}$C NMR (101 MHz, CDCl$_3$, δ): 149.0, 148.8, 142.1 (2 peaks), 135.0, 133.9 (2 peaks), 130.4, 130.0, 129.8, 129.7, 127.9, 126.4, 125.2 (2 peaks), 112.7 (2 peaks), 100.3, 100.0, 52.2, 37.7, 37.6, 37.3, 37.2, 31.7, 31.6, 30.5, 30.4, 17.7, 17.6 [Observed complexity due to C—P coupling].

$^{31}$P NMR (162 MHz, CDCl$_3$, δ): 57.1.

Anal. Calcd. for C$_{24}$H$_{34}$ClPPd: C, 58.19; H, 6.92. Found: C, 57.91; H, 6.74.

Pd(π-Allyl)(SPhos)Cl

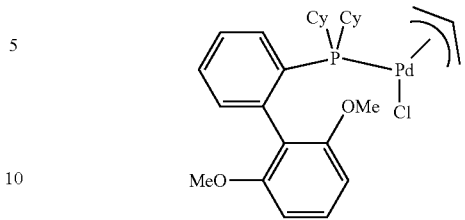

Following the representative procedure: [(allyl)PdCl]$_2$ (505 mg, 1.39 mmol); SPhos (1.14 g, 2.78 mmol); THF (3 mL); 6 h. Product obtained as a white solid (1.30 g, 79%); $^1$H NMR (400 MHz, CDCl$_3$, δ): 7.65 (t, J=8.6 Hz, 1H), 7.42 (t, J=7.4 Hz, 1H), 7.33 (t, J=7.8 Hz, 1H), 7.30-7.22 (m, 1H), 7.06 (dd, J=3.5 Hz, 8.2 Hz, 1H), 6.70-6.44 (m, 2H), 5.24-5.08 (m, 1H), 4.47 (t, J=7.1 Hz, 1H), 3.82-3.60 (m, 6H), 3.40-3.22 (m, 1H), 3.02 (dd, J=9.4 Hz, 13.7 Hz, 1H), 2.41-2.00 (m, 3H), 2.00-0.90 (m, 20H); $^{13}$C NMR (100 MHz, CDCl$_3$, δ): 158.0, 140.6, 140.5, 134.8, 134.7, 133.0, 132.9, 131.3, 131.0, 129.5, 128.9, 125.9, 125.8, 119.4, 119.4, 115.9, 115.8, 109.9, 104.2, 103.1, 82.2, 81.9, 55.4, 54.7, 36.2 (4 peaks), 29.8, 29.0, 27.3, 27.2, 26.1 [Observed complexity due to C—P coupling]; $^{31}$P NMR (162 MHz, CDCl$_3$, δ): 31.8; Anal. calcd. for C$_{29}$H$_{40}$O$_2$ClPPd: C, 58.67; H, 6.79. Found C, 58.93; H, 6.76.

Single crystals of Pd(π-allyl)(SPhos)Cl are obtained by slow cooling of a 1:1 THF/pentane solution in the freezer.

Pd(π-Crotyl)(Sphos)Cl

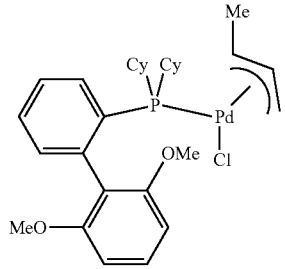

Following the representative procedure: [(crotyl)PdCl]$_2$ (501 mg, 1.27 mmol); SPhos (1.05 g, 2.56 mmol); THF (5 mL); 6 h. Product obtained as an off-white solid (1.28 g, 83%); $^1$H NMR (400 MHz, C$_6$D$_6$, δ): 7.58 (t, J=7.7 Hz, 1H), 7.17-7.04 (m, 4H), 6.42 (d, J=8.5 Hz, 1H), 6.28 (d, J=8.3 Hz, 1H), 4.69-4.58 (m, 1H), 3.77-3.62 (m, 1H), 3.53 (s, 3H), 3.25 (s, 3H), 3.20 (d, J=6.6 Hz, 1H), 2.52-2.29 (m, 2H), 2.20-1.15 (m, 24H); $^{13}$C NMR (100 MHz, C$_6$D$_6$, δ): 158.0, 157.7, 141.8, 141.7, 133.4 (2 peaks), 133.2, 133.1, 132.0, 131.7, 129.1 (2 peaks), 128.2, 125.6, 125.5, 119.8, 119.7, 114.1 (2 peaks), 103.7, 102.8, 99.8, 99.6, 54.8, 54.6, 48.4, 38.0, 37.8, 37.3, 37.1, 29.9, 28.5, 28.3, 27.4 (2 peaks), 27.3, 27.1, 27.0 (2 peaks), 26.9, 26.1, 17.1 (2 peaks) [Observed complexity due to C—P coupling]; $^{31}$P NMR (162 MHz, C$_6$D$_6$, δ): 28.9; Anal. calcd. for C$_{30}$H$_{42}$O$_2$ClPPd: C, 59.31; H, 6.97. Found C, 59.15; H, 7.17.

Pd(π-Cinnamyl)(Sphos)Cl

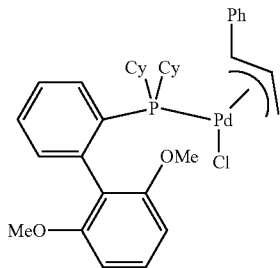

Following the representative procedure: [(cinnamyl)PdCl]$_2$ (1.00 g, 1.93 mmol); SPhos (1.59 g, 3.86 mmol); toluene (4.3 mL); 1 h. Product obtained as a yellow solid (2.56 g, 99%); $^1$H NMR (400 MHz, CDCl$_3$, δ): 7.68 (t, J=8.5 Hz, 1H), 7.48-7.20 (m, 8H), 7.08-7.02 (m, 1H), 6.60 (d, J=8.3 Hz, 1H), 5.53-5.42 (m, 1H), 4.78-4.67 (m, 1H), 3.67 (s, 6H), 3.43-2.20 (m, 4H), 2.01-1.88 (m, 2H), 1.80-1.51 (m, 8H), 1.46-1.05 (m, 10H); $^{13}$C NMR (100 MHz, CDCl$_3$, δ): 157.8, 140.3, 140.2, 136.9, 136.8, 135.0, 134.9, 133.0 (2 peaks), 131.3, 131.0, 129.3, 129.0, 128.4, 128.4, 128.1, 127.6 (2 peaks), 127.5, 125.7, 125.6, 119.4 (2 peaks), 109.3, 109.2, 103.6, 101.7, 101.4, 55.3, 50.0, 36.1, 35.9, 29.8, 29.7, 29.2, 27.3, 27.2, 27.0, 26.9, 26.1 [Observed complexity due to C—P coupling]; $^{31}$P NMR (162 MHz, CDCl$_3$, δ): 37.5; Anal. calcd. for C$_{35}$H$_{44}$O$_2$ClPPd: C, 62.78; H, 6.62. Found C, 62.66; H, 6.54.

Single crystals for X-ray analysis of Pd(T-cinnamyl)(SPhos)Cl are obtained by slow cooling of a 1:1 THF/pentane solution in the freezer.

Pd(π-Allyl)(RuPhos)Cl

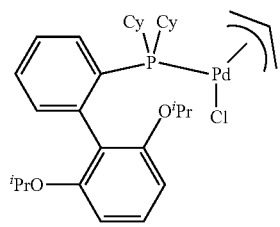

Following the representative procedure: [(allyl)PdCl]$_2$ (503 mg, 1.43 mmol); RuPhos (1.29 g, 2.77 mmol; THF (2 mL); 1 h. Product obtained as a white solid (1.52 g, 85%); $^1$H NMR (400 MHz, C$_6$D$_6$, δ): 7.60 (t, J=8.7 Hz, 1H), 7.18-7.05 (m, 4H), 6.96-6.86 (m, 1H), 6.92 (d, J=7.7 Hz, 1H), 6.32 (d, J=7.5 Hz, 1H), 5.03-4.91 (m, 1H), 4.49 (t, J=7.4 Hz, 1H), 4.46-4.30 (m, 1H), 4.22-4.08 (m, 1H), 3.37-3.22 (m, 1H), 3.01 (dd, J=9.7 Hz, 13.4 Hz, 1H), 2.55-2.04 (m, 5H), 2.03-0.80 (m, 30H); $^{13}$C NMR (100 MHz, C$_6$D$_6$, δ): 157.2, 156.7, 141.3 (2 peaks), 134.4, 134.3, 132.7, 132.6, 132.4, 132.1, 128.7 (2 peaks), 128.3, 127.9, 125.4, 125.3, 122.5, 122.4, 115.3 (2 peaks), 106.4, 105.5, 80.1, 79.8, 70.2, 69.9, 55.8, 36.2, 36.0, 35.5, 35.3, 29.5, 29.4, 27.1, 27.0, 26.2, 25.5, 22.3, 22.2, 21.6, 21.3 [Observed complexity due to C—P coupling]; 31P NMR (162 MHz, C$_6$D$_6$, δ): 34.6; Anal. calcd. for C$_{33}$H$_{48}$O$_2$ClPPd: C, 61.02; H, 7.45. Found C, 60.87; H, 7.42.

Single crystals of Pd(π-allyl)(RuPhos)Cl for X-ray analysis are obtained by slow cooling of a 1:1 THF/hexanes solution in the freezer.

Pd(π-Crotyl)(RuPhos)Cl

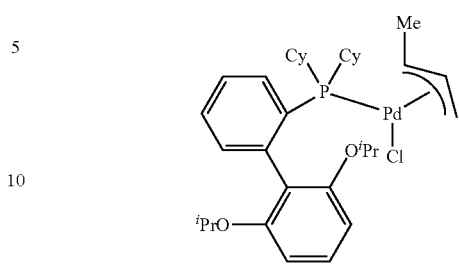

Following the representative procedure: [(crotyl)PdCl]$_2$ (1.022 g, 5.09 mmol); RuPhos (2.37 g, 10.18 mmol); THF (2.5 mL); 2 h. Product obtained as a pale yellow solid (2.93 g, 87%); $^1$H NMR (400 MHz, C$_6$D$_6$, δ): 7.64 (t, J=8.4 Hz, 1H), 7.24-7.09 (m, 3H), 7.06-7.00 (m, 1H), 6.50 (d, J=7.9 Hz, 1H), 6.34 (d, J=7.6 Hz, 1H), 4.90-4.80 (m, 1H), 4.58-4.45 (m, 1H), 4.31-4.18 (m, 1H), 3.82-3.70 (m, 1H), 3.34-3.26 (m, 1H), 2.57-0.80 (m, 38H); $^{13}$C NMR (100 MHz, C$_6$D$_6$, δ): 157.4, 156.9, 142.3, 142.2, 133.9, 133.8, 132.8 (2 peaks), 132.5, 128.9 (2 peaks), 128.2, 125.6, 125.5, 122.7 (2 peaks), 114.7 (2 peaks), 106.3, 105.4, 99.4, 99.1, 70.2, 70.0, 50.7, 37.5, 37.3, 36.7, 36.5, 30.0, 29.2, 27.4, 27.3, 27.1, 26.4, 22.5, 22.4, 21.6, 21.4, 17.4 (2 peaks) [Observed complexity due to C—P coupling]; $^{31}$P NMR (162 MHz, C$_6$D$_6$, δ): 33.2; HRMS-ESI m/z: [M–Cl], calcd. for C$_{33}$H$_{48}$O$_2$PPd, 627.2583; found 627.2554.

Single crystals of Pd(π-crotyl)(RuPhos)Cl for X-ray analysis are obtained by by slow cooling of a 1:1 THF/hexanes solution in the freezer.

Pd(π-Cinnamyl)(RuPhos)Cl

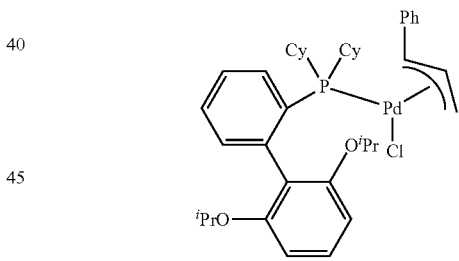

Following the representative procedure: [(cinnamyl)PdCl]$_2$ (1.00 g, 1.93 mmol); RuPhos (1.80 g, 3.86 mmol); THF (4 mL); 2 h. Product obtained as a yellow solid (2.13 g, 76%); $^1$H NMR (400 MHz, CDCl$_3$, δ): 7.78-7.68 (m, 1H), 7.46 (d, J=7.5 Hz, 1H), 7.35-7.18 (m, 7H), 6.92-6.87 (m, 1H), 6.55 (d, J=8.2 Hz, 1H), 5.72-5.58 (m, 1H), 4.91-4.77 (m, 1H), 4.52-4.39 (m, 1H), 3.00-2.50 (m, 1H), 2.31-2.19 (m, 2H), 2.05-1.94 (m, 2H), 1.74-1.49 (m, 8H), 1.44-0.89 (m, 24H); $^{13}$C NMR (100 MHz, CDCl$_3$, δ): 156.9, 140.1, 137.1 (2 peaks), 135.1, 132.8, 132.7, 131.8, 131.5, 128.7, 128.4, 127.5 (2 peaks), 127.4, 125.2, 125.1, 122.4 (2 peaks), 109.7, 109.6, 106.0, 100.3, 100.0, 70.4, 52.6, 35.0, 24.8, 30.0, 29.2, 27.0, 26.9, 26.8, 26.0, 22.4, 22.0, 21.8 [Observed complexity due to C—P coupling]; $^{31}$P NMR (162 MHz, CDCl$_3$, δ): 44.0; HRMS-ESI m/z: [M–Cl], calcd. for C$_{39}$H$_{52}$O$_2$PPd, 689.2740; found 689.2739.

Pd(π-Allyl)(XPhos)Cl

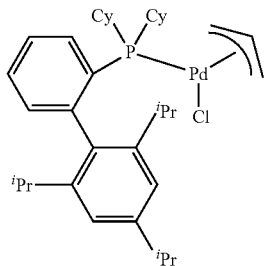

Following the representative procedure: [(allyl)PdCl]$_2$ (858 mg, 2.36 mmol); XPhos (2.56 g, 5.37 mmol); THF (5 mL); 3 h. Product obtained as a yellow solid (3.11 g, 97%), product contains ~5 mol % of THF; $^1$H NMR (400 MHz, CDCl$_3$, δ): 7.98-7.84 (m, 1H), 7.40-7.27 (m, 2H), 7.07-6.99 (m, 3H), 5.47-5.26 (m, 1H), 4.54 (t, J=7.1 Hz, 1H), 3.51 (dd, J=9.3 Hz, 13.6 Hz, 1H), 3.12-3.01 (m, 1H), 3.00-2.88 (m, 1H), 2.70-2.42 (m, 2H), 2.41-2.10 (m, 3H), 1.92-0.73 (m, 38H); $^{13}$C NMR (100 MHz, CDCl$_3$, δ): 148.7, 146.2, 142.1, 136.6, 136.4, 136.3, 133.7, 133.6, 131.8, 131.6, 128.0 (2 peaks), 125.5, 125.4, 120.7, 116.0, 116.0, 79.3, 79.0, 55.7, 34.4, 34.1, 33.9, 31.3, 30.4, 29.0, 27.1, 27.0, 26.8, 26.7, 25.6, 25.4, 23.9, 22.3 [Observed complexity due to C—P coupling], peaks attributable to THF were observed at 67.7, 25.8; $^{31}$P NMR (162 MHz, CDCl$_3$, δ): 48.0; Anal. calcd. for C$_{36}$H$_{54}$ClPPd: C, 65.55; H, 8.25. Found C, 65.79; H, 8.01.

Pd(π-Crotyl)(XPhos)Cl

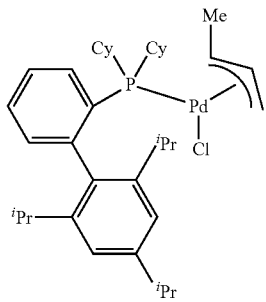

Following the representative procedure: [(crotyl)PdCl]$_2$ (1.00 g, 2.54 mmol); XPhos (2.42 g, 5.08 mmol); toluene (30 mL); 2 h. Product obtained as a white solid (3.11 g, 91%); $^1$H NMR (400 MHz, CDCl$_3$, δ): 7.99-7.86 (m, 1H), 7.38-7.29 (m, 2H), 7.18-6.99 (m, 3H), 5.19-5.03 (m, 1H), 4.32-4.13 (m, 1H), 3.00-2.80 (m, 2H), 2.71-2.42 (m, 2H), 2.31-2.02 (m, 3H), 1.95-0.74 (m, 47H); $^{13}$C NMR (100 MHz, CDCl$_3$, δ): 148.7, 146.3, 142.1, 136.9, 136.7, 136.5, 133.7, 133.6, 132.3, 132.0, 128.8, 128.0 (2 peaks), 125.5, 125.4, 120.8, 115.0 (2 peaks), 98.5, 98.2, 50.9, 34.8, 34.2, 31.4, 30.5 (2 peaks), 29.2, 27.2, 27.1, 27.0, 26.9, 26.8, 25.8, 25.7, 24.0, 22.4, 17.2, 17.1 [Observed complexity due to C—P coupling]; $^{31}$P NMR (162 MHz, CDCl$_3$, δ): 50.8; HRMS-ESI m/z: [M−Cl], calcd. for C$_{37}$H$_{56}$PPd, 637.3154; found 637.3153.

Pd(π-Cinnamyl)(XPhos)Cl

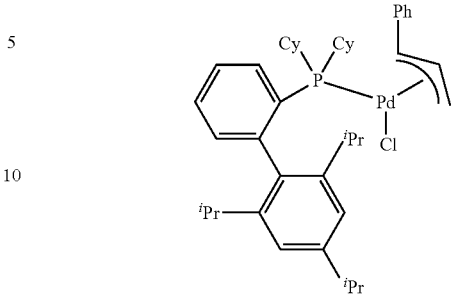

Following the representative procedure: [(cinnamyl)PdCl]$_2$ (1.00 g, 1.93 mmol); XPhos (1.84 g, 3.86 mmol); toluene (5 mL); 2 h. Product obtained as a yellow solid (2.27 g, 80%), product contains trace residual toluene; $^1$H NMR (400 MHz, CDCl$_3$, δ): 8.10-7.95 (m, 1H), 7.52 (d, J=7.5 Hz, 2H), 7.42-7.23 (m, 5H), 7.11-7.01 (m, 3H), 5.87-5.69 (m, 1H), 5.20-5.06 (m, 1H), 3.08-2.90 (m, 2H), 2.73-0.70 (m, 49H), peaks attributable to toluene were observed at 7.17 and 2.36; $^{13}$C NMR (100 MHz, CDCl$_3$, δ): 148.9, 146.4, 142.1, 137.2, 136.9, 136.8, 136.7, 136.6, 133.8, 133.7, 132.4, 132.2, 129.0, 128.6, 128.4, 128.1, 127.6 (2 peaks), 125.7, 125.6, 125.2, 121.0, 109.7, 109.6, 99.4, 99.1, 51.9, 34.5, 34.3, 31.7, 30.6, 29.2, 27.3, 27.2, 27.0, 26.9, 26.0, 25.7, 24.1, 22.5 [Observed complexity due to C—P coupling], peaks attributable to toluene were observed at 137.7, 21.4; $^{31}$P NMR (162 MHz, CDCl$_3$, δ): 54.3; Anal. calcd. for C$_{36}$H$_{54}$ClPPd: C, 68.56; H, 7.95. Found C, 68.85; H, 7.93.

Pd(π-Allyl)(BrettPhos)Cl

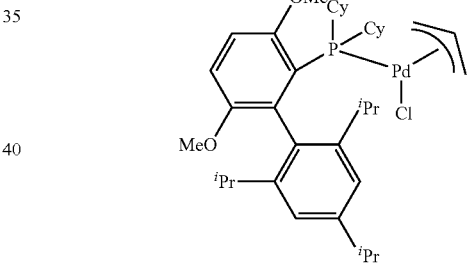

Figure 2:
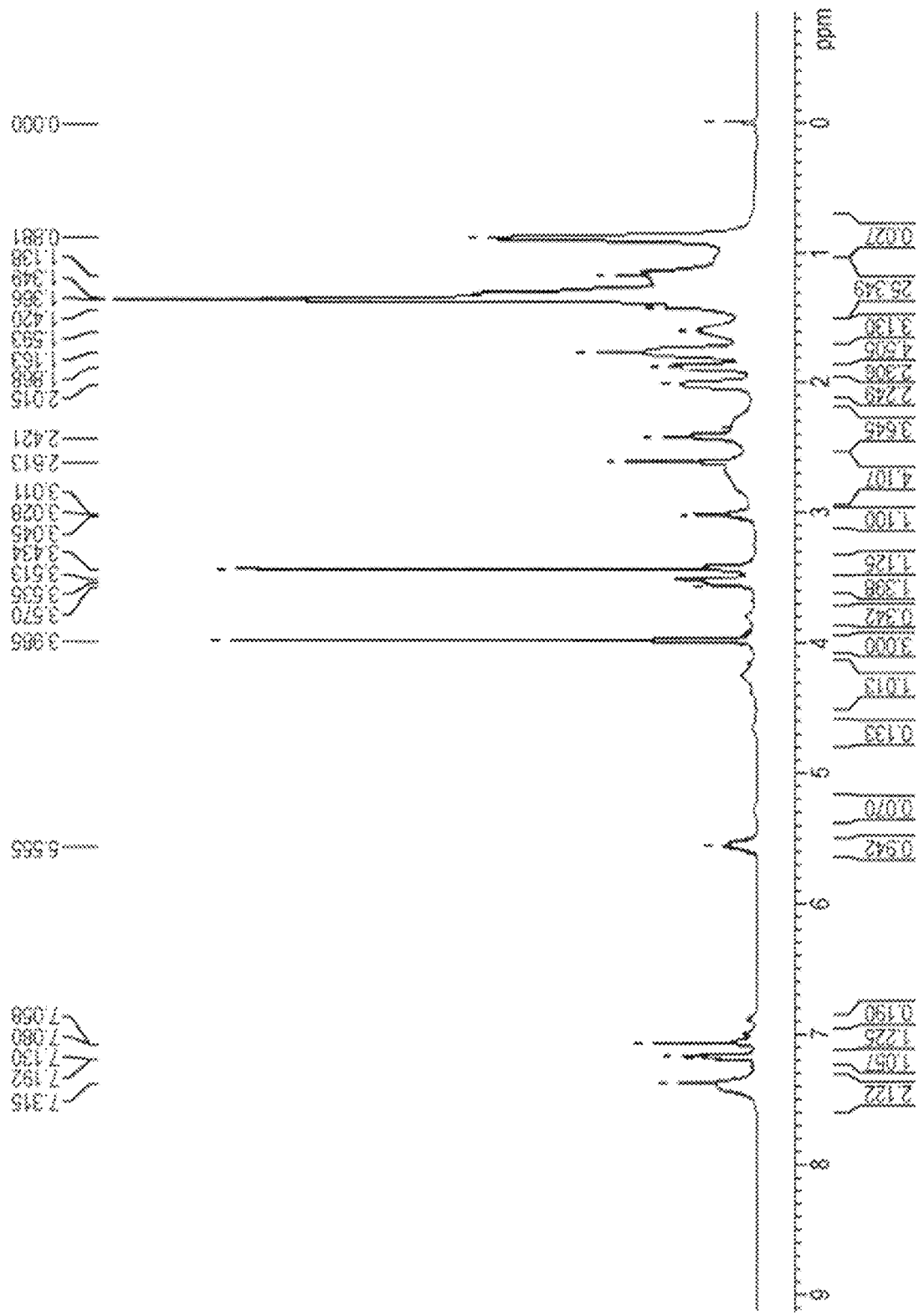
FIG. 2 is a $^1$H NMR spectrum of Pd(π-allyl)(BrettPhos)Cl.

Following the representative procedure: [(allyl)PdCl]$_2$ (502 mg, 1.38 mmol); BrettPhos (1.48 g, 2.76 mmol); toluene (6 mL); 1 h. Product obtained as an off-white solid (1.95 g, 99%); $^1$H NMR (400 MHz, CDCl$_3$, δ): complex spectrum (see FIG. 2); $^{31}$P NMR (162 MHz, CDCl$_3$, δ): 54.1, 48.7; Anal. calcd. for C$_{38}$H$_{58}$O$_2$ClPPd: C, 63.42; H, 8.12. Found C, 63.17; H, 8.16.

Pd(π-Crotyl)(BrettPhos)Cl

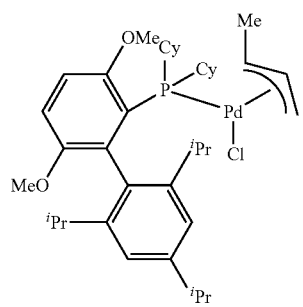

Figure 3:
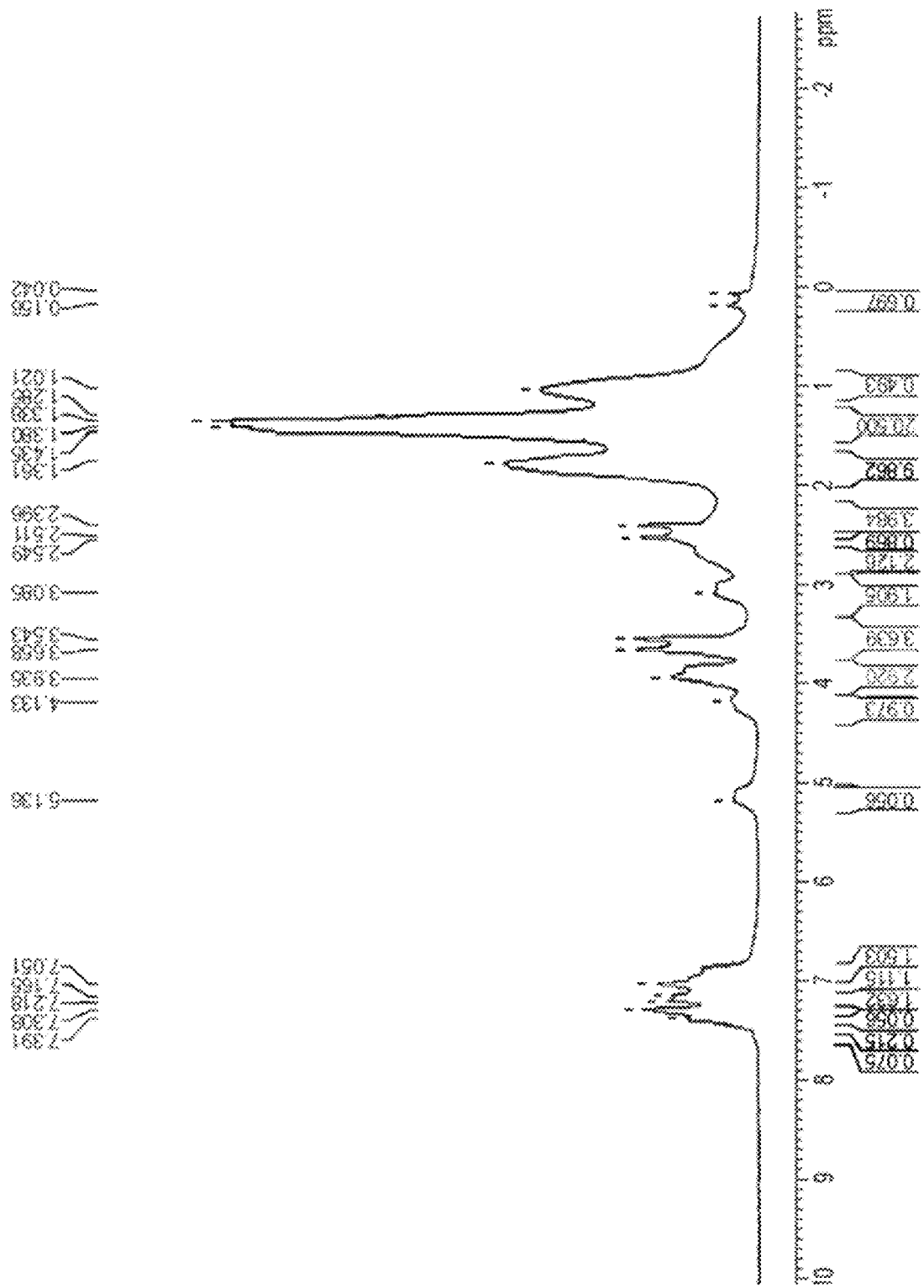
FIG. 3 is a $^1$H NMR spectrum of Pd(π-crotyl)(BrettPhos)Cl.

Following the representative procedure: [(crotyl)PdC]₂ (303 mg, 0.769 mmol); BrettPhos (827 mg, 1.53 mmol); toluene (2 mL); 1 h. Product obtained as an off-white solid (1.04 g, 92%); ¹H NMR (400 MHz, CDCl₃, δ): complex spectrum (see FIG. 3); ³¹P NMR (162 MHz, CDCl₃, δ): 41.4; Anal. calcd. for C₃₉H₆₀O₂ClPPd: C, 63.84; H, 8.24. Found C, 65.01; H, 8.57.

Pd(π-Cinnamyl)(BrettPhos)Cl

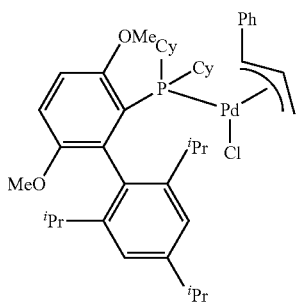

Figure 4:
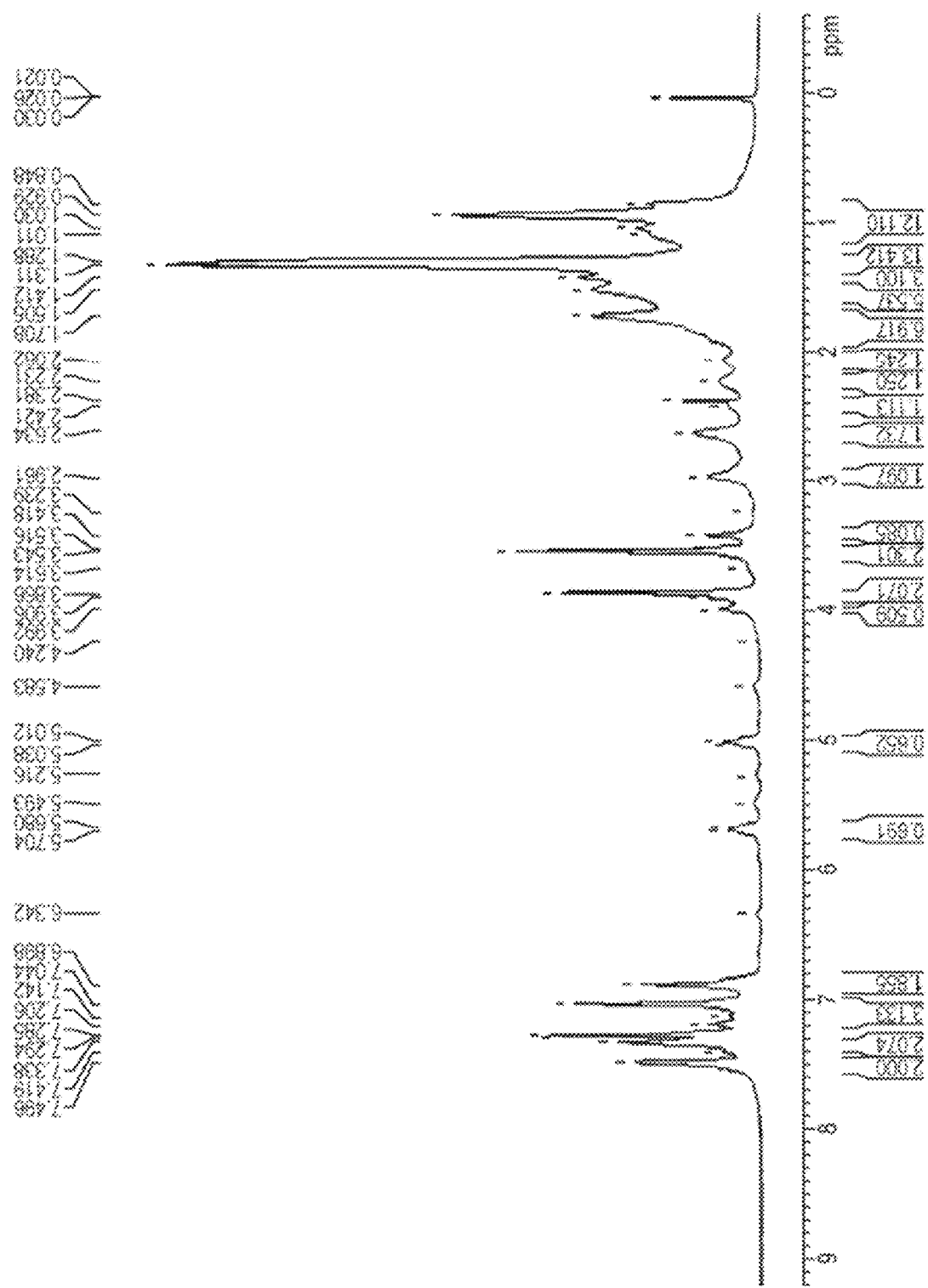
FIG. 4 is a $^1$H NMR spectrum of Pd(π-cinnamyl)(BrettPhos)Cl.

Following the representative procedure: [(cinnamyl)PdC]₂ (503 mg, 0.971 mmol); BrettPhos (1.04 g, 1.94 mmol); toluene (4 mL); 0.5 h. Product obtained as a yellow solid (1.34 g, 87%); ¹H NMR (400 MHz, CDCl₃, δ): complex spectrum (see FIG. 4); ³¹P NMR (162 MHz, CDCl₃, δ): 43.9; Anal. calcd. for C₄₄H₆₂O₂ClPPd: C, 66.41; H, 7.85. Found C, 66.44; H, 8.15.

Pd(π-Allyl)(JackiePhos)Cl

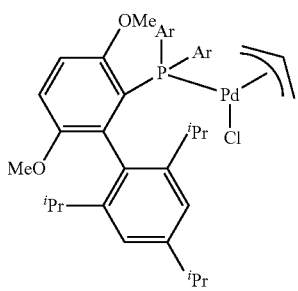

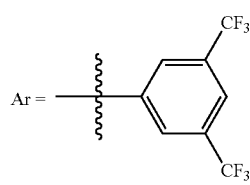

Figure 5:
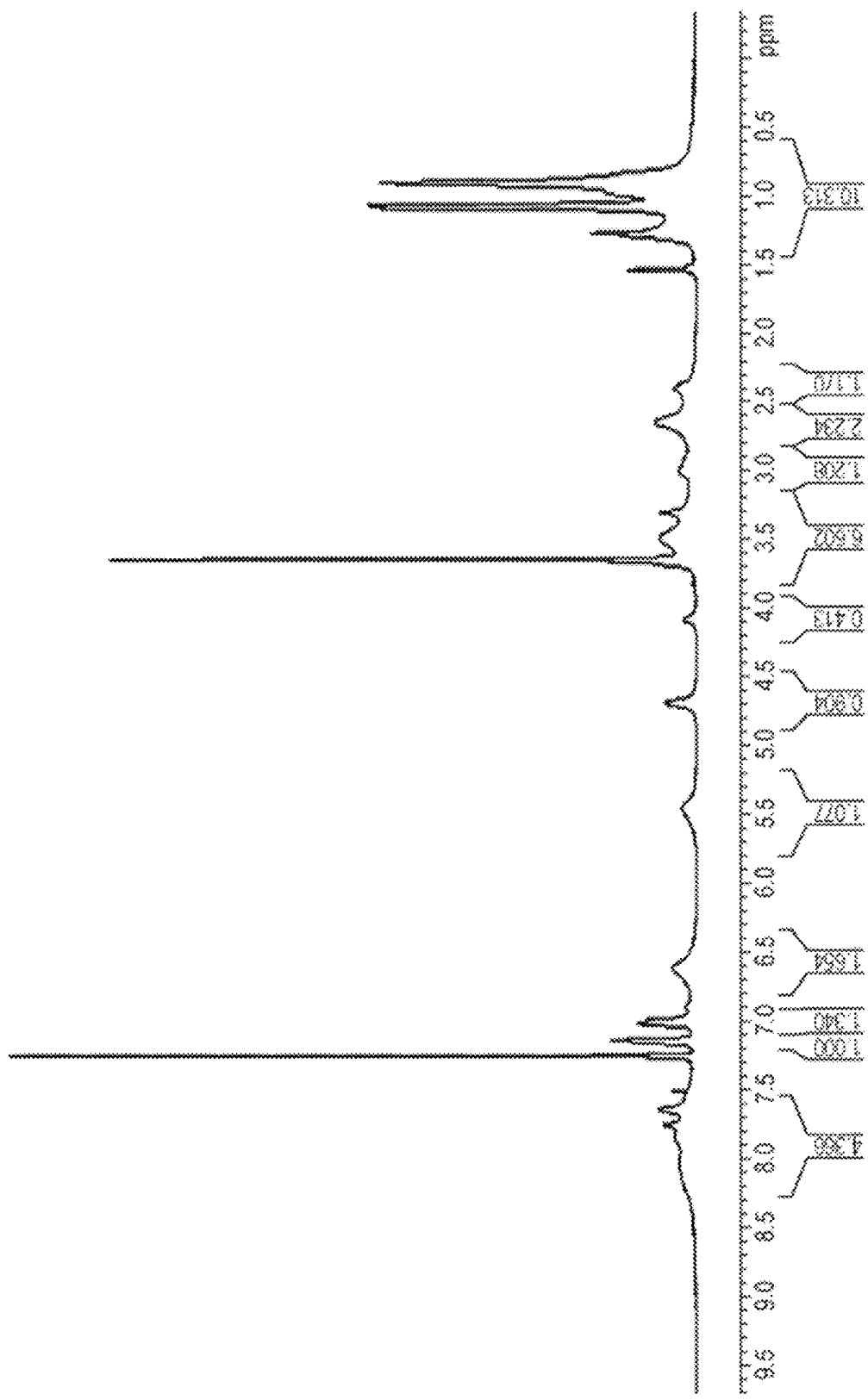
FIG. 5 is a $^1$H NMR spectrum of Pd(π-allyl)(JackiePhos)Cl.

Following the representative procedure: [(allyl)PdC]₂ (183 mg, 0.500 mmol); JackiePhos (797 mg, 1.00 mmol); toluene (5 mL); 1 h. Product obtained as a white solid (529 mg, 54%); ¹H NMR (400 MHz, CDCl₃, δ): complex spectrum (see FIG. 5); ³¹P NMR (162 MHz, CDCl₃, δ): 18.1; Anal. calcd. for C₄₂H₄₂F₁₂O₂ClPPd: C, 51.50; H, 4.32. Found C, 51.52; H, 4.15.

Pd(π-Allyl)(CyBippyPhos)Cl

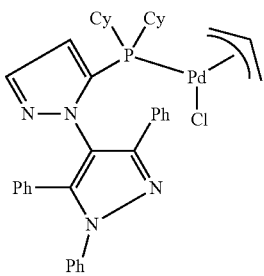

Following the representative procedure: [(allyl)PdC]₂ (245 mg, 0.671 mmol); CyBippyPhos (750 mg, 1.34 mmol); THF (4.5 mL); 0.5 h. Product obtained as a pale yellow solid (220 mg, 22%).

Pd(π-allyl)(CyBippyPhos)Cl may also be prepared by the following procedure:

A dry 20 mL scintillation vial is charged with 245 mg (0.67 mmol) of [(allyl)PdCl]₂ and transferred into a nitrogen-filled glove box. The vial is then charged with 750 mg (1.34 mmol) of CyBippyPhos. 4 mL of toluene is added and the mixture is stirred at rt for 30 minutes. During the stir time, the mixture becomes thick and stirring is difficult. An additional 4 mL of toluene is added to allow stirring to continue. The product is fully precipitated by the addition of 8 mL of hexanes. The solid is collected by vacuum filtration in air and washed with 3×10 mL of hexanes. The solid is dried in vacuo to give 913 mg (1.23 mmol, 92%) of the title compound as an off-white solid. The product contains <2 wt % of residual toluene.

¹H NMR (400 MHz, CDCl₃, δ): 7.99 (s, 1H), 7.44-7.18 (m, 15H), 6.68-6.55 (m, 1H), 5.30-4.99 (m, 1H), 4.60-4.50 (m, 1H), 3.54-3.33 (m, 1H), 2.88-2.78 (m, 1H), 2.20-0.77 (m, 22H), 0.48-0.30 (m, 1H); ³¹P NMR (162 MHz, CDCl₃, δ): 25.2, 23.2; HRMS-ESI m/z: [M−Cl], calcd. for C₃₇H₅₈PPd, 637.3154; found 637.3153. Anal. calcd. for C₃₉H₄₄N₄ClPPd: C, 63.16; H, 5.98; N, 7.55. Found C, 63.22; H, 6.14; N, 7.30.

(π-Crotyl)Pd(CyBippyPhos)Cl

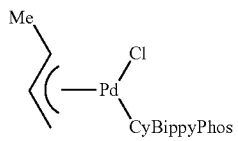

A dry Schlenk flask is charged with 264 mg (0.67 mmol) of [(crotyl)PdCl]₂ and transferred into a nitrogen-filled glove box. The flask is then charged with 750 mg (1.34 mmol) of CyBippyPhos. 8 mL of toluene is added and the mixture is stirred at rt for 1 hour. The product is precipitated by the addition of 20 mL of pentane with cooling in an ice bath. The solid is collected by vacuum filtration in air, washed with 3×10 mL of hexanes, and dried in vacuo to give 904 mg (1.10 mmol, 83%) of the title compound as an off-white solid. The product is a ⅔ toluene adduct, which is broken by the dissolution in CH₂Cl₂ and evaporating the solvent under reduced pressure at 60° C.

Figure 6:
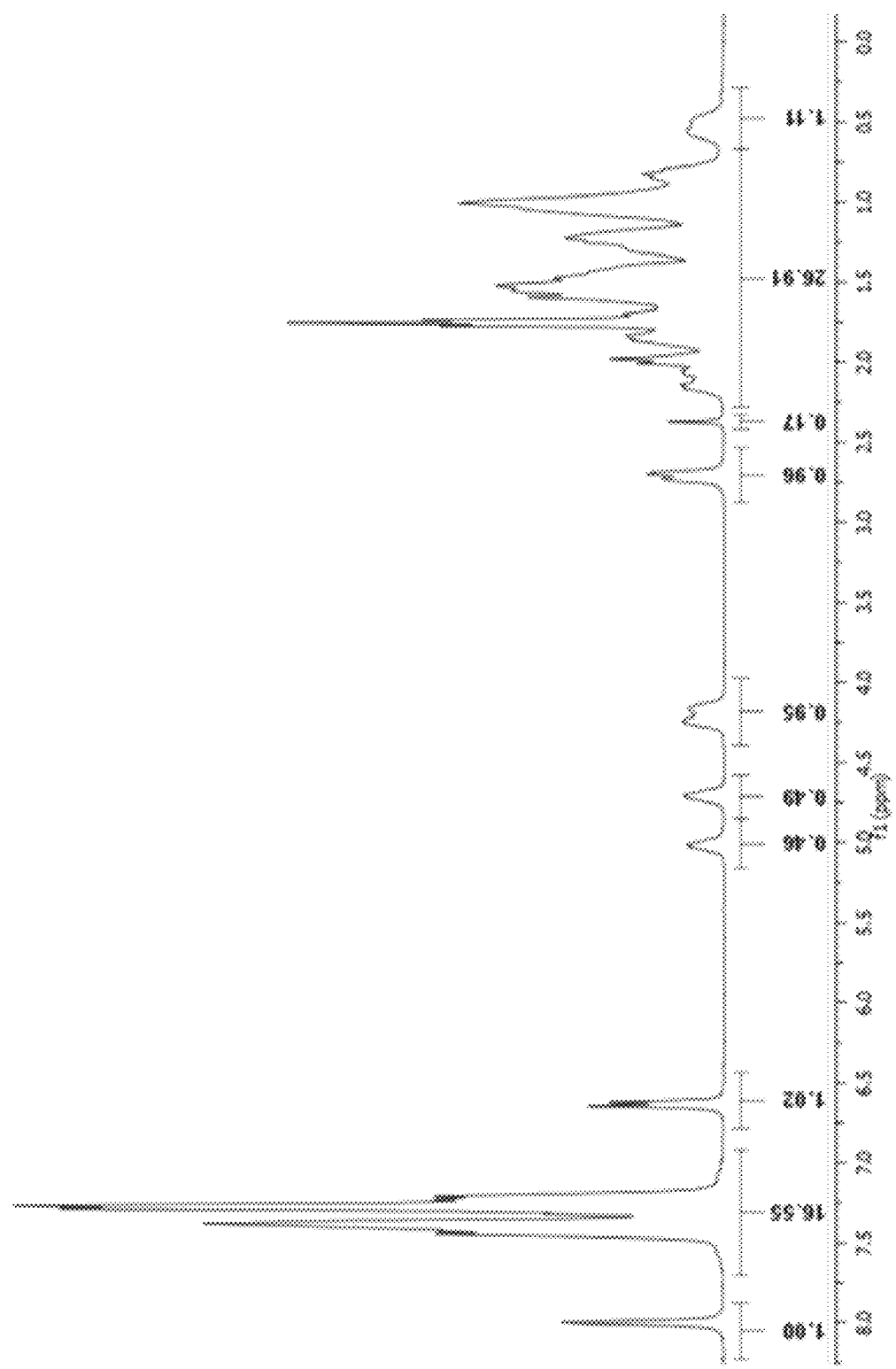
FIG. 6 is a $^1$H NMR spectrum of (π-crotyl)Pd(CyBippyPhos)Cl.

¹H NMR (400 MHz, CDCl₃, δ): complex spectrum (see FIG. 6).

¹³C NMR (101 MHz, CDCl₃, δ): 147.2, 142.2, 142.0, 140.5, 140.4, 140.0, 139.9, 137.9, 137.6, 137.3, 137.1, 131.4, 131.3, 130.4, 129.1 (2 peaks), 129.0, 128.7, 128.6 (2 peaks), 128.5, 128.2 (2 peaks), 127.6, 127.5, 126.2 (2 peaks), 126.1, 125.3, 120.1, 119.8, 116.9, 116.8, 116.4, 116.3, 115.8 (2 peaks), 115.3 (2 peaks), 100.9, 100.6, 100.4, 52.0, 50.6, 34.9, 34.7, 34.4, 34.1, 30.6, 29.9 (2 peaks), 29.6, 29.5, 28.5, 28.3, 27.9, 27.7, 27.2, 27.0, 26.9, 26.8, 26.7, 26.6, 26.0, 25.8, 22.4, 21.5 [Observed complexity due to C—P coupling].

³¹P NMR (162 MHz, CDCl₃, δ): 22.6 (br), 19.8 (br).

HRMS (ESI) m/z [M−Cl]⁺ Calcd. for $C_{40}H_{46}NPPd$: 719.2495; Found: 719.2510.

Example 2 (Comparative)

Arylation of Acetophenone with 4-Chloroanisole

Example 3 (According to the Invention)

Arylation of Acetophenone with 4-Chloroanisole

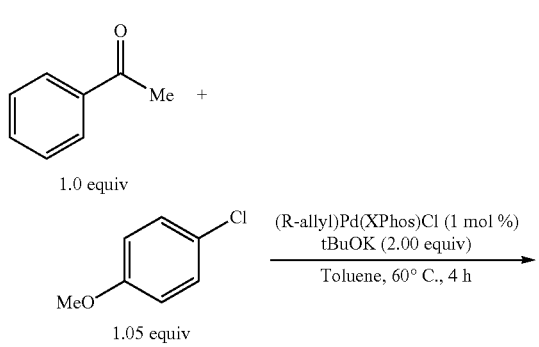

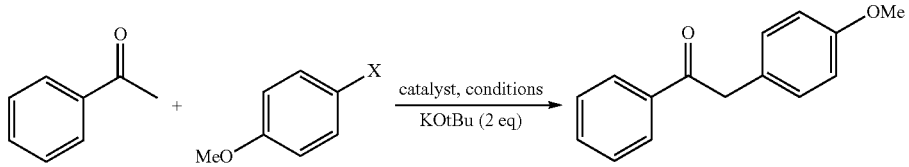

| catalyst | X | solvent | TC | time (h) | dierylated:mono: acetophenone^a | remarks |
|---|---|---|---|---|---|---|
| 1 mol % 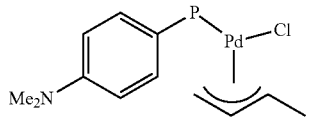 | t-Bu₂ Br | toluene (0.25 M) | 40 | 18 | 11%:81%:7% | 1.2:1.0 acetophenone:aryl chloride, isolated yield 60% |
|  | Br | toluene (0.25 M) | 40 | 18 | 1%:65%:33% |  |
|  | Cl | toluene (0.25 M) | 60 | 18 | 0%:37%:63% |  |
|  | Cl | toluene (0.25 M) | 60 | 18 | 0%:46%:54% | 1.2:1.0 acetophenone:aryl chloride 2.5 eq KOt-Bu |
|  | Cl | toluene (0.25 M) | 60 | 18 | 0%:36%:64% |  |
| 1 mol % | t-Bu₂ Cl | toluene (0.25 M) | 40 | 18 | 39%:37%:61% |  |

^a NMR ratios

Representative Procedure: A dry Schlenk tube equipped with a teflon-coated magnetic stir bar is charged with 1 mol % (0.01 mmol) of Pd-precatalyst and 2.00 mmol (2.0 equiv) of t-BuOK. The tube is fitted with a rubber septum and is evacuated and backfilled with nitrogen. This evacuation/backfill procedure is repeated two additional times. 4-Chloroanisole (1.00 mmol, 1 equiv) and acetophenone (1.20 mmol, 1.2 equiv) are added via syringe followed by 4 mL of anhydrous toluene. The tube is placed in a preheated (40-60° C.) oil bath and the mixture is stirred vigorously for 18 h. The tube is then removed from the oil bath and the contents are allowed to cool to room temperature. A sample of the crude reaction mixture is analysed by ¹H NMR.

-continued

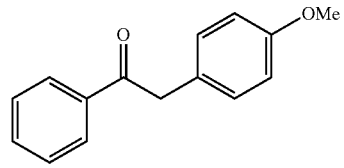

R = H: 88% Isolated
>20:1 monoarylation:diarylation (GC)
R = Me: 85% (GC)
>20:1 monoarylation:diarylation (GC)
R = Ph: 83% (GC)
>20:1 monoarylation:diarylation (GC)

Representative Procedure: A dry Schlenk tube equipped with a teflon-coated magnetic stir bar is charged with 6.5 mg (0.01 mmol) of (R-allyl)Pd(XPhos)Cl and 224 mg (2.00 mmol) of t-BuOK. The tube is fitted with a rubber septum and is evacuated and backfilled with nitrogen. This evacuation/backfill procedure is repeated two additional times. 4-Chloroanisole (129 µL, 1.05 mmol) and acetophenone (117 µL, 1.00 mmol) are added via syringe followed by 4 mL of anhydrous toluene. The tube is placed in a preheated (60° C.) oil bath and the mixture is stirred vigorously for 4 h. The tube is then removed from the oil bath and the contents are allowed to cool to room temperature. A sample is analysed by GC.

A common problem observed in the α-arylation of methyl ketones is the formation of diarylated products. The results of this Example indicate that significantly higher yields and higher selectivity (>20:1) for monoarylation:diarylation of acetophenone with chloroarenes are achieved using (R-allyl)Pd(XPhos)Cl complexes relative to (R-allyl)Pd(AmPhos)Cl complexes (see Example 2). It is important to note that it is the identity of the ligand which determines the catalyst's activity.

Example 4 (According to the Invention)

Amination of 4-Chloroanisole with Morpholine

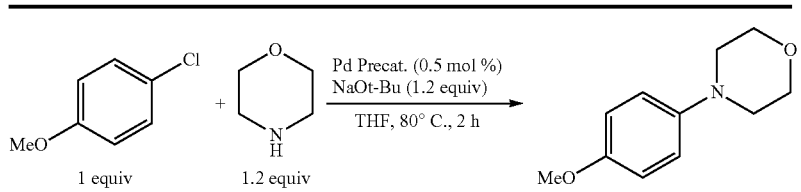

| Catalyst | GC Conversion[b] |
|---|---|
| **1st gen RuPhos PC | 66% |
| **2nd gen RuPhos PC | 4% |
| **3rd Gen RuPhos PC | 5% |
| (allyl)Pd(RuPhos)Cl | 80% |
| (crotyl)Pd(RuPhos)Cl | 87%/97%[c]/100%[c,d] |
| (cinnamyl)Pd(RuPhos)Cl | 95% |
| **1st gen RuPhos PC* | 6% |
| (crotyl)Pd(RuPhos)Cl* | 5% |

*with 0.5 mol % added carbazole

**comparative

PC = palladacycle

[a]Reaction conditions: 4-chloroanisole (1.0 mmol), morpholine (1.2 mmol), NaOtBu (1.2 mmol), catalyst (0.5 mol %), THF (2 mL).

[b]Determined by GC using dodecane as an internal standard.

[c]With 0.5 mol % additional RuPhos added.

[d]Run for 2.5 h.

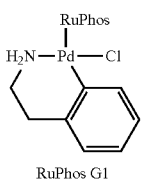

RuPhos G1

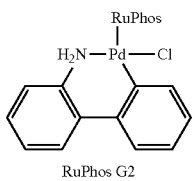

RuPhos G2

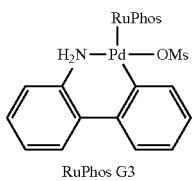

RuPhos G3

The above data demonstrate that the (R-π-allyl)Pd(L)Cl (L=RuPhos) complexes of the present invention exhibit better activity than the first generation RuPhos palladacycle and significantly better activity than the second and third generation RuPhos palladacycles.

Moreover, the second and third generation Buchwald palladacycle precatalysts release an equivalent of genotoxic carbazole upon activation, unlike the complexes of the present invention. The above data also show that the active catalyst generated from (R-π-allyl)Pd(L)Cl complexes does not suffer from inhibition due to carbazole formation, as do the second and third generation palladacycles.

Example 5 (According to the Invention)

Suzuki-Miyaura Coupling of 3-Chloropyridine and p-Tolylboronic Acid[a]

| Precatalyst | GC Conversion |
|---|---|
| *3rd gen XPhos palladacycle | 65% |
| (Allyl)Pd(XPhos)Cl | 68% |
| (Crotyl)Pd(XPhos)Cl | 91%/100%[b] |
| (Cinnamyl)Pd(XPhos)Cl | 90% |

*comparative.
[a]Reaction conditions: 3-Chloropyridine (1.0 mmol), p-tolylboronic acid (1.5 mmol), $K_3PO_4$ (2.0 mmol), catalyst (2 mol %), THF (2 mL), $H_2O$ (4 mL).
[b]Run for 2 h.

3rd generation XPhos palladacycle

A dry Schlenk tube, equipped with a Teflon-coated magnetic stir bar and fitted with a rubber septum, is charged with the precatalyst (0.02 mmol, 2 mol %) and 204 mg (1.50 mmol, 1.50 equiv) of p-tolylboronic acid. The tube is evacuated and backfilled with nitrogen. This evacuation/backfill cycle is repeated two additional times. 3-Chloropyridine (95 μL, 1.00 mmol, 1.00 equiv) is added followed by 2 mL of anhydrous THF and 4.0 mL of 0.5 M $K_3PO_4$ (aqueous). The contents are stirred vigorously for 30 min. An aliquot is removed and analyzed by gas chromatography.

The (allyl)Pd(XPhos)Cl complex exhibits comparable conversion to the 3rd generation XPhos palladacycle. However, both (crotyl)Pd(XPhos)Cl and (cinnamyl)Pd(XPhos)Cl promote the Suzuki-Miyaura coupling reaction with higher rates than the 3rd generation palladacycle.

Example 6 (According to the Invention)

Amination of Aryl/Heteroaryl Chlorides Using (π-Crotyl)Pd(RuPhos)Cl[a]

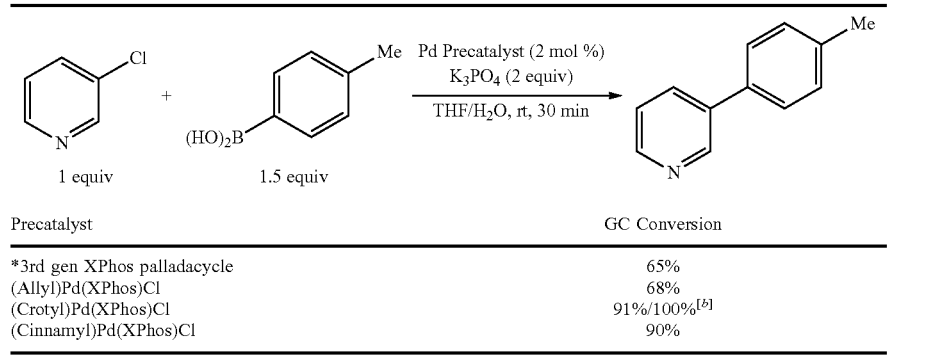

96%

-continued

95%

-continued

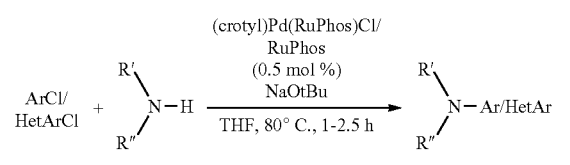

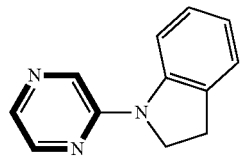

97%

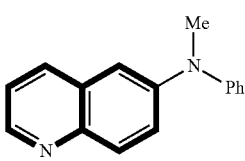

99%

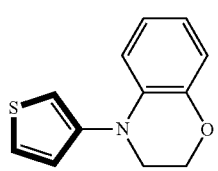

98%[b]

[a]Reaction conditions: ArCl/HetArCl (1.0 mmol), amine (1.2 mmol), NaOtBu (1.2 mmol), catalyst (0.5 mol %), RuPhos (0.5 mol %), THF (2 mL).
[b]1 mol % (π-crotyl)Pd(RuPhos)Cl/1 mol % RuPhos, K$_2$CO$_3$, t-AmOH, 110° C., 18 h.

Fast reaction times were observed with 100% conversion reached with 1-2.5 h in all cases with the exception of 4-(thiophen-3-yl)-3,4-dihydro-2H-benzo[b][1,4]oxazine, which required 18 h. The synthesis of 4-(thiophen-3-yl)-3,4-dihydro-2H-benzo[b][1,4]oxazine also demonstrates catalyst activation with the use of a weak base (K$_2$CO$_3$), compared to NaOt-Bu.

General Procedure for the Amination Reactions

An oven dried Schlenk tube equipped with a Teflon-coated magnetic stir bar is charged with (π-crotyl)Pd(RuPhos)Cl (0.5-1 mol % as indicated), RuPhos (0.5-1 mol % as indicated), aryl chloride (1.00 mmol, if solid), and NaOt-Bu (1.20 mmol). The tube is evacuated and backfilled with nitrogen. This evacuation/backfill cycle is repeated two additional times. Dodecane (GC standard, 0.20 mmol), the amine (1.20 mmol), aryl chloride (1.00 mmol, if liquid), and anhydrous THF (2 mL) are added sequentially via syringe. The tube is placed in a preheated oil bath and stirred for the indicated time. The tube is then removed from the oil bath and allowed to cool to room temperature. The reaction mixture is diluted with 10 mL of EtOAc and filtered through a pad of Celite. The solution is concentrated in vacuo and the residue is chromatographed on silica gel using a Teledyne ISCO CombiFlashRf.

4-(4-methoxyphenyl)morpholine

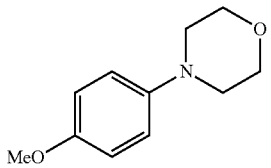

According to the general procedure, a mixture of 4-chloroanisole (123 μL, 1.00 mmol), morpholine (105 μL, 1.20 mmol), NaOtBu (115 mg, 1.20 mmol), (π-crotyl)Pd(RuPhos)Cl (3.3 mg, 0.005 mmol), RuPhos (2.3 mg, 0.005 mmol), and 2 mL THF are stirred at 80° C. for 2.5 h. The crude material is chromatographed on silica gel with a gradient of 0-20% EtOAc/hexanes as the eluent to give 186 mg (0.96 mmol, 96%) of 4-(4-methoxyphenyl)morpholine as a colorless solid. The spectroscopic data match those previously reported (D. Maiti, B. P. Fors, J. L. Henderson, Y. Nakamura, S. L. Buchwald, Chem. Sci. 2011, 2, 57).

N,N-Diethyl-6-Methoxypyridin-2-Amine

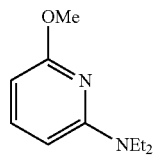

According to the general procedure, a mixture of 2-chloro-6-methoxypyridine (119 μL, 1.00 mmol), diethylamine (124 μL, 1.20 mmol), NaOtBu (115 mg, 1.20 mmol), (π-crotyl)Pd(RuPhos)Cl (3.3 mg, 0.005 mmol), RuPhos (2.3 mg, 0.005 mmol), and 2 mL THF are stirred at 80° C. for 70 minutes. The crude material is chromatographed on silica gel with a gradient of 0-5% EtOAc/hexanes as the eluent to give 171 mg (0.95 mmol, 95%) of N,N-diethyl-6-methoxypyridin-2-amine as a colorless oil.

$^1$H NMR (400 MHz, CDCl$_3$, δ): 7.33 (t, J=7.5 Hz, 1H), 5.99 (d, J=7.8 Hz, 1H), 5.93 (d, J=7.8 Hz, 1H), 3.86 (s, 3H), 3.49 (q, J=7.0 Hz, 4H), 1.81 (t, J=7.0 Hz, 6H).

$^{13}$C NMR (100 MHz, CDCl$_3$, δ): 163.4, 156.7, 139.8, 96.8, 95.2, 52.9, 42.7, 13.2.

HRMS (ESI) m/z [M+H]$^+$ Calcd. for C$_{10}$H$_{17}$N$_2$O: 181.1341. Found: 181.1318.

1-(Pyrazin-2-Yl)Indoline

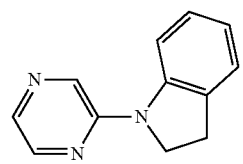 [SMILES: c1ccc2c(c1)CCN2c1cnccn1]

According to the general procedure, a mixture of 2-chloropyrazine (89 μL, 1.00 mmol), indoline (135 μL, 1.20 mmol), NaOtBu (115 mg, 1.20 mmol), (π-crotyl)Pd(RuPhos)Cl (3.3 mg, 0.005 mmol), RuPhos (2.3 mg, 0.005 mmol), and 2 mL THF are stirred at 80° C. for 1 hour. The crude material is chromatographed on silica gel with a gradient of 0-50% EtOAc/hexanes as the eluent to give 191 mg (0.97 mmol, 97%) of 1-(pyrazin-2-yl)indoline as a yellow solid.

$^1$H NMR (400 MHz, CDCl$_3$, δ): 8.14-8.28 (m, 3H), 8.00 (app d, J=2.6 Hz, 1H), 7.13-7.27 (m, 2H), 6.88-6.93 (m, 1H), 4.05 (t, J=8.7 Hz, 2H), 3.24 (t, J=8.7 Hz, 2H).

$^{13}$C NMR (100 MHz, CDCl$_3$, δ): 151.6, 144.1, 141.8, 134.3, 132.0, 131.3, 127.5, 124.8, 121.6, 114.2, 48.7, 27.9.

Anal. Calcd. for C$_{12}$H$_{11}$N$_3$: C, 73.07; H, 5.62; N, 21.30. Found: C, 73.17; H, 5.63; N, 21.42.

N-methyl-N-phenylquinolin-6-amine

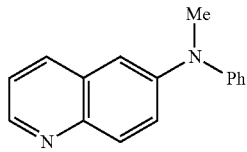 [SMILES: CN(c1ccccc1)c1ccc2ncccc2c1]

According to the general procedure, a mixture of 6-chloroquinoline (164 mg, 1.00 mmol), N-methylaniline (130 μL, 1.20 mmol), NaOtBu (115 mg, 1.20 mmol), (π-crotyl)Pd(RuPhos)Cl (3.3 mg, 0.005 mmol), RuPhos (2.3 mg, 0.005 mmol), and 2 mL THF are stirred at 80° C. for 1 hour. The crude material is chromatographed on silica gel with a gradient of 0-50% EtOAc/hexanes as the eluent to give 231 mg (0.99 mmol, 99%) of N-methyl-N-phenylquinolin-6-amine as a yellow oil. The spectroscopic data match those previously reported (M. Tobisu, A. Yasutome, K. Yamakawa, T. Shimasaki, N. Chatani, *Tetrahedron* 2012, 68, 5157).

4-(thiophen-3-yl)-3,4-dihydro-2H-benzo[b][1,4]oxazine

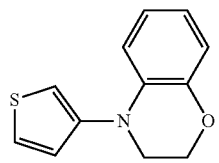 [SMILES: c1ccc2c(c1)OCCN2c1ccsc1]

The general procedure is followed with the following modifications: a mixture of 3-chlorothiophene (93 μL, 1.00 mmol), benzomorpholine (140 μL, 1.20 mmol), K$_2$CO$_3$ (194 mg, 1.40 mmol), (π-crotyl)Pd(RuPhos)Cl (6.6 mg, 0.01 mmol), RuPhos (4.7 mg, 0.01 mmol), and 2 mL t-AmOH are stirred at 110° C. for 20 hour. The crude material is chromatographed on silica gel with a gradient of 0-5% EtOAc/hexanes as the eluent to give 212 mg (0.98 mmol, 98%) of 4-(thiophen-3-yl)-3,4-dihydro-2H-benzo[b][1,4]oxazine as a yellow oil.

$^1$H NMR (400 MHz, CDCl$_3$, δ): 7.30 (dd, J=3.2 Hz, 5.2 Hz, 1H), 7.07 (dd, J=1.4 Hz, 5.2 Hz, 1H), 6.92-6.98 (m, 1H), 6.85-6.91 (m, 1H), 6.81 (dd, J=1.4 Hz, 3.2 Hz, 1H), 6.73-6.81 (m, 2H), 4.33 (t, J=4.5 Hz, 2H), 3.69 (t, J=4.4 Hz, 2H).

$^{13}$C NMR (100 MHz, CDCl$_3$, δ): 146.1, 144.5, 133.1, 125.4, 124.1, 121.2, 120.1, 117.0, 116.3, 112.3, 64.5, 49.0.

Anal. Calcd. for C$_{12}$H$_{11}$NOS: C, 66.33; H, 5.10; N, 6.45. Found: C, 66.42; H, 5.24; N, 6.42.

Example 7 (According to the Invention)

Suzuki-Miyaura Reactions Using (π-Crotyl)Pd(XPhos)Cl[a]

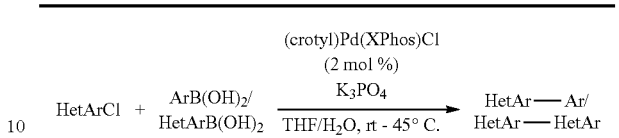

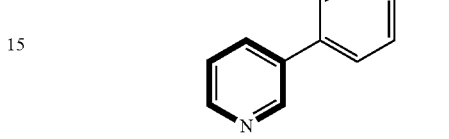

95%
rt, 2 h

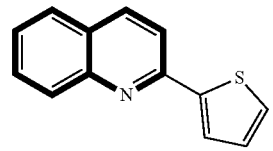

98%
45° C., 1 h

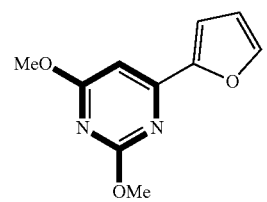

94%
rt, 1 h

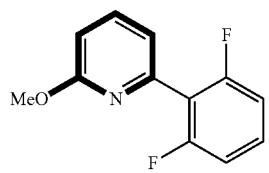

88%
rt, 30 min

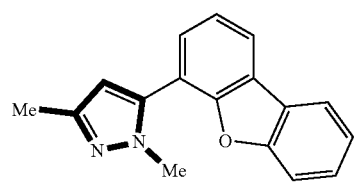

-continued

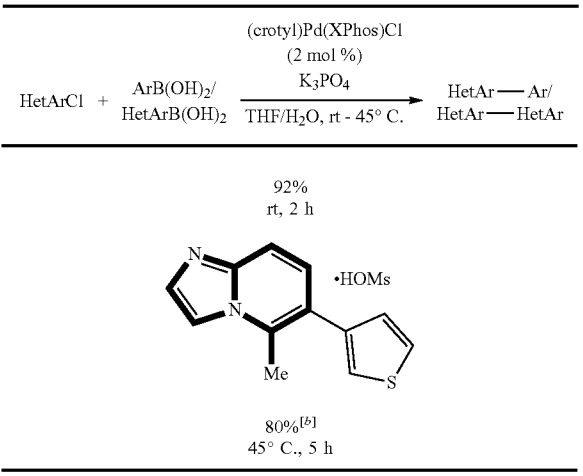

[a]Reaction conditions: HetArCl (1.0 mmol), ArB(OH)₂ (1.5 mmol), K₃PO₄ (2.0 mmol), catalyst (2 mol %), THF (2 mL), H₂O (4 mL).
[b]Isolated as the hydromethanesulfonate salt for ease of purification.

Using (crotyl)Pd(XPhos)Cl catalyst, a range of heteroaryl chlorides may be coupled with challenging aryl and heteroaryl boronic acids with uniformly high yields, including those which are prone to rapid protodeboronation, at or slightly above room temperature (up to 45° C.) due to the fast generation of the active "L-Pd(0)". For example, 2-thienylboronic acid, 2-furanboronic acid, and 2,6-difluorophenylboronic acid were all coupled in high yield with short reaction times (≤1 hour).

[a] Reaction conditions: HetArCl (1.0 mmol), ArB(OH)₂ (1.5 mmol), K₃PO₄ (2.0 mmol), catalyst (2 mol %), THF (2 mL), H₂O (4 mL). [b] Isolated as the hydromethanesulfonate salt for ease of purification.

General Procedure for the Suki-Miyaura Couplings

An oven dried Schlenk tube equipped with a Teflon-coated magnetic stir bar is charged with (π-crotyl)Pd(XPhos)Cl (2 mol %), heteroaryl chloride (1.00 mmol, if solid), and aryl/heteroarylboronic acid (1.5 mmol). The tube is evacuated and backfilled with nitrogen. This evacuation/backfill cycle is repeated two additional times. The heteroaryl chloride (1.00 mmol, if liquid), anhydrous THF (2 mL), and aqueous 0.5 M K₃PO₄ (4.0 mL) are added sequentially via syringe. The tube is stirred at room temperature or placed in a preheated oil bath at 45° C. as indicated and stirred for the indicated time. If heated, the tube is then removed from the oil bath and allowed to cool to room temperature. The reaction mixture is diluted with 10 mL of EtOAc and 10 mL of H₂O, and then the aqueous phase is extracted with 3×10 mL of EtOAc. The combined organic extracts are dried over anhydrous MgS₄, filtered, and concentrated in vacuo. The residue is chromatographed on silica gel using a Teledyne ISCO CombiFlashRf, unless otherwise noted.

3-(4-tolyl)pyridine

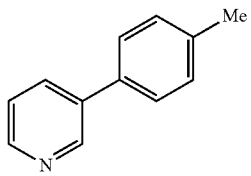 [SMILES: Cc1ccc(-c2cccnc2)cc1]

According to the general procedure, a mixture of 3-chloropyridine (95 μL, 1.00 mmol), p-tolylboronic acid (204 mg, 1.50 mmol), (π-crotyl)Pd(XPhos)Cl (14 mg, 0.02 mmol), 2 mL THF, and 4 mL of 0.5 M aqueous K₃PO₄ are stirred at room temperature for 2 hours. The crude material is chromatographed on silica gel with a gradient of 10-40% EtOAc/hexanes as the eluent to give 160 mg (0.95 mmol, 95%) of 3-(4-tolyl)pyridine as a colorless solid. The spectroscopic data match those previously reported (C. L. Cioffi, W. T. Spencer, J. J. Richards, R. J. Herr, *J. Org. Chem.* 2004, 69, 2210).

2-(thiophen-2-yl)quinoline

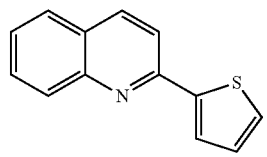 [SMILES: c1csc(-c2ccc3ccccc3n2)c1]

According to the general procedure, a mixture of 2-chloroquinoline (164 mg, 1.00 mmol), 2-thienylboronic acid (192 mg, 1.50 mmol), (π-crotyl)Pd(XPhos)Cl (14 mg, 0.02 mmol), 2 mL THF, and 4 mL of 0.5 M aqueous K₃PO₄ are stirred at 45° C. for 2 hours. The crude material is chromatographed on silica gel with a gradient of 0-5% EtOAc/hexanes as the eluent to give 208 mg (0.99 mmol, 99%) of 2-(thiophen-2-yl)quinoline as a colorless solid. The spectroscopic data match those previously reported (F.-F. Zhuo, W.-W. Xie, Y.-X. Yang, L. Zhang, P. Wang, R. Yuan, C.-S. Da, *J. Org. Chem.* 2013, 76, 3243).

4-(furan-2-yl)-2,6-dimethoxypyrimidine

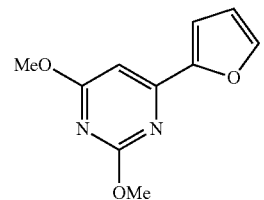 [SMILES: COc1cc(-c2ccco2)nc(OC)n1]

According to the general procedure, a mixture of 6-chloro-2,4-dimethoxypyrimidine (175 mg, 1.00 mmol), 2-furanboronic acid (168 mg, 1.50 mmol), (π-crotyl)Pd(XPhos)Cl (14 mg, 0.02 mmol), 2 mL THF, and 4 mL of 0.5 M aqueous K₃PO₄ are stirred at room temperature for 1 hour. The crude material is chromatographed on silica gel with a gradient of 0-10% EtOAc/hexanes as the eluent to give 194 mg (0.94 mmol, 94%) of 4-(furan-2-yl)-2,6-dimethoxypyrimidine as a colorless solid.

¹H NMR (400 MHz, CDCl₃, δ): 7.53 (dd, J=0.9 Hz, 1.9 Hz, 1H), 7.19 (dd, J=0.7 Hz, 3.5 Hz, 1H), 6.69 (s, 1H), 6.53 (dd, J=1.7 Hz, 3.4 Hz, 1H) 4.02 (s, 3H), 3.99 (s, 3H).

¹³C NMR (100 MHz, CDCl₃, δ): 172.6, 165.6, 157.4, 152.2, 144.6, 112.3, 111.9, 95.0, 54.8, 54.0.

Anal. Calcd. for C₁₀H₁₀N₂O₃: C, 58.25; H, 4.89; N, 13.59. Found: C, 58.19; H, 4.72; N, 13.42.

2-(2,6-difluorophenyl)-6-methoxypyridine

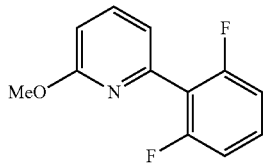 [SMILES: COc1cccc(-c2c(F)cccc2F)n1]

According to the general procedure, a mixture of 2-chloro-6-methoxypyridine (119 µL, 1.00 mmol), 2,6-difluorophenylboronic acid (237 mg, 1.50 mmol), (π-crotyl)Pd(XPhos)Cl (14 mg, 0.02 mmol), 2 mL THF, and 4 mL of 0.5 M aqueous $K_3PO_4$ are stirred at room temperature for 30 minutes. The crude material is chromatographed on silica gel with a gradient of 0-5% EtOAc/hexanes as the eluent to give 195 mg (0.88 mmol, 88%) of 2-(2,6-difluorophenyl)-6-methoxypyridine as a pale yellow oil.

$^1$H NMR (400 MHz, CDCl$_3$, δ): 7.64 (t, J=7.8 Hz, 1H), 7.35-7.26 (m, 1H), 7.05 (d, J=7.1 Hz, 1H), 7.00-6.92 (m, 2H), 6.75 (d, J=8.3 Hz, 1H), 3.95 (s, 3H).

$^{13}$C NMR (100 MHz, CDCl$_3$, δ): 163.8, 160.5 (dd, J=250.7 Hz, 6.97 Hz), 146.7, 138.6, 129.8 (t, J=10.23 Hz), 118.8 (t, J=1.95 Hz), 118.2 (t, J=17.23 Hz), 111.8 (dd, J=26.1 Hz, 6.6 Hz), 110.3, 53.6.

Anal. Calcd. for $C_{12}H_9F_2NO$: C, 65.16; H, 4.10; N, 6.33. Found: C, 65.14; H, 4.37; N, 6.46.

5-(dibenzo[b,d]furan-4-yl)-1,3-dimethyl-1H-pyrazole

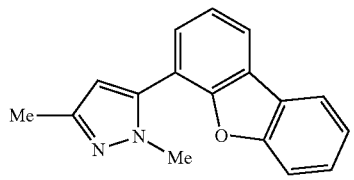 [SMILES: Cc1cc(-c2cccc3c2oc2ccccc23)n(C)n1]

According to the general procedure, a mixture of 5-chloro-1,3-dimethyl-1H-pyrazole (115 µL, 1.00 mmol), dibenzo[b]-furan-4-boronic acid (318 mg, 1.50 mmol), (π-crotyl)Pd(XPhos)Cl (14 mg, 0.02 mmol), 2 mL THF, and 4 mL of 0.5 M aqueous $K_3PO_4$ are stirred at room temperature for 2 hours. The crude material is chromatographed on silica gel with a gradient of 0-10% EtOAc/hexanes as the eluent to give 240 mg (0.92 mmol, 92%) of 5-(dibenzo[b,d]furan-4-yl)-1,3-dimethyl-1H-pyrazole as an off-white solid.

$^1$H NMR (400 MHz, CDCl$_3$, δ): 8.02-7.97 (m, 2H), 7.57 (d, J=8.8 Hz, 1H), 7.58-7.36 (m, 4H), 6.33 (s, 1H), 3.85 (s, 3H), 2.39 (s, 3H).

$^{13}$C NMR (100 MHz, CDCl$_3$, δ): 156.2, 153.3, 147.9, 139.1, 128.0, 127.7, 125.0, 124.0, 123.2, 123.0, 121.1, 120.9, 115.6, 112.0, 107.1, 37.4, 13.7.

Anal. Calcd. for $C_{17}H_4N_2O$: C, 77.84; H, 5.38; N, 10.68. Found: C, 77.93; H, 5.29; N, 10.56.

5-methyl-6-(thiophen-3-yl)imidazo[1,2-a]pyridine hydromethanesulfonate

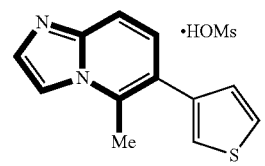

According to the general procedure, a mixture of 6-bromo-5-methylimidazo[1,2,a]pyridine (167 mg, 1.00 mmol), 3-thienylboronic acid (152 mg, 1.50 mmol), (π-crotyl)Pd(XPhos)Cl (14 mg, 0.02 mmol), 2 mL THF, and 4 mL of 0.5 M aqueous $K_3PO_4$ are stirred at 45° C. for 5 hours. The crude material is taken up in 10 mL of isopropyl acetate and stirred. 0.08 mL of methanesulfonic acid is added slowly as a precipitate developed, and the mixture is stirred at rt for 30 minutes. The solid is collected by vacuum filtration, washed (3×5 mL isopropyl acetate, 1×10 mL hexanes), and dried in vacuo to give 194 mg (0.80 mmol, 80%) of 5-methyl-6-(thiophen-3-yl)imidazo[1,2-a]pyridine hydromethanesulfonate as a tan solid.

$^1$H NMR (400 MHz, 4:1 D$_2$O/DMSO-d$_6$, δ): 8.18 (s, 1H), 8.06 (s, 1H), 7.97 (d, J=9.3 Hz, 1H), 7.85 (d, J=9.3 Hz, 1H), 7.70-7.60 (m, 2H), 7.32 (d, J=4.6 Hz, 1H), 2.87-2.77 (m, 6H).

$^{13}$C NMR (100 MHz, 4:1 D$_2$O/DMSO-d$_6$, δ): 140.4, 137.8, 137.3, 137.2, 130.1, 128.5, 127.3, 126.5, 123.9, 114.7, 110.4, 40.1, 17.4.

HRMS (ESI) m/z [M+H−OMs]$^+$ Calcd. for $C_{12}H_{10}N_2S$: 215.0643. Found: 215.0644.

Example 8 (According to the Invention)

Monoarylation of Ketone Enolates

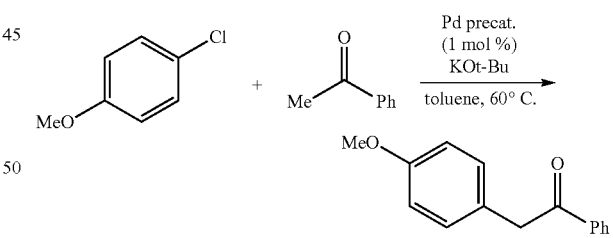

Figure 7:
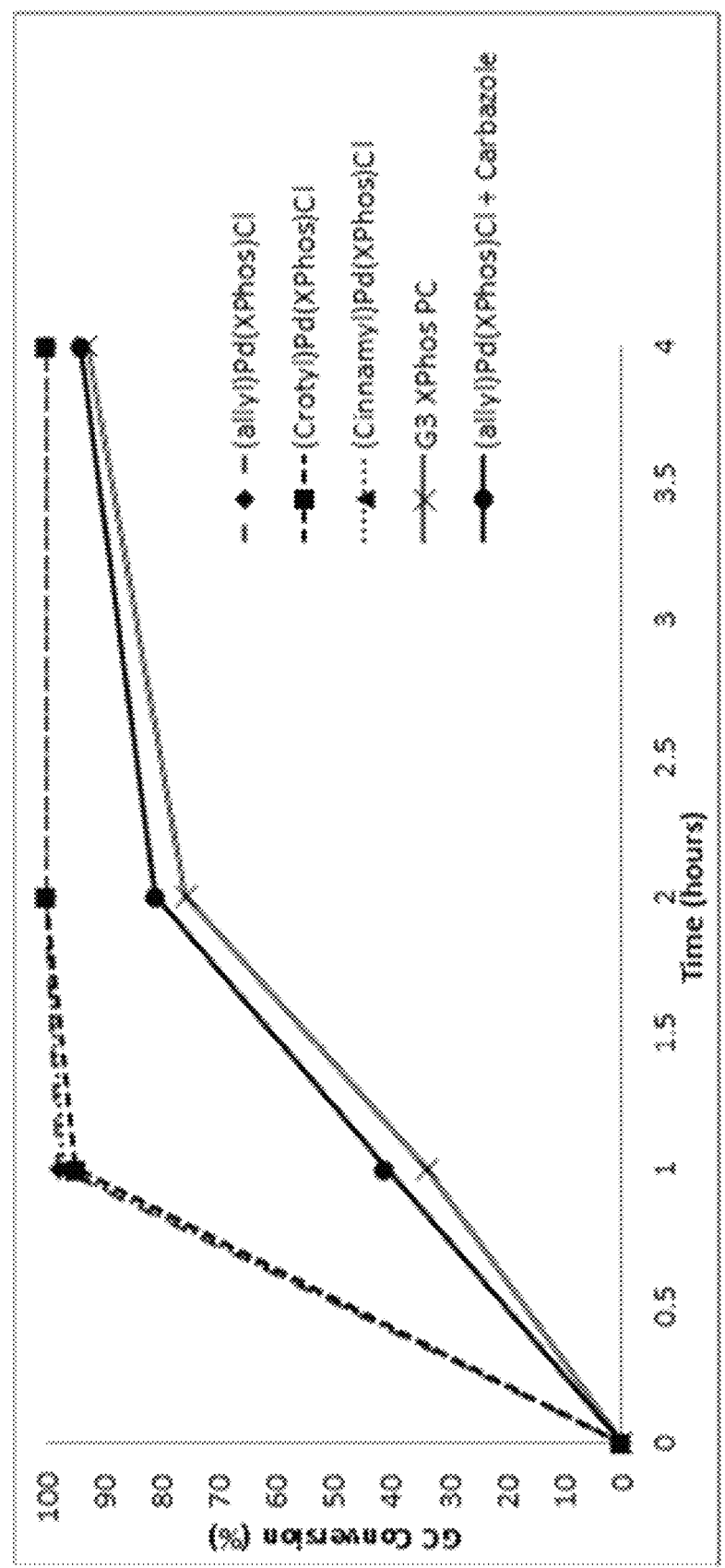
FIG. 7 illustrates the rate of conversion in the α-arylation of acetophenone with 4-chloroanisole using (π-allyl)Pd(XPhos)Cl, (π-crotyl)Pd(XPhos)Cl, (T-cinnamyl)Pd(XPhos)Cl, $3^{rd}$ generation XPhos palladacycle and (π-allyl)Pd(XPhos)Cl with 1 mol % added carbazole.

The XPhos complexes (π-allyl)Pd(XPhos)Cl, (π-crotyl)Pd(XPhos)Cl and (π-cinnamyl)Pd(XPhos)Cl were evaluated in the monoarylation of ketone enolates. These complexes all promoted rapid conversion (≥95%) after 1 hour in the α-arylation of acetophenone with 4-chloroanisole (see FIG. 7). The rate of conversion is significantly lower when G3 XPhos was employed as the precatalyst; 34% conversion is observed at 1 hour, and 4 hours was necessary to reach high conversion (93%). Carbazole is shown to retard the rate of this reaction, albeit to a lesser extent than in amination. The kinetic profile of the reaction catalyzed by (π-allyl)Pd(XPhos)Cl with 1 mol % of carbazole added nearly matched that of the G3 XPhos-catalyzed reaction.

Four examples of ketone enolate arylations using (π-allyl)Pd(XPhos)Cl highlight the versatility of this catalyst:

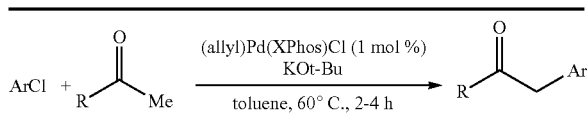

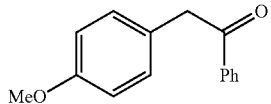

93%

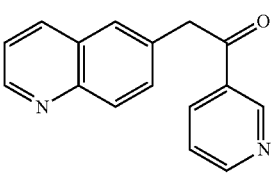 [SMILES: O=C(Cc1ccc2ncccc2c1)c1cccnc1]

95%

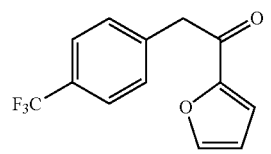 [SMILES: O=C(Cc1ccc(C(F)(F)F)cc1)c1ccco1]

64%[a]

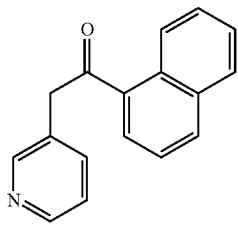

96%

Reaction conditions: ArCl (1.0 mmol), ketone (2.0 mmol), KOt-Bu (2.0 mmol), (π-allyl)Pd(XPhos)Cl(1 mol %), toluene (4 mL), 60° C., 2-4 h.
[a]2 mol % of (π-allyl)Pd(XPhos)Cl used.

General Procedure for the Ketone Enolate Arylation Reactions

An oven dried Schlenk tube equipped with a Teflon-coated magnetic stir bar is charged with (π-allyl)Pd(XPhos)Cl (1-2 mol %, as indicated), aryl chloride (1.00 mmol, if solid), and KOt-Bu (2.00-2.40 mmol, as indicated). The tube is capped with a rubber septum and was evacuated and backfilled with nitrogen. This evacuation/backfill cycle is repeated two additional times. Dodecane (GC standard, 0.20 mmol), the ketone (1.20 mmol), aryl chloride (1.00 mmol, if liquid), and anhydrous toluene (4 mL) are added sequentially via syringe. The tube is placed in a preheated oil bath (60° C.) and stirred for the indicated time. The tube is then removed from the oil bath and allowed to cool to room temperature. Saturated NH$_4$Cl (4 mL) and EtOAc (10 mL) are added, and the aqueous phase is extracted with EtOAc (3×10 mL). The organic extracts are combined, dried over anhydrous MgSO$_4$, filtered, and concentrated in vacuo. The residue is chromatographed on silica gel using a Teledyne ISCO CombiFlashRf.

2-(4-methoxyphenyl)-1-phenylethan-1-one

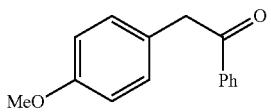

According to the general procedure, a mixture of 4-chloroanisole (123 µL, 1.00 mmol), acetophenone (140 µL, 1.20 mmol), KOtBu (224 mg, 2.00 mmol), (π-allyl)Pd(XPhos)Cl (6.6 mg, 0.01 mmol), and 4 mL of toluene are stirred at 60° C. for 2 hours. The crude material is chromatographed on silica gel with a gradient of 0-4% EtOAc/hexanes as the eluent to give 210 mg (0.93 mmol, 93%) of 2-(4-methoxyphenyl)-1-phenylethan-1-one as a colorless solid. The spectroscopic data match those previously reported (M. R. Biscoe, S. L. Buchwald, Org. Lett. 2009, 11, 1773).

1-(pyridin-3-yl)-2-(quinolin-6-yl)ethan-1-one

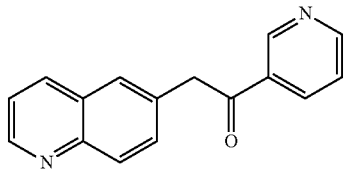 [SMILES: O=C(Cc1ccc2ncccc2c1)c1cccnc1]

According to the general procedure, a mixture of 6-chloroquinoline (164 mg, 1.00 mmol), 3-acetylpyridine (132 µL, 1.20 mmol), KOtBu (269 mg, 2.40 mmol), (π-allyl)Pd(XPhos)Cl (6.6 mg, 0.01 mmol), and 4 mL of toluene are stirred at 60° C. for 4 hours. The crude material is chromatographed on silica gel with EtOAc as the eluent to give 236 mg (0.95 mmol, 95%) of 1-(pyridin-3-yl)-2-(quinolin-6-yl)ethan-1-one as a pale yellow solid.

$^1$H NMR (400 MHz, CDCl$_3$, δ): 9.29 (s, 1H), 8.90 (d, J=3.5 Hz, 1H), 8.88 (d, J=3.5 Hz, 1H), 8.29 (d, J=8.2 Hz, 1H), 8.17-8.02 (m, 2H), 7.72 (s, 1H), 7.65 (d, J=8.5 Hz, 1H), 7.47-7.31 (m, 2H), 4.50 (s, 2H).

$^{13}$C NMR (100 MHz, CDCl$_3$, δ): 196.1, 153.8, 150.6, 150.1, 147.6, 135.9, 135.8, 132.1, 131.8, 131.2, 130.1, 128.4, 128.2, 123.9, 121.5, 45.7.

HRMS (ESI) m/z [M+H]$^+$ Calcd. for C$_{16}$H$_{13}$N$_2$O: 249.1028. Found: 249.1020.

1-(furan-2-yl)-2-(4-(trifluoromethyl)phenyl)ethan-1-one

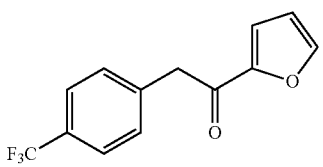

According to the general procedure, a mixture of 4-chlorobenzotrifluoride (133 µL, 1.00 mmol), 2-acetylfuran (132 µL, 1.20 mmol), KOtBu (269 mg, 2.40 mmol), (π-allyl)Pd(XPhos)Cl (13.2 mg, 0.02 mmol), and 4 mL of toluene are stirred at 60° C. for 4 hours. The crude material is chromatographed on silica gel with EtOAc as the eluent to give 236 mg (0.95 mmol, 95%) of 1-(furan-2-yl)-2-(4-(trifluoromethyl)phenyl)ethan-1-one as a pale yellow solid. The spectroscopic data match those previously reported (T. Miura, S. Fujioka, N. Takemura, H. Iwasaki, M. Ozeki, N. Kojima, M. Yamashita, *Synthesis*, 2014, 46, 496).

1-(naphthalen-1-yl)-2-(pyridin-3-yl)ethan-1-one

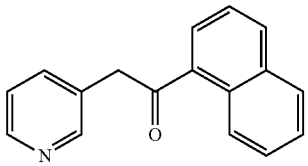 [SMILES: O=C(Cc1cccnc1)c1cccc2ccccc12]

According to the general procedure, a mixture of 3-chloropyridine (95 μL, 1.00 mmol), 1-acetonaphthalene (182 μL, 1.20 mmol), KOtBu (269 mg, 2.40 mmol), (π-allyl)Pd(XPhos)Cl (13.2 mg, 0.02 mmol), and 4 mL of toluene are stirred at 60° C. for 4 hours. The crude material is chromatographed on silica gel with 50% EtOAc/hexanes as the eluent to give 237 mg (0.96 mmol, 96%) of 1-(naphthalen-1-yl)-2-(pyridin-3-yl)ethan-1-one as a yellow oil.

$^1$H NMR (400 MHz, CDCl$_3$, δ): 8.61-8.49 (m, 3H), 8.01-7.94 (m, 2H), 7.89 (dd, J=1.6 Hz, 7.9 Hz, 1H), 7.63 (dt, J=1.8 Hz, 7.8 Hz, 1H), 7.60-7.48 (m, 3H), 7.29-7.23 (m, 1H), 4.38 (s, 2H).

$^{13}$C NMR (100 MHz, CDCl$_3$, δ): 200.3, 150.8, 148.5, 137.2, 135.0, 134.1, 133.4, 130.4 (2 peaks), 128.6, 128.3, 128.2, 126.8, 125.8, 124.4, 123.6, 45.7.

HRMS (ESI) m/z [M+H]$^+$ Calcd. for C$_{17}$H$_{14}$NO: 248.1075. Found: 248.1075.

Example 9 (According to the Invention)

Trifluoromethanation Using (π-allyl)Pd(BrettPhos)Cl

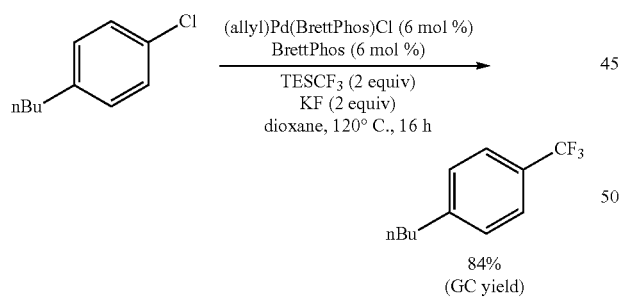

In a nitrogen filled glovebox a 2 dram reaction vial equipped with a Teflon-coated magnetic stir bar is charged with (allyl)Pd(BrettPhos)Cl (21.6 mg, 30 μmol), BrettPhos (16.1 mg, 30 μmol), and potassium fluoride (58.1 mg, 1.0 mmol). Dioxane (1.65 mL), triethyl(trifluoromethyl)silane (188 μL, 1.0 mmol), and 1-nbutyl-4-chlorobenzene (84.3 μL, 0.50 mmol) are added via syringe. The reaction vial is capped with an open top cap and PTFE Faced Silicone septum, removed from the glovebox, and placed on a preheated aluminum block (120° C.) and stirred vigorously for 16 hours. After cooling to room temperature the vial is opened to air and an aliquot (~200 μL) is removed, passed through a plug of Celite, eluted with ethyl acetate (2 mL) and analyzed by GC. The benzotrifluoride product is observed in 84% GC yield (uncalibrated).

This experiment demonstrates that the precatalyst (π-allyl)Pd(BrettPhos)Cl is competent in the trifluoromethanation of 4-n-butyl-1-chlorobenzene.

The invention claimed is:

1. A palladium complex of formula (2):

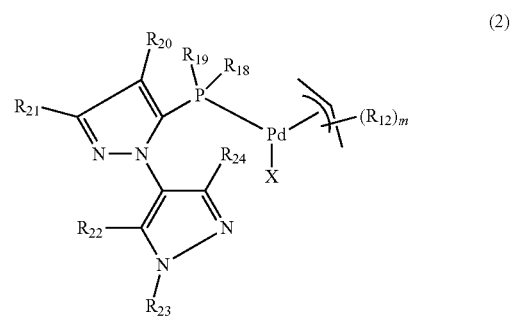

wherein:
R$_{18}$ and R$_{19}$ are, independently, -Me, -Et, -$^n$Pr, -$^i$Pr, -$^n$Bu, -$^i$Bu, cyclohexyl, or cycloheptyl;
R$_{12}$ is an optionally substituted straight-chain C$_{1-20}$ alkyl, optionally substituted branched-chain C$_{3-20}$ alkyl, optionally substituted C$_{3-20}$ cycloalkyl, optionally substituted C$_{6-20}$ aryl, or optionally substituted heteroaryl having 1-20 carbon atoms;
R$_{20}$ and R$_{21}$ are both hydrogen;
R$_{22}$, R$_{23}$, and R$_{24}$ are phenyl;
m is 0 or 1; and
X is a coordinated halo or trifluoroacetate ligand.

2. The palladium(II) complex of claim 1, wherein R$_{18}$ and R$_{19}$ are the same and are cyclohexyl.

3. The palladium(II) complex of claim 1, wherein the complex of formula (2) is:

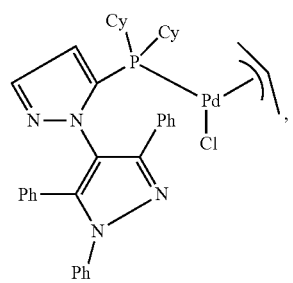

(π-allyl)Pd(CyBippyPhos)Cl

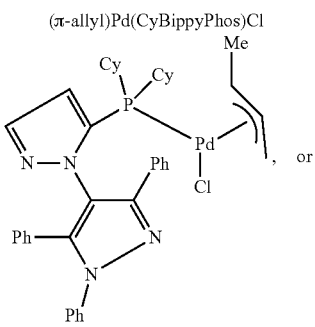

(π-crotyl)Pd(CyBippyPhos)Cl

-continued

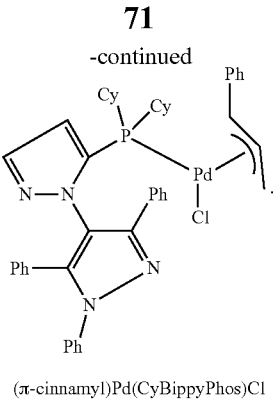

(π-cinnamyl)Pd(CyBippyPhos)Cl

4. A process for preparing a complex of formula (2):

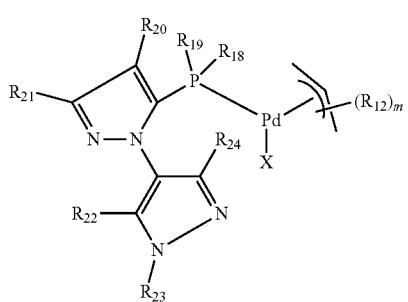
(2)

wherein:
- $R_{12}$ is an optionally substituted straight-chain $C_{1-20}$ alkyl, optionally substituted branched-chain $C_{3-20}$ alkyl, optionally substituted $C_{3-20}$ cycloalkyl, optionally substituted $C_{6-20}$ aryl, or optionally substituted heteroaryl having 1-20 carbon atoms;
- $R_{18}$ and $R_{19}$ are, independently, -Me, -Et, -$^n$Pr, —$^i$Pr, -$^n$Bu, -$^i$Bu, cyclohexyl, or cycloheptyl;
- $R_{20}$ and $R_{21}$ are both hydrogen;
- $R_{22}$, $R_{23}$, and $R_{24}$ are phenyl;
- m is 0 or 1; and
- X is a coordinated halo or trifluoroacetate ligand;

the process comprising reacting a complex of formula (3) with a monodentate bi-heteroaryl tertiary phosphine ligand of formula (5) to form the complex of formula (2):

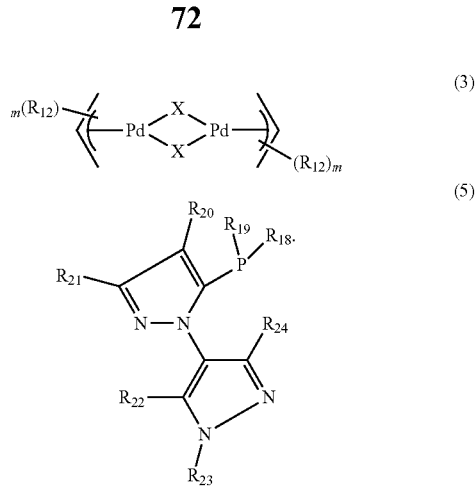

5. A process for performing a carbon-carbon coupling reaction in the presence of a catalyst, the process comprising using the complex of formula (2) of claim 1.

6. A process for performing a carbon-heteroatom coupling reaction in the presence of a catalyst, the process comprising using the complex of formula (2) of claim 1.

7. The palladium(II) complex of claim 1, wherein each $R_{12}$ is independently an optionally substituted straight-chain $C_{1-20}$ alkyl, optionally substituted branched-chain $C_{3-20}$ alkyl, or an optionally substituted $C_{6-20}$ aryl.

8. The palladium(II) complex of claim 1, wherein each $R_{12}$ is independently an optionally substituted straight-chain $C_{1-20}$ alkyl or an optionally substituted $C_{6-20}$ aryl.

9. The palladium(II) complex of claim 1, wherein each $R_{12}$ is independently a methyl, phenyl, or substituted phenyl group.

10. The palladium(II) complex of claim 1, wherein X is a halo group.

11. The palladium(II) complex of claim 1, wherein X is chloro.

12. The palladium complex of claim 1, wherein
- $R_{18}$ and $R_{19}$ are both cyclohexyl;
- $R_{12}$ is methyl, phenyl, or substituted phenyl group;
- $R_{20}$ and $R_{21}$ are hydrogen;
- $R_{22}$, $R_{23}$, and $R_{24}$ are phenyl;
- m is 0 or 1; and
- X is chloro.

* * * * *